US008540968B2

(12) United States Patent
Weichert et al.

(10) Patent No.: US 8,540,968 B2
(45) Date of Patent: *Sep. 24, 2013

(54) PHOSPHOLIPID ETHER ANALOGS AS AGENTS FOR DETECTING AND LOCATING CANCER, AND METHODS THEREOF

(75) Inventors: Jamey Weichert, Fitchburg, WI (US); Marc Longino, Verona, WI (US); Anatoly Pinchuk, Madison, WI (US)

(73) Assignee: Cellectar, Inc., Madison, WI (US)

( * ) Notice: Subject to any disclaimer, the term of this patent is extended or adjusted under 35 U.S.C. 154(b) by 1107 days.

This patent is subject to a terminal disclaimer.

(21) Appl. No.: 11/316,620

(22) Filed: Dec. 20, 2005

(65) Prior Publication Data

US 2007/0020178 A1    Jan. 25, 2007

Related U.S. Application Data

(63) Continuation-in-part of application No. 10/906,687, filed on Mar. 2, 2005.

(60) Provisional application No. 60/593,190, filed on Dec. 20, 2004, provisional application No. 60/521,166, filed on Mar. 2, 2004.

(51) Int. Cl.
*A61K 49/00* (2006.01)

(52) U.S. Cl.
USPC ......... 424/9.4; 424/1.11; 424/1.65; 424/1.81; 424/1.85; 424/9.1

(58) Field of Classification Search
USPC .................... 424/1.11, 1.37, 1.49, 1.65, 1.69, 424/1.73, 1.77, 1.81, 1.85, 1.89, 9.1, 9.2, 424/9.3, 9.4, 9.5, 9.6, 9.7, 9.8; 514/1, 75; 558/166
See application file for complete search history.

(56) References Cited

U.S. PATENT DOCUMENTS

| 4,925,649 | A | 5/1990 | Counsell | |
|---|---|---|---|---|
| 4,965,391 | A | 10/1990 | Counsell | |
| 5,087,721 | A | 2/1992 | Counsell | |
| 5,347,030 | A | 9/1994 | Counsell | |
| 5,369,097 | A | 11/1994 | Salari | |
| 5,626,654 | A | 5/1997 | Breton et al. | |
| 5,795,561 | A | 8/1998 | Counsell | |
| 5,965,108 | A | 10/1999 | Dean | |
| 6,255,519 | B1 * | 7/2001 | Counsell et al. | 558/166 |
| 6,417,384 | B1 * | 7/2002 | Counsell et al. | 558/166 |
| 6,503,478 | B2 | 1/2003 | Chaiken et al. | |
| 7,041,859 | B1 | 5/2006 | Kabalka | |
| 7,220,539 | B1 | 5/2007 | Du et al. | |
| 7,632,644 | B2 | 12/2009 | Weichert et al. | |
| 7,700,075 | B2 | 4/2010 | Weichert et al. | |
| 7,893,286 | B2 | 2/2011 | Pinchuk et al. | |
| 2002/0065429 | A1 | 5/2002 | Counsell | |
| 2005/0196339 | A1 | 9/2005 | Weichert et al. | |
| 2006/0013767 | A1 | 1/2006 | Weichert et al. | |
| 2006/0115426 | A1 | 6/2006 | Weichert et al. | |
| 2006/0228298 | A1 | 10/2006 | Weichert et al. | |
| 2007/0098633 | A2 | 5/2007 | Weichert et al. | |
| 2008/0075660 | A1 | 3/2008 | Weichert et al. | |
| 2008/0207492 | A1 | 8/2008 | Polt et al. | |
| 2008/0312459 | A1 | 12/2008 | Pinchuk et al. | |
| 2010/0316567 | A1 | 12/2010 | Weichert et al. | |
| 2011/0064660 | A1 | 3/2011 | Pinchuk et al. | |
| 2011/0064661 | A1 | 3/2011 | Pinchuk et al. | |
| 2012/0156133 | A1 | 6/2012 | Pinchuk et al. | |

FOREIGN PATENT DOCUMENTS

| CA | 2276284 A1 | 6/1998 |
|---|---|---|
| WO | WO 98/24480 A1 | 6/1998 |
| WO | WO 2005/063774 A1 | 7/2005 |
| WO | WO 2005/084716 A2 | 9/2005 |
| WO | WO 2006/014589 A2 | 2/2006 |
| WO | WO 2007/013894 A2 | 2/2007 |

OTHER PUBLICATIONS

Merck & Co., Inc., The Merck Index (1989), Iodine, p. 794.*
The Merck Index, 1989, Iodine (entry No. 4907), p. 794.*
Arthur, G. et al., The Inhibition of Cell Signaling Pathways . . . R. Biochim Biophys Acta. (1998) 1390:85-102.
Becher, R. et al., Phase II Trial of Orally Administered Miltefosine . . . Onkologie-Germany (1993) 16; 1:11-15.
Berdel, W.E. et al., Daily Oral Miltefosine (Hexadecylphosphocholine) . . . Onkologie-Germany (1992) 15:238-242.
Clezy, P.S. et al., The Chemistry of Pyrrolic Compounds, Aust. J.Chem., (1969) 22:239-49.
Counsell, R.E. et al., Tumor Visualization With a Radioiodinated Phospholipid . . . (1990) 31; 3:332-336.
Counsell, R.E. et al, Synthesis and Evluation of Radioiodinated Phospholipd Ether . . . Quart J. Nucl Med. (1997) 41(suppl 1):14-16.
Curley, SA et al., Radiofrequency Ablation of Unresectable Primary and Metastitic . . . Ann Surg. (1999) 230:1-8.
De Gramont, A. et al., Randomized Trial Comparing Monthly Low-Dose Leucovorin and . . . J. Clin. Oncol. (1997) 15:808-815.
Fong, Y. et al., Clinical Score for Predicting Recurrence After Hepatic Resection . . . Ann Surg. (1999) 230:309-318.
Giacchetti, S. et al., Phase III Multicenter Randomized Trial of Oxaliplatin Added . . . J. Clin. Oncol. (2000) 18:136-147.
Greven, K. et al., Can Positron Emission Tomography Distinguish Tumor . . . Cancer Journal Scientifica American (1997) 3:353-357.
Ike, H. et al., Results of Agressive Resection of Lung Matastases From Colorectal Carcinoma . . . Dis colon Rectum (2002) 45:468-473.
Imboden, M. et al., The Level of MHC Class I Expression on Murine Adenocarcinoma Can Change . . . Cancer Res. (2001) 61:1500-1507.
Kallman, R. F. Rodent Tumor Models in Experimental Cancer Therapy Pergamon Press, New York, (1987) pp. 111-132,.

(Continued)

*Primary Examiner* — D L Jones
(74) *Attorney, Agent, or Firm* — Wolf, Greenfield & Sacks, P.C.

(57) ABSTRACT

The present invention provides methods for treating, detecting and locating recurrence of cancer, radiation and chemo insensitive cancer or metastasis of cancer selected from the group consisting of Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer and Pancreatic cancer in subject using phospholipid ether analogs.

5 Claims, 14 Drawing Sheets

(56) References Cited

OTHER PUBLICATIONS

Lencioni, R. et al., Percutaneous Radiofrequency Thermal Ablation of Liver Malignancies: Techniques . . . Abdom Imaging (2001) 26:345-360.

Liebeskind L.S. et al., Heteroaromatic Thioether--Bornic Acid Cross-Coupling . . . Dept. of Chem., Emory University, Organic Letters (2002) 4; 6:979-981.

Longino, M.A. et al., Tumor Selective Rentention of NM404—Involvement of Phospholipase D. Molecular Imaging (2004), 3(3).

Maier, O. et al., Fluorescent Lipid Probes: Some Properties and Application (a Review) Chemistry and Physics of Lipids 116 (2002) 3-18.

Mayr, N.A. et al., Method and Timing of Tumor Volume Measurement for Outcome . . . Int. J. of Rad., Oncol., Bio., Phys. (2002) 52; 1:14-22.

Meta-Analysis:Modulation of Fluorouracil by . . . Advanced Colorectal Cancer Meta-Analysis Project. J. clin. Oncol. (1992) 10:896-903.

Moser, A.R. et al., Specificity of NM404 for Hyperplasia Versus Neoplasia in the . . . Online Aug. 15-18, 2003 Presentation No. 305.

O'Dwyer, P.J. et al., Follow-Up of Stage B and C Colorectal Cancer in the United States and . . . Seminars in Onology (2001) 28:Supp1-9, pp . 45-49.

Penna, C., et al., Colorectal Metastasis (Liver and Lung), Surg. clin. North Amer. (2002) 82:, pp. 1075-1090.

Pickhardt, P.J. et al., Computed Tomographic Virtual Colonoscopy to Screen for Colorectal . . . NE J. Med. (2003) 349; 23:2191-2200.

Plotzke, K.P. et. al., Selective Localization of a Radioiodinated Phospholipid Ether Analog in Human Tumor . . . J. Nucl. Med. (1993) 34(5):787-792.

Plotzke, K.P. et al., Selective Localization of Radioiodinated Alkylphosphocholine . . . Int. J. RadPart B, Nucl. Med. & Biology. (1992) 19(7):765-773.

Rampy, M.A. et al., Biological Disposition and Imaging of a Radioiodinated Alkylphosphocholine in Two Rodent . . . J. Nucl. Med. (1996) 37(9):1540-1545.

Rampy, M.A. et al., Synthesis and Biological Evaluation of Radioiodinated Phospholipid Ether Stereoisomers, J. Med. Chem. (1995) 38:3156-3162.

Saltz, L.B. et al., Irinotecan Plus Fluorouracil and Leucovorin for Metastiatic Colorectal Cancer . . . , N. Engl. J. Med. (2000) 343:905-91.

Snyder, F. et al., Alkyl and Alk-1-Enyl Ethers of Glycerol in Lipids From Normal and Neoplastic Human Tissues, Cancer Research. (1969) 29:251-257.

Snyder, F. et al., Occurrence and Nature of O-Alkyl and O-Alkyl-L-Enyl Moieties of Glycerol in Lipids of Morris . . . Biochem Biophys Acta. (1969) 176:502-510.

Solbiati, L. et al., Percutaneous Radio-Frequency Ablation of Hepatic Metastases From Colorectal Cancer: Long-Term . . . Radiology (2001) 221:159-166.

Stahl, A. et al., PET/CT Molecular Imaging in Abdominal Oncology, Abdominal Imaging (2004) 29:3(388-397).

Terwogt, J.M.M. et al., Phase II Trial of Topically Applied Miltefosine Solution in Optients With Skin-Metastasized . . . British J. of Cancer (1999) 79:1158-1161.

Wagner, R. et al., Boron-Dipyrromethene Dyes for Incorporation in Synthetic Multi-Pigment Light-Harvesting Arrays, Pure & Appl. Chem., (1996) 68; 7:1373-1380.

Weber, S.M. et al., Interleukin-1 Gene Transfer Results in CD8-Dependent Regression of Murine CT26 Liver Tumors, Ann. Surg. Oncol. (1999) 6:186-194.

Weichert, J.P. et al., Initial Clinical Imagining Results With NM404 in Non-Small Cell Lung Cancer, Molecular Imaging Online (2004) 3; 3:269-270.

Wichmann, M.W. et al., The Colorectal Cancer Study Group. Carcinoembryonic Antigen for the Detection . . . Anticancer Research (2000) 20:4953-4955.

Zasadny, K.R. et al., Predicted Dosimetry for I-131-NM404, A Phospholipid Ether Agent for Tumor Imaging and Possible Therapy, J Nucl Med. (1999) 40(5):39P.

Sik, M.D. et al., Neoplastic Transformation and Tumorrigensis Associated With Overexpress . . . Database Biosis(Online) (Oct. 2001) XP002365147 Database No. PREV200100523916, pp. 1641-1647.

Hirokazu O. et al., Increased Activity and Expression of Phospholipase D2 in Human . . . Database Biosis (Online) (2003) XP002365146 Database No. PREV00300566956.

Dong-Young, N. et al., Overexpression of Phospholipase D1 in Human Breast Cancer Tissues, Database Biosis (Online) (Dec. 2000) XP0102365186 Database No. PREV200100047408.

Weichert, J. et al., Specificity of NM404 for Hyperplasia versus Neoplasia in the APC . . . Oasis—Online Abstrct Submission and Invitation System, 1996-2007.

Weichert JP et al "Evaluation of 125I-NM404 in a Spontaneous Murine Pancreatic Adenocarcinoma . . . ", Aug. 2003, 2nd Annual Meeting of the Society of Molecular Imaging, San.

Weichert J. et al., Radioiodination Via Isotope Exchange in Pivalic Acid, Appl. Radiat Isot (1986) vol. 37, No. 8, 907-913.

Weichert J. et al., Polyiodinated Triglyceride Analogs As Potential Computed Tomography Imaging Agents for the Liver, J Med Chem (1995) 38, 636-646.

Pinchuk A et al., Synthesis and Structure-Activity Relationship Effects on the Tumor Avidity of Radioiodinated Phospholipid Ether Analogues, J Med Chem (2006), 49, 2155-2165.

Partial European Search Report for EP 08010321.1 mailed Jul. 13, 2009.

Extended European Search Report for EP 08010321.1 mailed Oct. 6, 2009.

Extended European Search Report for EP 08020805.1 mailed Jul. 14, 2009.

Invitation to Pay Additional Fees for PCT/US2005/006681 mailed Nov. 8, 2005.

International Search Report and Written Opinion for PCT/US2005/006681 mailed Feb. 20, 2006.

International Preliminary Report on Patentability for PCT/US2005/006681 mailed Sep. 14, 2006.

International Search Report and Written Opinion for PCT/US2005/024259 mailed Mar. 1, 2006.

International Preliminary Report on Patentability for PCT/US2005/024259 mailed Jan. 18, 2007.

International Search Report and Written Opinion for PCT/US2005/047657 mailed Jan. 22, 2007.

International Preliminary Report on Patentability for PCT/US2005/047657 mailed Jul. 5, 2007.

International Search Report and Written Opinion for PCT/US2010/048340 mailed Oct. 14, 2010.

Invitation to Pay Additional Fees for PCT/US2010/038294 mailed Jul. 23, 2010.

International Search Report and Written Opinion for PCT/US2010/048351 mailed Oct. 19, 2010.

International Search Report for PCT/US2007/017885 mailed Aug. 14, 2008.

International Preliminary Report on Patentability for PCT/US2007/017885 mailed Feb. 26, 2009.

Written Opinion for PCT/US2007/017885 mailed Jul. 31, 2008.

Canadian Office Action for Application No. 2557698 dated Dec. 8, 2010.

Chinese Office Action for Application No. 200580007056.9 dated Mar. 6, 2009.

European Office Action for Application No. 05729873.9 dated Apr. 26, 2007.

Summons to Attend Oral Proc for Application No. 05729873.9 dated Jan. 22, 2008.

European Office Action for Application No. 05729873.9 dated Jun. 16, 2008.

European Office Action for Application No. 05729873.9 dated Mar. 23, 2009.

Israeli Office Action for Application No. 177645 dated Aug. 13, 2009.

Israeli Office Action for Application No. 177645 dated May 13, 2010.

Indian Office Action for Application No. 4875/DELNP/2006 dated Jun. 7, 2011.
Japanese Office Action for Application No. 2007-501917 dated Dec. 7, 2010.
Mexican Office Action for Application No. PA/a/2006/009681 dated Nov. 20, 2008.
New Zealand Office Action for Application No. 549562 dated Mar. 5, 2009.
New Zealand Office Action for Application No. 549562 dated Sep. 23, 2009.
New Zealand Office Action for Application No. 549562 dated Dec. 1, 2009.
New Zealand Office Action for Application No. 549562 dated Jan. 12, 2010.
Office Communication for U.S. Appl. No. 10/906,687 mailed Mar. 16, 2009.
Office Communication for U.S. Appl. No. 10/906,687 mailed Nov. 2, 2009.
Office Communication for U.S. Appl. No. 10/906,687 mailed Oct. 5, 2010.
Office Communication for U.S. Appl. No. 10/906,687 mailed May 24, 2011.
Australian Office Action for Application No. 2005-269861 dated Jan. 13, 2010.
Chinese Office Action for Application No. 200580026935.6 dated May 8, 2009.
Chinese Office Action for Application No. 200580026935.6 dated Nov. 27, 2009.
European Office Action for Application No. 05769481.2 dated Dec. 21, 2007.
Israeli Office Action for Application No. 180363 dated Sep. 13, 2009.
New Zealand Office Action for Application No. 552914 dated Apr. 24, 2009.
New Zealand Office Action for Application No. 552914 dated Nov. 17, 2009.
New Zealand Office Action for Application No. 552914 dated Dec. 2, 2009.
Office Communication for U.S. Appl. No. 11/177,749 mailed Apr. 1, 2009.
Notice of Allowance for U.S. Appl. No. 11/177,749 mailed Nov. 23, 2009.
European-Office Action for Application No. 05858499.6 dated Oct. 9, 2007.
Mexican Office Action for Application No. MX/a/2007/007497 dated Apr. 5, 2010.
Notice of Allowance for U.S. Appl. No. 12/156,287 mailed Oct. 12, 2010.
Office Communication for U.S. Appl. No. 11/382,645 mailed Apr. 22, 2009.
Office Communication for U.S. Appl. No. 11/671,403 mailed Apr. 6, 2009.
Notice of Allowance for U.S. Appl. No. 11/382,645 mailed Sep. 24, 2009.
Office Communication for U.S. Appl. No. 11/891,939 mailed Dec. 3, 2008.
[No Author Listed] "Therapy" Stedman's Medical Dictionary 27th Edition. copyright@ 2000 Lippincott Williams & Wilkins. Last accessed on Oct. 19, 2009 at http://www.thomsonhc.com.pdrel/librarian/PFDefaultActionld?.. 11 pages.
Brownstein, Clinical Experience with Inorganic, Non-radioactive Iodine-Iodide. The Original Internist. 2005:105-8.
Chia et al., Abberations in Phospholipase D Activity-A Pharmacological Target for Cancer Detection. The FASEB Journal. 2006;20:A488. Abstract 330.10.
Golub et al., Molecular classification of cancer: class discovery and class prediction by gene expression monitoring. Science. Oct. 15, 1999;286(5439):531-7.
Hunt et al., Assessment of the aggregation state of integral membrane proteins in reconstituted phospholipid vesicles using small angle neutron scattering. J Mol Biol. Nov. 14, 1997;273(5):1004-19.
Jhanwar et al., Current status of therapy of solid tumors. J Nucl Med. Jan. 2005;46 Suppl 1:141S-50S.

Kuerschner et al., Polyene-lipids: a new tool to image lipids. Nat Methods. Jan. 2005;2(1):39-45. Epub Dec. 21, 2004.
Longino et al., Preliminary Clinical Imaging and Pharmacokinetic Results with NM404 in Non-Small Cell Lung Cancer. Presented at the 5th International Symposium on Radiohalogens meeting in Whistler, B.C. Sep. 11-15. Slideshow presentation on Sep. 15, 2004. Last accessed on Jul. 13, 2011 at http://legacyweb.triumfca/51SR/44-CS29- NM404%20Imaging%20&%2OPK.pdf. 20 pages.
Longino et al., Preliminary Clinical Imaging and Pharmacokinetic Results with NM404 in Non-Small Cell Lung Cancer. Presentation abstract. Presented at the 5th International Symposium on Radiohalogens meeting in Whistler, B.C. Sep. 11-15, 2004. Last accessed on Jul. 13, 2011 at http://legacyweb.triumica/5ISR/5ISR%20Abstracts.pdf.
Murray et al., Phase II radioimmunotherapy trial with 131I-CC49 in colorectal cancer. Cancer. Feb. 1, 1994;73(3 Suppl):1057-66.
Pickhardt et al., Microcomputed tomography colonography for polyp detection in an in vivo mouse tumor model. Proc Natl Acad Sci U S A. Mar. 1, 2005;102(9):3419-22. Epub Feb. 22, 2005.
Quon, et al., "Flying through" and "flying around" a PET/CT scan: Pilot study and development of 3D integrated 18F-FDG PET/CT for virtual bronchoscopy and colonoscopy. J Nucl Med. Jul. 2006;47(7):1081-7.
Wang et al., Molecular imaging with 123I-FIAU, 18F-FUdR, 18F-FET, and 18F-FDG for monitoring herpes simplex virus type 1 thymidine kinase and ganciclovir prodrug activation gene therapy of cancer. J Nucl Med. Jul. 2006;47(7):1161-71.
International Preliminary Report on Patentability for PCT/US2010/048340 mailed Mar. 22, 2012.
Office Communication for U.S. Appl. No. 10/906,687 mailed Apr. 21, 2010.
Japanese Office Action for Application No. 2007-501917 dated Sep. 13, 2011.
[No Author Listed] Database Registry RN 208986-86-9 26. Jul. 1998. 1 page.
Counsell et al, Isotope Production and Applications in the 21st Century, Proceedings of the International Conference on Isotopes, 3rd, Vancouver, BC, Canada, Sep. 6-10, 1999 (2000), Meeting Date 1999, 163-166.
Goud et al., Synthesis of 8-heteroatom-substituted 4,4-difluoro-4-bora-3a, 4a-diaza-s-indacene dyes (BODIPY). Tetrahedron. 2006;62:5084-91.
Jurcic et al., Radiolabeled anti-CD33 monoclonal antibody M195 for myeloid leukemias. Radiolabeled anti-CD33 monoclonal antibody M195 for myeloid leukemias. Cancer Res. Dec. 1, 1995;55(23 Suppl):5908s-5910s.
Kamigaki et al., Therapy and imaging of pancreatic carcinoma xenografts with radioiodine-labeled chimeric monoclonal antibody A10 and its Fab fragment. Jpn J Cancer Res. Dec. 1995;86(12):1216-23.
Meyer et al., Potential tumor or organ-imaging agents. 30. Radioiodinated phospholipid ethers. J Med Chem. Sep. 1989;32(9):2142-7.
Miyagawa et al., Imaging of HSV-tk Reporter gene expression: comparison between [18F]FEAU, [18F]FFEAU, and other imaging probes. J Nucl Med. Apr. 2008;49(4):637-48. Epub Mar. 14, 2008.
Nakabeppu et al., Radionuclide therapy of malignant pheochromocytoma with 131I-MIBG. Ann Nucl Med. Nov. 1994;8(4):259-68.
Plotzke et al., Biodistribution, metabolism, and excretion of radioiodinated phospholipid ether analogs in tumor-bearing rats. J Nucl Biol Med. Dec. 1993;37(4):264-72.
Rampy et al. Synthesis and biological evaluation of radioiodinated phospholipid ether analogs. Nucl Med Biol. May 1995;22(4):505-12.
Weichert, Noninvasive Evaluation of Colon Tumors in Live Mice using MicroCT Virtual colonoscopy. Academy of Molecular Imaging Meetings-Orlando. Mar. 18-23, 2005. Presented on Mar. 22, 2005. Slideshow presentation. 40 pages.
European Office Action for Application No. 08010321.1 dated May 8, 2012.

European Office Action for Application No. 08020805.1 dated May 3, 2012.

Office Communication for U.S. Appl. No. 12/879,093 mailed May 3, 2012.

Office Communication for U.S. Appl. No. 10/906,687 mailed Dec. 19, 2012.

Office Communication for U.S. Appl. No. 12/813,992 mailed Jul. 27, 2012.

Office Communication for U.S. Appl. No. 12/879,167 mailed Oct. 5, 2012.

Office Communication for U.S. Appl. No. 13/403,445 mailed Oct. 3, 2012.

Nijsen et al., Radioactive holmium loaded poly(L-lactic acid) microspheres for treatment of hepatic malignancies: efficacy in rabbits. Thesis. 2001. Chapter 7. pp. 109-122. (The year of publication is sufficiently earlier than the effective U.S. filed and any foreign priority date so that the particular month of publication is not in issue. See MPEP 609.04(a)).

* cited by examiner

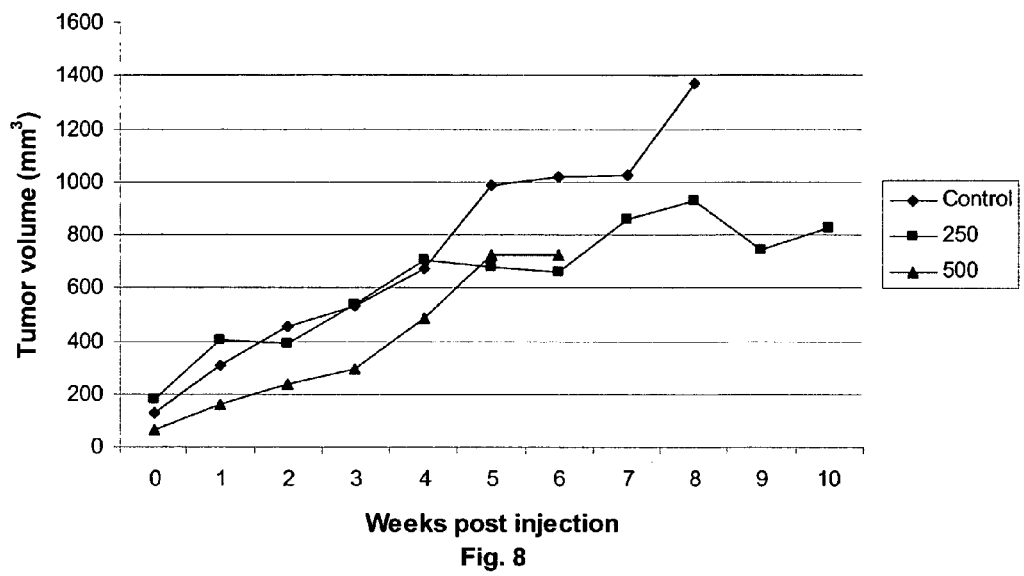
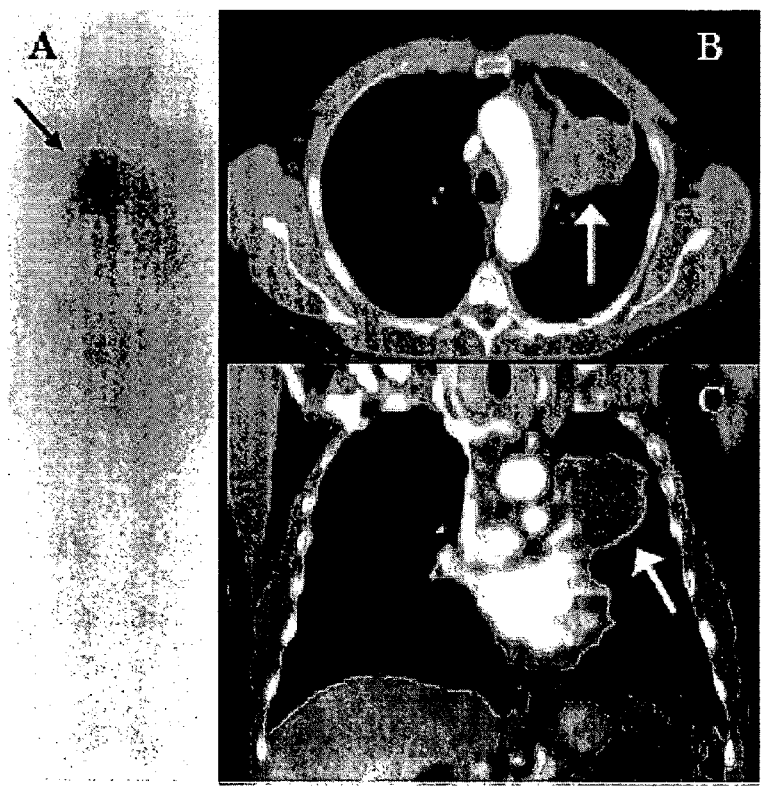
Fig. 8
Fig. 9

PHOSPHOLIPID ETHER ANALOGS AS AGENTS FOR DETECTING AND LOCATING CANCER, AND METHODS THEREOF

RELATED APPLICATION:

The present application seeks priority from U.S. Provisional Application No. 60/593,190 filed on Dec. 20, 2004 and is a Continuation-in-Part of U.S. application Ser. No. 10/906,687 filed on Mar. 2, 2005, which in turn seeks priority from U.S. Provisional Application No. 60/521,166, filed on Mar. 2, 2004, all of which are incorporated herein by reference for all purposes.

BACKGROUND OF INVENTION:

The invention generally relates to phospholipids ether analogs and use thereof and specifically relates to use of phospholipid ether analogs and combinations thereof for diagnosis of metastasis, treatment, pharmacokinetic, dosimetry, and toxicity studies of various cancer types, such as non-small cell lung cancer, prostate cancer and metastasis thereof.

Non-small Cell Lung Cancer (NSCLC)

Non-small cell lung cancer (NSCLC) is the leading cause of cancer death in the United States today. Surgical resection in appropriately selected patients offers the best chance for cure. Accurate pre-operative assessment of local, regional and distant metastatic spread is thus critical for optimal management.

Imaging with FDG PET scanning has recently become the "gold standard" for imaging NSCLC, due to improved sensitivity, particularly when compared with CT imaging. However, its sensitivity for identifying mediastinal lymph node involvement is only about 90%, and lack of specificity, particularly in patients with inflammatory or granulomatous disease, is particularly problematic. Furthermore, its utility in diagnosing brain tumors or metastases is limited due to high metabolic background of normal brain tissue.

Evaluation of the mediastinal lymph node status is essential because nodal metastasis, which occurs in nearly half of all patients with NSCLC, is probably the most frequent barrier to cure. Accurate staging may also spare patients the morbidity of unnecessary, non-curative surgical procedures. Hence, there remains a need for an imaging technique that is more sensitive, specific, and accurate than any currently available technology.

Current conventional modalities have limitations. Anatomic imaging with computed tomography (CT) and magnetic resonance imaging (MRI) are impractical for whole body screening but are the most widely used non-invasive imaging methods for evaluation of loco-regional spread. However, CT relies on size criteria of over one centimeter for diagnosing abnormal nodes.

Positron-emission tomography (PET) scanning with $^{18}$F-fluorodeoxyglucose (FDG) has generated considerable interest as an oncologic imaging technique. A recent study prospectively compared the ability of a standard approach to staging for NSCLC (CT, ultrasound, bone scanning, etc) and PET scanning to detect metastases in mediastinal lymph nodes and distant sites. Mediastinal involvement was confirmed histopathologically, and distant metastases were confirmed by other imaging tests. The sensitivity and specificity of PET for detecting mediastinal metastases were 91% and 86%, respectively; for detecting distant metastases, 82% and 93%, respectively. This compares to sensitivity and specificity for CT scanning of mediastinal involvement 75% and 66%, respectively. A meta-analysis involving 39 studies and over 1000 patients also found that FDG-PET was more accurate than CT for mediastinal staging, (sensitivity and specificity of 85% and 90%, respectively, for FDG-PET and 61% and 79% for CT scanning), although FDG-PET became less specific when CT showed enlarged mediastinal lymph nodes (78%).

FDG-PET has been shown to reduce futile thoracotomies in patients. However, because of the false positive and false negative rate, confirmatory mediastinoscopies are often recommended. For example, a retrospective study involving over 200 patients with NSCLC found that the sensitivity, specificity, positive and negative predictive values, and accuracy for FDG-PET were 64%, 77%, 45%, 88%, and 75%, respectively.

FDG-PET also plays a role in diagnosing extra-thoracic disease, particularly in patients with intermediate stages of lung cancer. A study done by the American College of Physicians involving over 300 patients found that unsuspected metastatic disease or second primary malignancies was identified in 18 of 287 patients (6.3%). Some studies, although not all, suggest that by correctly identifying advanced disease, PET will avoid unnecessary thoracotomy on 1 in 5 patients.

Conventional anatomic imaging techniques such as CT scanning are also poor at predicting survival following treatment. In a recent study involving 73 NSCLC patients receiving treatment with concurrent cisplatin-based chemo/radiotherapy or radiotherapy alone for advanced disease, response by conventional CT imaging did not correlate with survival. Response by FDG-PET scans, however, did correlate strongly with survival (p<0.001). Survival from the date of a follow-up PET scan was 84% and 84% at 1 and 2 years respectively for 24 patients who had achieved a complete response on PET, but only 43% and 31% of the 32 patients who did not (p=0.010). These results corroborate similar findings reported recently by other authors, which also show a correlation of uptake on PET scan with biological aggressiveness of tumor, and that PET imaging late after completion of treatment is highly predictive of future survival.

It is generally accepted that FDG-PET imaging is a poor method of identifying metastatic disease to the brain in patients with NSCLC. Under normal conditions, the gray matter of the brain has high glucose utilization and therefore the uptake of FDG is normally high. While cerebral metastatic disease is often quite metabolic and often does demonstrate increased FDG uptake, it frequently is less than the brain gray matter and therefore the cerebral metastases may not be conspicuous. In one series, the sensitivity and specificity for the identification of cerebral metastatic disease in patients with NSCLC was 60% and 99% for FDG-PET, and 100% and 100% for conventional imaging. Therefore, FDG-PET imaging is not considered to be the best method of evaluating a patient with NSCLC for metastatic disease to the brain.

Another disadvantage of FDG is that it is not specific for tumors, but accumulates in both malignant and non-malignant hypermetabolic tissues. The overwhelming majority of false positive results (positive result when the radiological abnormality is not due to cancer) with FDG-PET scans of the lung are due to inflammatory and infectious causes. FDG is a nonspecific tracer and accumulates in areas of infection or inflammation. In the lung, these areas can be localized lung parenchymal nodules or more diffuse (subsegmental, segmental or lobar) or in the hilar and mediastinal nodes. In a recent study from Japan, of 116 lung nodules 1-3 cm in diameter, 15 out of 73 malignant nodules were false negative on FDG-PET and 15 out of 43 benign nodules were false positive on FDG-PET. In focal pneumonias causing ground glass opacity nodules, the false positive rate was as high as 80%. In another study, ten patients with extrapulmonary cancer had false positive FDG-PET uptake in the lung; 6 had intense focal or multifocal uptake and four had uptake in a more segmental or lobar pattern. In all 10 patients, the uptake was due to consolidation or atelectasis and the final diagnosis on follow-up was pulmonary inflammation or infection. In addition to active bacterial pneumonias, false positive FDG-PET results can occur in many other infectious and inflammatory conditions in the lung. In the Midwestern US, many asymptomatic people have lung nodules and enlarged nodes due to previous infection with histoplasma; although many of these nodules are quiescent, some represent smoldering or active infection. Pulmonary sarcoidosis is probably one of the more common active inflammatory granulomatous processes in the lung. Interestingly, when serial FDG-PET scans have been performed in a patient being treated with oral corticosteroids for pulmonary sarcoidosis, FDG uptake decreased and then vanished.

FDG-PET is also frequently negative in malignancies with a low metabolic rate, such as bronchoalveolar carcinoma or carcinoid.

Therefore a radiopharmaceutical that could accurately identify early metastatic disease in the patients with NSCLC would have a significant impact on patient care, in terms of both staging and response to therapy. Although PET imaging has improved diagnostic efficacy in this area compared to CT, there remains a need for an accurate imaging technique that is not based upon metabolic activity, which is non-specific, but is based upon a tumor-specific function that can non-invasively screen the whole body, including the brain.

Prostate Cancer

Approximately 230,110 new cases of prostate cancer will be diagnosed in the United States for the year 2004 alone. Despite technical refinements in definitive local treatment of clinically organ confined prostate cancer by radical prostatectomy, such that many men are cured with primary therapy alone, as many as 40% of patients will experience biochemical recurrence with long-term follow-up. This recurrence is typically defined as a post-operative PSA level which is greater than or equal to 0.4 ng/ml since patients with PSA levels above this threshold generally develop clinical evidence for recurrence within 6-49 months although a PSA level of greater than or equal to 0.2 has been proposed more recently. With limited success, clinical and pathologic criteria are currently utilized to determine the likelihood for systemic disease recurrence. Factors increasing the likelihood of systemic recurrence include a high preoperative PSA level as well as pathologic features of the surgical specimen including Gleason score>7, seminal vesicle involvement, and lymph node involvement. In contrast, extracapsular extension, positive surgical margins and Gleason score<7 are factors generally associated with local recurrence. In addition, the velocity of PSA rise following prostatectomy has been utilized to determine whether disease recurrence is local or systemic. For instance, Partin et al reported that a PSA rise of less than 0.75 ng/ml/year was more frequently associated with local recurrence. Furthermore, Patel et al reported that a PSA doubling time of greater than 12 months correlated with local recurrence. Despite these clinical and pathologic criteria, the inventors are still unable to accurately select patients appropriately for local therapy such that many men may receive unnecessary hormonal ablation.

One of the greatest challenges in treating patients with clinically organ confined prostate cancer or patients with biochemical recurrence following definitive treatment of presumed organ-confined disease remains to accurately distinguish localized versus metastatic disease. This diagnostic capability is important to identify patients who may benefit from effective local treatment modalities including surgery, external beam radiation, brachytherapy, and cryotherapy. Because the inventors presently do not have an accurate means of staging, patients with occult metastatic disease may unnecessarily undergo local treatment with associated risks of therapy. Furthermore, patients with a rising PSA due to local recurrence, in whom systemic recurrence cannot be excluded with confidence, may unnecessarily undergo hormonal ablation, which is generally not considered curative and is associated with osteoporosis development, decreased libido, weight gain, menopausal symptoms, and overall malaise, as well as the evolution of hormonally independent prostate cancer.

While conventional imaging studies such as computed tomography (CT) and magnetic resonance imaging (MRI) are useful in assessing soft-tissue metastasis, the vast majority of prostate cancer metastasizes to the bone only. Thus, the utility of CT and MRI scanning in assessing the disease is suboptimal and more sensitive imaging modalities for either locally recurrent or metastatic prostate cancer are necessary. Radioimmunoscintigraphy with Indium-111 capromab pendetide (ProstaScint, Cytogen Corp, Princeton, N.J.) has been utilized in patients following prostatectomy with a rising PSA who have a high clinical suspicion of occult metastatic disease and no clear evidence for metastatic disease in other imaging studies. This scan is based on a radiolabeled murine monoclonal antibody which is specific for PSMA (Prostate-specific membrane antigen), a transmembrane protein which is specifically expressed by both normal and malignant prostate epithelial cells. While ProstaScint radioimmunoscintigraphy has been shown to be promising in diagnosing locally recurrent disease in the prostate bed in patients with rising PSA, clinical results for this scan have been somewhat variable, with sensitivities ranging between 44% and 92% and specificities between 36% and 86%. Furthermore, when subsequent biopsy was utilized as the standard of reference for local recurrence, false-negative ProstaScint studies have been reported in 10% to 20% of cases. In addition, false-positive uptake of ProstaScint has been reported in neurofibromatosis, lymphomas, renal carcinomas, pelvic kidneys, myolipomas, and meningiomas, as well as in the bone marrow of vertebral bodies. Given this data, use of the ProstaScint scan for patients at risk for occult metastases from prostate cancer remains controversial.

In patients with metastatic prostate cancer, positron-emission tomography (PET) imaging has recently been used to measure the metabolic activity of osseous metastases. This technique has proven to be effective in distinguishing active bony metastasis from osteoblast activity which occurs as a result of bone healing following successful treatment of metastatic disease. This question can be assessed better by PET than by either bone scan or CT. Furthermore, changes in PET scan findings can be seen as early as 4 weeks following initiation of systemic treatment in patients with metastatic prostate cancer, whereas in many cases no significant change is seen on conventional bone scan. Therefore imaging utilizing PET technology may be useful in monitoring response to treatment in these patients. PET scanning with $^{18}$F-FDG has generated considerable interest as an imaging technique. Recently, it has been shown that FDG-PET can distinguish between active and quiescent bone metastases in patients with prostate cancer. The intensity of FDG uptake is thought to reflect the metabolic and biological activity of these lesions in contrast to the traditional bone scan with technetium-diphosphonate compounds in which nonspecific osteoblast activity may be detected as a false positive signal following treatment. In addition, a false negative reading may be obtained since early metastases, which initially seed into the bone marrow, will not necessarily produce a signal until an osteoblastic response occurs. Therefore, a persistently positive bone scan does not necessarily indicate the presence of residual viable metastases and a negative bone scan result may not reflect accurately the patient's metastatic tumor burden. FDG-PET may therefore prove beneficial in guiding the management of patients with bony metastases and in a retrospective study FDG-PET and helical CT have been shown independently to be more effective than $^{111}$In-monoclonal antibody imaging in detecting metastatic disease.

Although the FDG-PET scan is a promising imaging technique in patients with prostate cancer, most prostate cancers are slow growing and therefore do not accumulate FDG, and thus do not image well with that agent. Furthermore, FDG is excreted in the urine and so the accumulation of FDG in the bladder will minimize the probability of detecting local recurrences of prostate cancer. Indeed Morris et al reported difficulty in detection of soft tissue metastases by FDG-PET alone when metastatic sites are obscured by anatomic pathways of tracer excretion. More recently, PET-CT has been found to be more effective than PET alone in identifying metastatic lesions in patients with suspected occult metastases. In a prospective study of patients with various tumor types, the specificity and accuracy with multiple radiologic interpretations were significantly higher for PET-CT.

Accordingly, the need exists for developing a more sensitive and specific imaging exam, molecular imaging agent, such as phospholipids ether compounds (PLE). It would be desirable to have tumor-selective radiopharmaceuticals, with minimal accumulation in the bladder, which could accurately identify early metastatic disease in patients with prostate cancer, would have an important impact on patient care, in terms of both staging and response to therapy.

SUMMARY OF THE INVENTION

The present invention provides a method for detecting and locating recurrence of cancer, radiation and chemo insensitive cancer or metastasis of cancer selected from the group consisting of Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer and Pancreatic cancer in subject that has or is suspected of having cancer. The method comprising the steps of: (a) administering a phospholipid ether analog to the subject; and (b) determining whether an organ suspected of having recurrence of cancer, radiation and chemo insensitive cancer or metastasis of cancer in the subject retains a higher level of the analog than surrounding region(s) wherein a higher retention region indicates detection and location of the recurrence of cancer, radiation insensitive and chemo cancer or metastasis of cancer.

In a preferred embodiment, the phospholipid analog is selected from:

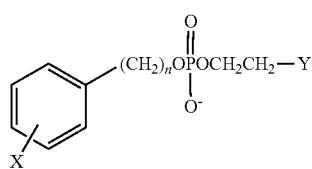

where X is selected from the group consisting of radioactive isotopes of halogen; n is an integer between 8 and 30; and Y is selected from the group comprising $NH_2$, $N(R)_2$, and $N(R)_3$, wherein R is an alkyl or arylalkyl substituent or

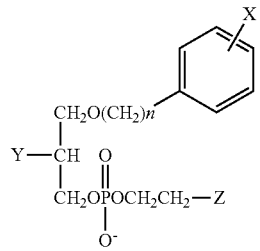

where X is a radioactive isotope of halogen; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. Further, in certain embodiments, X is selected from the group of radioactive halogen isotopes consisting of $^{18}$F, [36]Cl, [76]Br, [77]Br, [82]Br, [122]I, $^{123}$I, [124]I, $^{125}$I, $^{131}$I and [211]At. More preferably, the phospholipid ether is 18-(p-lodophenyl)octadecyl phosphocholine, 1-O-[18-(p-lodophenyl)octadecyl]-1,3-propanediol-3-phosphocholine, or 1-O-[18-(p-lodophenyl) octadecyl]-2-O-methyl-rac-glycero-3-phosphocholine, wherein iodine is in the form of a radioactive isotope. In this method, preferably the detection is carried out by a of PET, CT, MRI scanning methods combination thereof.

Another embodiment of the present invention provides a method for the treatment of recurrence of cancer, radiation and chemo insensitive cancer or metastasis of cancer in a subject. The method comprises administering to the subject an effective amount of a compound comprising a phospholipid ether analog. In a preferred embodiment, the recurrence of cancer, radiation and chemo insensitive cancer or metastasis of cancer occurs in the group selected from Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer, Pancreatic cancer and Carcinosarcoma. Also preferably, the phospholipid analog is selected from:

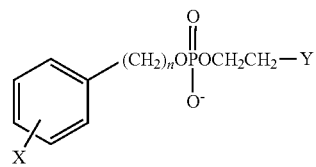

where X is selected from the group consisting of radioactive isotopes of halogen; n is an integer between 8 and 30; and Y is selected from the group comprising $NH_2$, $N(R)_2$, and $N(R)_3$, wherein R is an alkyl or arylalkyl substituent or

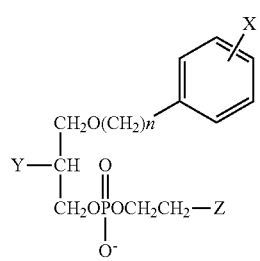

where X is a radioactive isotope of halogen; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. In this method, preferably, X is selected from the group of radioactive halogen isotopes consisting of $^{18}F$, $^{36}Cl$, $^{76}Br$, $^{77}Br$, $^{82}Br$, $^{122}I$, $^{123}I$, $^{124}I$, $^{125}I$, $^{131}I$, $^{211}At$ and combinations thereof. More preferably, the effective amount of phospholipid ether analog is a combination of at least two isotopes, one with one with a path range of about 0.1Å to 1 mm and a second with a path range of about 1 mm to 1 m.

Most preferably, the effective amount of phospholipid ether analog is a combination of at least two isotopes, $^{125}I$ and $^{131}I$. Also, preferably, the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl)octadecyl]-2-O-methyl-rac-glycero-3-phosphocholine, wherein iodine is in the form of a radioactive isotope.

In certain embodiments, the effective amount of phospholipid ether analog is fractionated. In yet other embodiments, the effective amount of phospholipid ether analog is about 0.5 μCi to about 3Ci treatable in a linear and dose dependent manner. Other embodiments provide that the dosage is adaptable to the cancer-volume. Yet other embodiments provide that the dosage for radiation insensitive tumor is greater than dosage for radiation sensitive tumor and less than 3Ci and is adaptable to the cancer-volume.

Another embodiment of the present invention provides the use of phospholipid ether analog for the production of a pharmaceutical composition for the treatment of recurrence of cancer, radiation and chemo insensitive cancer or metastasis of cancer. In this embodiment, the phospholipid analog is selected from:

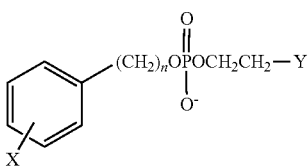

where X is selected from the group consisting of radioactive isotopes of halogen; n is an integer between 8 and 30; and Y is selected from the group comprising $NH_2$, $N(R)_2$, and $N(R)_3$, wherein R is an alkyl or arylalkyl substituent or

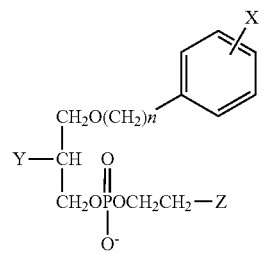

where X is a radioactive isotope of halogen; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. Also in this embodiment, preferably X is selected from the group of radioactive halogen isotopes consisting of $^{18}F$, $^{36}Cl$, $^{76}Br$, $^{77}Br$, $^{82}Br$, $^{122}I$, $^{123}I$, $^{124}I$, $^{125}I$, $^{131}I$, $^{211}At$ and combinations thereof.

Also preferably, the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl)octadecyl]-2-O-methyl-rac-glycero-3-phosphocholine, wherein iodine is in the form of a radioactive isotope.

Further objects, features and advantages of the invention will be apparent from the following detailed description, drawings and appended claims.

BRIEF DESCRIPTION OF DRAWINGS

FIG. 8. PC3 human prostate cancer model implanted into SCID mouse. PC3 is known to be radiation insensitive. The curves between control (no radioactivity, cold NM404) and treatment (I-125-NM404) only separate about 4-5 weeks after treatment, until then the growth of the tumors looks the same indicating that: 1) NM404 takes a few days to about 1 week to fully accumulate in the tumor, and 2) the isotope 1-125 has a low radiation flow (since it has a long half life). Both factors contribute to a delayed onset of the therapy effect, at a time when all NM404 has cleared out of normal tissues.

FIG. 9. Scintigraphic comparison of NM404 (bottom panel) and NM324 (top panel) at 1, 2, and 4 days in a SCID mouse with human prostate PC-3 tumor (arrow) implanted in the flank. Liver and background radioactivity are much improved with NM404.

I. General Description of the Invention

Figure 1:
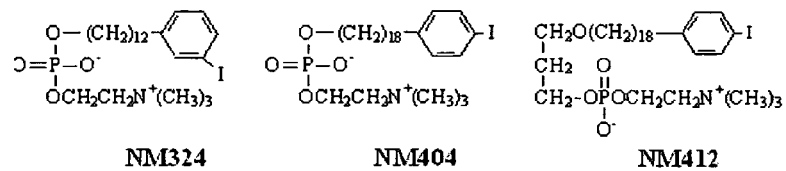
FIG. 1. Structures of certain PLE analogs

General Description of the Invention: Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to optical isomers and analogs, structural isomers and analogs, conformational isomers and analogs, and the like. In one embodiment, this invention encompasses the use of different optical isomers of an anti-tumor compound of Formula 3A. It will be appreciated by those skilled in the art that the anti-tumor compounds useful in the present invention may contain at least one chiral center. Accordingly, the compounds used in the methods of the present invention may exist in, and be isolated in, optically-active or racemic forms. Some compounds may also exhibit polymorphism.

It is to be understood that the present invention may encompass the use of any racemic, optically-active, polymorphic, or stereoisomeric form, or mixtures thereof, which form possesses properties useful in the treatment of tumor-related conditions described and claimed herein. In one embodiment, the anti-tumor compounds may include pure (R)-isomers. In another embodiment, the anti-tumor compounds may include pure (S)-isomers. In another embodiment, the compounds may include a mixture of the (R) and the (S) isomers. In another embodiment, the compounds may include a racemic mixture comprising both (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also he prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes method utilizing derivatives of the anti-tumor compounds. The term "derivatives" includes but is not limited to ether derivatives, acid derivatives, amide derivatives, ester derivatives and the like. In addition, this invention further includes methods utilizing hydrates of the anti-tumor compounds. The term "hydrate" includes but is not limited to hemihydrate, monohydrate, dihydrate, trihydrate and the like.

This invention further includes methods of utilizing metabolites of the anti-tumor compounds. The term "metabolite" means any substance produced from another substance by metabolism or a metabolic process.

As defined herein, "contacting" means that the anti-tumor compound used in the present invention is introduced into a sample containing the receptor in a test tube, flask, tissue culture, chip, array, plate, microplate, capillary, or the like, and incubated at a temperature and time sufficient to permit binding of the anti-tumor compound to a receptor. Methods for contacting the samples with the anti-tumor compound or other specific binding components are known to those skilled in the art and may be selected depending on the type of assay protocol to be run. Incubation methods are also standard and are known to those skilled in the art.

In another embodiment, the term "contacting" means that the anti-tumor compound used in the present invention is introduced into a patient receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-tumor phospholipid ether compound. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-tumor substance using a phospholipid ether compound or (2) is susceptible to a disorder that is preventable by administering the anti-tumor compound using a phospholipid ether compound As used herein, "pharmaceutical composition" means therapeutically effective amounts of the anti-tumor compound having radioactivity together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of disease (e.g., pancreatic cancer, breast cancer); and (b) the reversal or stabilization of such disease. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCI, acetate, phosphate), pH and ionic strength, additives such as albumin or gelatin to prevent absorption to surfaces, detergents (e.g., Tween (Polysorbate) 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, tansdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1 M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp.115-138 (1984). Other controlled release systems are discussed in the review by Langer (Science 249:1527-1533 (1990).

The pharmaceutical preparation can comprise the anti-tumor compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-tumor compound can be administered to a patient by, for example, subcutaneous implantation of a pellet. In a further embodiment, a pellet provides for controlled release of anti-tumor compound over a period of time. The preparation can also be administered by intravenous, intra-arterial, or intramuscular injection of a liquid preparation oral administration of a liquid or solid preparation, or by topical application. Administration can also be accomplished by use of a rectal suppository or a urethral suppository.

The pharmaceutical preparations administerable by the invention can be prepared by known dissolving, mixing, granulating, or tablet-forming processes. For oral administration, the anti-tumor compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the anti-tumor compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-tumor compounds or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler(eds.), Liss, N.Y., pp. 353-365 (1989); Lopez-Berestein ibid., pp. 317-327; see generally ibid).

For use in medicine, the salts of the anti-tumor compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Generally, phospholipids ether compounds and specially NM404 is a promising new tumor-selective diagnostic imaging agent to monitor the treatment response of several tumor treatment modalities. Radioiodinated NM404, a second-generation phospholipid ether analog, had displayed remarkable tumor selectivity in 27/27 tumor models. Due to a lack of metabolic phospholipase enzymes in the membranes of tumor cells, the prevailing hypothesis of this approach is that phospholipid ether analogs become trapped exclusively in tumor cell membranes because of their inability to become metabolized and eliminated. Thus, the differential clearance rates of phospholipid ethers from normal cells versus viable tumor cells form the basis of this concept. Results obtained in a variety tumor models indicate that NM404 is sequestered and selectively retained by viable tumor cells and localizes in both primary and metastatic lesions regardless of anatomic location including those found in lymph nodes. Unlike FDG, this agent does not localize in infectious sites. Other advantages of NM404 over FDG include the following: NM404 is selective for and retained indefinitely by malignant tumor cells whereas FDG in not selective for tumor cells and goes to infectious sites and hyperplasias (Barret's Esophagus). Further, since $^{124}$I has a 4 day physical half life it can be shipped anywhere in the world whereas FDG with its 110 min half-life, may have limited distribution within 200 miles of the production site. NM404 undergoes prolonged retention (not metabolized) and therefore affords a significant therapeutic potential when mated with an appropriate radioisotope like $^{131}$I whereas FDG does not possess any therapeutic potential. NM404 can be labeled with a variety of iodine isotopes expanding it versatility (diagnosis and therapy as well as a tool for experimental animal studies) whereas FDG is limited to $^{18}$F for PET scanning or potentially $^{19}$F (stable) for magnetic resonance imaging albeit at very low sensitivity levels. Regardless of its tumor targeting ability, due to its rapid metabolism in tumor cells, it has not potential for therapy. NM404 affords the potential to not only accurately predict local tumor response to various treatment modalities, but also allows detection of distant metastatic lesions in cases of subtherapeutic primary tumor treatment.

The PLE compounds may be designed to more accurately estimate the specificity and sensitivity of radiolabeled PLE analogs such as NM404 as an imaging agent in prostate cancer and other cancers. Based upon preclinical models, PLE analogs such as NM404 are likely to exhibit high uptake in tumors giving this agent the significant potential for use in staging, following response to therapy, or potentially as a therapeutic agent when coupled with higher doses of $^{131}$I, $^{125}$I, or $^{211}$At an alpha-emitting halogen with therapeutic efficacy.

II. Preferred Embodiments

The present invention generally provides methods and techniques for the detection and treatment of various cancers. The present invention provides a method for detecting and locating recurrence of cancer, radiation and chemo insensitive cancer or metastasis of cancer selected from the group consisting of Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer and Pancreatic cancer in subject that has or is suspected of having cancer. The method comprising the steps of: (a) administering a phospholipid ether analog to the subject; and
(b) determining whether an organ suspected of having recurrence of cancer, radiation insensitive cancer or metastasis of cancer in the subject retains a higher level of the analog than surrounding region(s) wherein a higher retention region indicates detection and location of the recurrence of cancer, radiation and chemo insensitive cancer or metastasis of cancer.

In a preferred embodiment, the phospholipid analog is selected from:

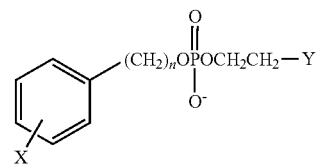

where X is selected from the group consisting of radioactive halogen isotopes; n is an integer between 8 and 30; and Y is selected from the group comprising $NH_2$, $N(R)_2$, and $N(R)_3$, wherein R is an alkyl or arylalkyl substituent or

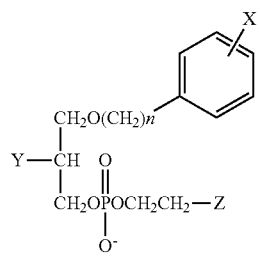

where X is a radioactive halogen isotope; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. Further, in certain embodiments, X is selected from the group of radioactive halogen isotopes consisting of $^{18}F$, $_{36}Cl$, $^{76}Br$, $^{77}Br$, $^{82}Br$, $^{122}I$, $^{123}I$, $^{124}I$, $^{125}I$, $^{131}I$ and $^{211}At$. More preferably, the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl) octadecyl]-2-O-methyl-rac-glycero-3-phosphocholine, wherein iodine is in the form of a radioactive isotope. In this method, preferably the detection is carried out by PET CT MRI scanning methods and combination thereof.

As used herein "alkyl" group refers to a straight chain, branched or cyclic, saturated or unsaturated aliphatic hydrocarbons. The alkyl group has 1-16 carbons, and may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. A "hydroxy" group refers to an OH group. An "alkoxy" group refers to an —O—alkyl group wherein alkyl is as defined above. A "thio" group refers to an —SH group. A "thioalkyl" group refers to an —SR group wherein R is alkyl as defined above. An "amino" group refers to an —$NH_2$ group. An "alkylamino" group refers to an —NHR group wherein R is alkyl is as defined above. A "dialkylamino" group refers to an —NRR' group wherein R and R' are all as defined above. An "amido" group refers to an —$CONH_2$. An "alkylamido" group refers to an —CONHR group wherein R is alkyl is as defined above. A "dialkylamido" group refers to an —CONRR' group wherein R and R' are alkyl as defined above. A "nitro" group refers to an $NO_2$ group. A "carboxyl" group refers to a COOH group.

As used herein, "aryl" includes both carbocyclic and heterocyclic aromatic rings, both monocyclic and fused polycyclic, where the aromatic rings can be 5- or 6-membered rings. Representative monocyclic aryl groups include, but are not limited to, phenyl, furanyl, pyrrolyl, thienyl, pyridinyl, pyrimidinyl, oxazolyl, isoxazolyl, pyrazolyl, imidazolyl, thiazolyl, isothiazolyl and the like. Fused polycyclic aryl groups are those aromatic groups that include a 5- or 6-membered aromatic or heteroaromatic ring as one or more rings in a fused ring system. Representative fused polycyclic aryl groups include naphthalene, anthracene, indolizine, indole, isoindole, benzofuran, benzothiophene, indazole, benzimidazole, benzthiazole, purine, quinoline, isoquinoline, cinnoline, phthalazine, quinazoline, quinoxaline, 1,8-naphthyridine, pteridine, carbazole, acridine, phenazine, phenothiazine, phenoxazine, and azulene. Further, as used herein "arylalkyl" refers to moieties, such as benzyl, wherein an aromatic is linked to an alkyl group which is linked to the indicated position in the PLE compound.

Another embodiment of the present invention provides a method for the treatment of recurrence of cancer, radiation and chemo insensitive cancer or metastasis of cancer in a subject. The method comprises administering to the subject an effective amount of a compound comprising a phospholipid ether analog. In a preferred embodiment, the recurrence of cancer, radiation and chemo insensitive cancer or metastasis of cancer occurs in the group selected from Lung cancer, Adrenal cancer, Melanoma, Colon cancer, Colorectal cancer, Ovarian cancer, Prostate cancer, Liver cancer, Subcutaneous cancer, Squamous cell cancer, Intestinal cancer, Hepatocellular carcinoma, Retinoblastoma, Cervical cancer, Glioma, Breast cancer, Pancreatic cancer and Carcinosarcoma. Also preferably, the phospholipid analog is selected from:

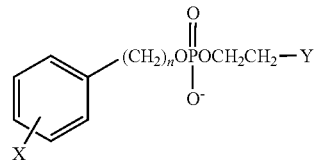

where X is selected from the group consisting of radioactive halogen isotopes halogen; n is an integer between 8 and 30; and Y is selected from the group comprising $NH_2$, $N(R)_2$, and $N(R)_3$, wherein R is an alkyl or arylalkyl substituent or

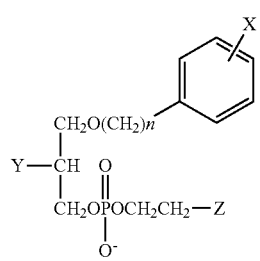

where X is a radioactive halogen isotope; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. In this method, preferably, X is selected from the group of radioactive halogen isotopes consisting of $^{18}F$, $^{38}Cl$, $^{78}Br$, $^{77}Br$, $^{82}Br$, $^{122}I$, $^{123}I$, $^{124}I$, $^{125}I$, $^{131}I$, $^{211}At$ and combinations thereof. More preferably, the effective amount of phospholipid ether analog is a combination of at least two isotopes, one with a path range of about 0.1Å to 1 mm and a second with a path range of about 1 mm to 1 m, also as discussed in FIG. 2.

Most preferably, the effective amount of phospholipid ether analog is a combination of at least two isotopes, 125I and 131I Also, preferably, the phospholipid ether is 18-(p-Iodophenyl)octadecyl phosphocholine, 1 -O-[18-(p-Iodophenyl)octadecyl]-1,3-propanediol-3-phosphocholine, or 1 -O-[18-(p-Iodophenyl)octadecyl]-2-O-methyl-rac-glycero-3-phosphocholine, wherein iodine is in the form of a radioactive isotope.

Figure 11:
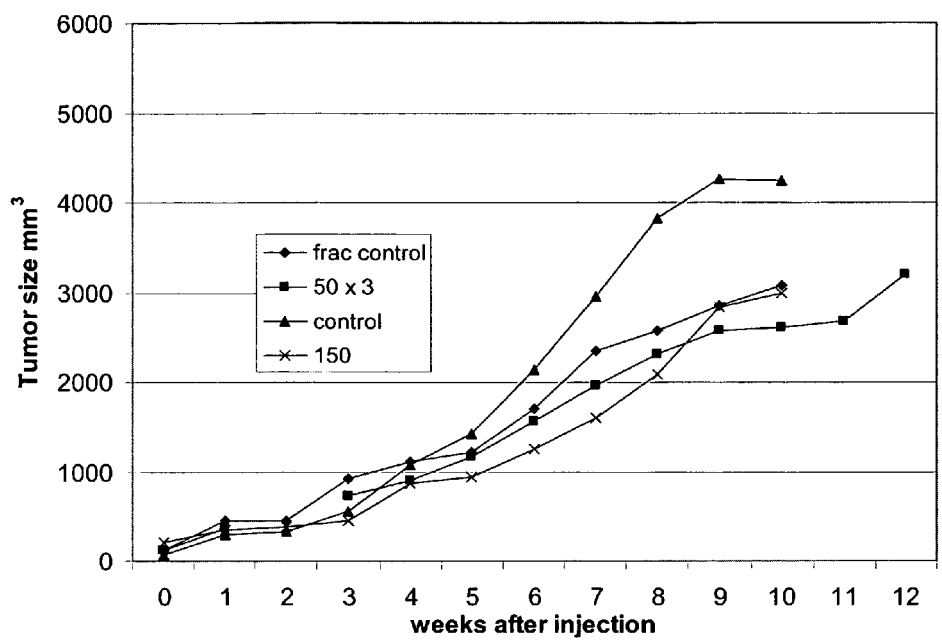
FIG. 11. A549 Tumor Xenografts ($1 \times 10^6$ cells, s.c.) in Female SCID Mice Fractionated Dose (3×50 mCi), having 2 independent controls for each dosage. A fractionated dosing of NM404 (e.g. 3×50 micro-Ci versus a single dose of 150 micro-Ci) produced the same therapy effect. The fractionated dose may be safer since it is eliminated from normal tissues in between fractionated injections.

As shown in FIG. 11 in certain embodiments, the effective amount of phospholipid ether analog is fractionated. The advantage of using fractionated dosage is that it allows for the PLE analog to be removed from normal tissues. As an example, fractionated dosing of NM404 (e.g. 3×50 micro-Ci versus a single dose of 150 micro-Ci) produced the same therapy effect, while still providing low doses of compounds which is then eliminated from normal tissues in between fractionated injections.

Figure 10:
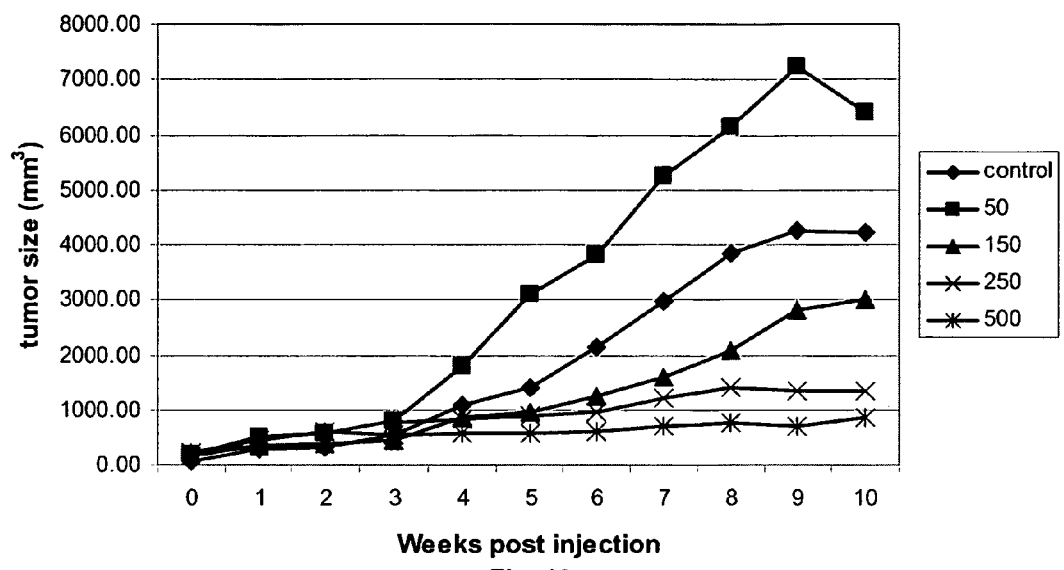
FIG. 10. Tumor volume for each group was recorded over the 10-week assessment period depicting the control and dosage of 50, 150, 250 and 500 µCi. In this figure, control animals show rapidly growing tumors over the 10-week assessment period. This confirms that the compound itself C-NM404 has no substantial effect on tumors growth. The 50 µCi dose group did not show any difference to control animals, hence these seem to be ineffective dose levels in this animal model. However, the 150, 250 and 500 µCi dose groups show a substantial and prolonged treatment effect. Tumor volumes are stable and same tumors appear "collapsed" (the tumor surface has caved in). Additionally, hair above the tumors fell off confirming substantial accumulation of radioactivity in these tumors. The results show a dose-linear effect of I-125-NM404 on tumor volume.
Figure 12:
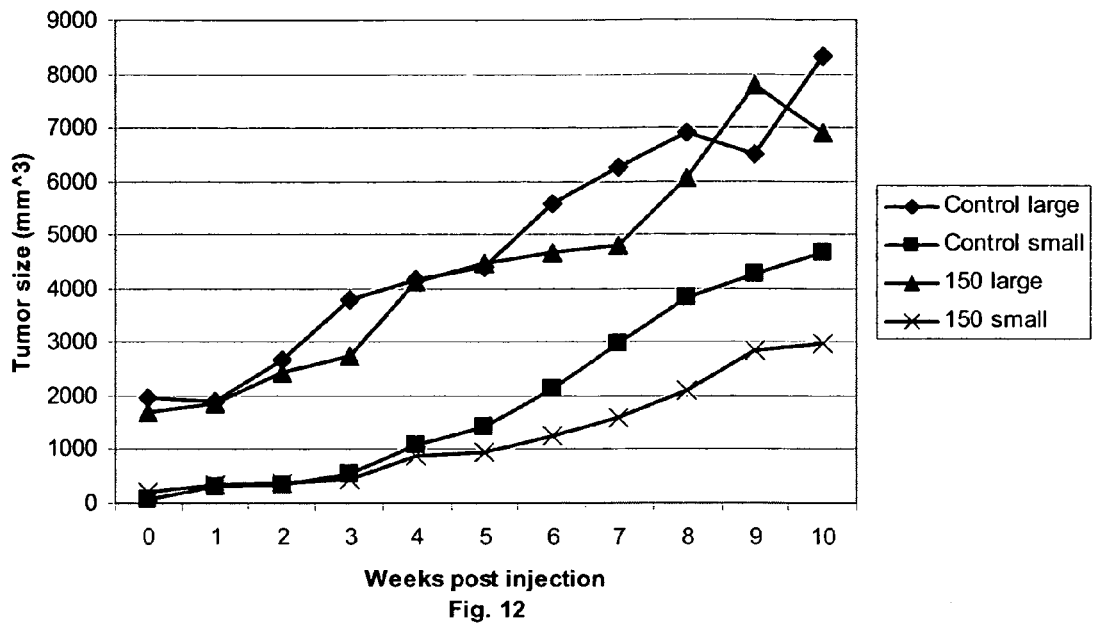
FIG. 12. A549 Large Tumors vs Small Tumors 150 microcuries
Figure 13:
FIG. 13. Bioscan image (A) obtained 4 days post $^{125}$I-NM404 injection into an Apc$^{Min}$ mouse. Digital photo (B) and positionally matched fused image (C) of excised mouse lung containing spontaneous lung tumor (2 mm dia, arrow) showing intense uptake of NM404 into the tumor.

In yet other embodiments, the effective amount of phospholipid ether analog is about 0.5 μCi to about 500 mCi, and as shown in FIG. 10, this is treatable in a linear and dose dependent manner. Other embodiments provide that the dosage is adaptable to the cancer-volume as shown in FIG. 12. The graph in FIG. 12 shows the difference in tumor growth for the same dose of I-125-NM404 (150 microCi) when injecting in animals with small (<1 cm) and large tumors (>1 cm).

The results show that a small tumor showed stunned tumor growth with that dose, however a large tumor population did not show any effects for the same dose, basically behaving like non-radiated control. The graph in FIG. 12 further illustrates is that the effective tumor dose should be adjusted to tumor volume and that there is a tumor dose per volume of tumor volume that has to be achieved in order to show efficacy.

Yet other embodiments provide that the dosage for radiation and chemo insensitive tumor is greater than dosage for radiation sensitive tumor and less than 500 mCi and is adaptable to the cancer-volume, as ascertainable by comparing PC3 (FIG. 8) and A549 cancer models (FIG. 10, 11 and 12), in which PC3 model is radiation insensitive.

Another embodiment of the present invention provides the use of phospholipid ether analog for the production of a pharmaceutical composition for the treatment of recurrence of cancer, radiation and chemo insensitive cancer or metastasis of cancer. In this embodiment, the phospholipid analog is selected from:

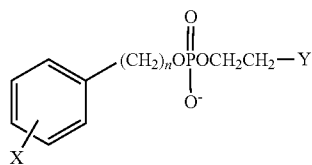

where X is selected from the group consisting of radioactive halogen isotopes; n is an integer between 8 and 30; and Y is selected from the group comprising $NH_2$, $N(R)_2$, and $N(R)_3$, wherein R is an alkyl or arylalkyl substituent or

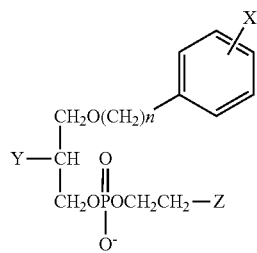

where X is a radioactive halogen isotope; n is an integer between 8 and 30; Y is selected from the group consisting of H, OH, COOH, COOR and OR, and Z is selected from the group consisting of $NH_2$, $N(R)_2$, and $N(R)_3$, wherein R is an alkyl or arylalkyl substituent. Also in this embodiment, preferably X is selected from the group of radioactive halogen isotopes consisting of $^{18}F$, $^{36}Cl$, $^{76}Br$, $^{77}Br$, $^{82}Br$, $^{122}I$, $^{123}I$, $^{124}I$, $^{125}I$, $^{131}I$, $^{211}At$ and combinations thereof.

Also preferably, the phospholipid ether is 18-(p-Iodophenyl)octadecyl phosphocholine, 1-O-[18-(p-Iodophenyl)octadecyl]-1,3-propanediol-3-phosphocholine, or 1-O-[18-(p-Iodophenyl)octadecyl]-2-O-methyl-rac-glycero-3-phosphocholine, wherein iodine is in the form of a radioactive isotope.

Synthesis and Structure Activity Relationship Effects on the Tumor Avidity of Radioiodinated Phospholipid Ether Analogs Radioiodinated phospholipid ether analogs have shown a remarkable ability to selectively accumulate in a variety of human and animal tumors in xenograft and spontaneous tumor rodent models. It is believed that this tumor avidity arises as a consequence of metabolic differences between tumor and corresponding normal tissues. The results of this study indicate that one factor in the tumor retention of these compounds in tumors is the length of the alkyl chain that determines their hydrophobic properties. Decreasing the chain length from C12 to C7 resulted in little or no tumor accumulation and rapid clearance of the compound in tumor-bearing rats within 24 hours of administration. Increasing the chain length had the opposite effect, with the C15 and C18 analogs displaying delayed plasma clearance and enhanced tumor uptake and retention in tumor-bearing rats. Tumor uptake displayed by propanediol analogs NM-412 and NM-413 was accompanied by high levels of liver and abdominal radioactivity 24 hours post injection to tumor bearing rats. Addition of a 2-O-methyl moiety to the propanediol backbone also retarded tumor uptake significantly. A direct comparison between NM-404 and its predecessor, NM-324, in human PC-3 tumor bearing immune-compromised mice, revealed a dramatic enhancement in both tumor uptake and total body elimination of NM-404 relative to NM-324. Based on imaging and tissue distribution studies in several rodent tumor models, the C18 analog, NM-404, was chosen for follow-up evaluation in human lung cancer patients. Preliminary results have been extremely promising in that selective uptake and retention of the agent in tumors is accompanied by rapid clearance of background radioactivity from normal tissues, especially those in the abdomen. These results strongly suggest that extension of the human trials to include other cancers is warranted, especially when NM-404 is radiolabeled with iodine-124, a new commercially available positron-emitting isotope. The relatively long physical half-life of 4 days afforded by this isotope appears well suited to the pharmacodynamic profile of NM-404.

Chemical Synthesis. In the course of synthesis of iodinated phospholipid ether analogs the inventors sought to develop a general synthetic scheme which would allow altering the chain length in the target compounds. The synthetic approach was based on the copper catalyzed cross-coupling reaction of Grignard reagents with alkyl tosylates or halides[15] (Schemes 1, 2). The choice of the building blocks for alkyl chain elongation was dictated by the commercial availability of starting materials.

Scheme 1: Reagents and conditions: (a) $Me_3SiBr$, $CH_2Cl_2$; (b) $BrMg(CH_2)_{11}OTHP$, $Li_2CuCl_4$ (cat), THF, −78 to 20° C.; (c) PPTS, EtOH, 40° C.; (d) TsCl, DMAP, $CH_2Cl_2$; (e) BrMg $(CH_2)_3OTHP$, $Li_2CuCl_4$ (cat), THF, −78 to 20° C.; (g) BrMg $(CH_2)_6OTHP$, $Li_2CuCl_4$ (cat), THF, −78 to 20° C.

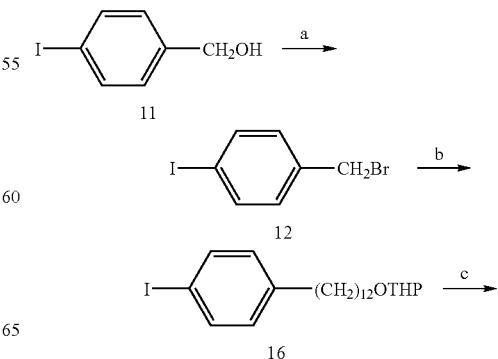

Scheme 1

-continued

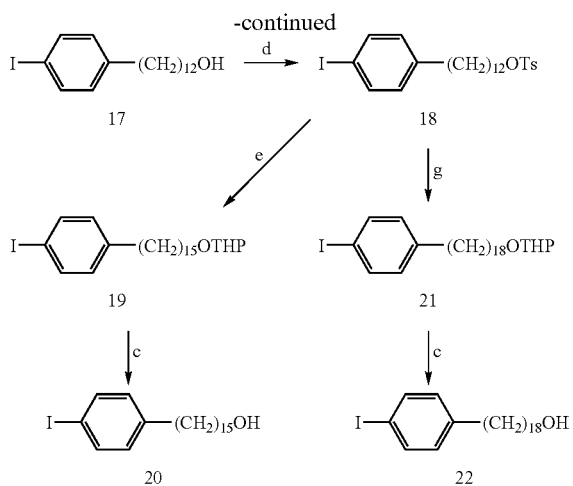

The synthesis was initiated by the conversion of p-iodobenzyl alcohol 11 to p-iodobenzyl bromide 12 as shown in Scheme 1. p-Iodobenzyl bromide was further coupled with Grignard reagent derived from THP protected 11-bromoundecanol 13 in the presence of 0.5-0.7 mol % of $Li_2CuCl_4$. 12-(p-Iodophenyl)dodecanol 17 obtained after deprotection of the first coupling product 16 was used for the synthesis of C12 iodinated phospholipids as described earlier.[12,13] Alcohol 17 also served as a starting material for the synthesis of ω-iodophenyl alkanols with longer chains. For example, coupling of the tosylate 18 with Grignard reagents made from bromides 14 and 15 followed by THP deprotection furnished the C15 (20) and C18 (22) alcohols, respectively. These alcohols were converted into corresponding alkylphosphocholines 5 (NM-397) and 6 (NM-404) according to published procedures.[12,13] Propanediol phospholipid ethers 7 (NM-413) and 8 (NM-412) were synthesized from 3-benzyloxypropanol 25, and 2-0-methyl-rac-glycerol phospholipid ethers 9 (NM-414) and 10 (NM-410) were obtained from 1-Obenzyl-2-0-methyl-rac-glycerol 26 using a sequence of reactions the inventors had previously reported. Radiolabeling with iodine-125 was accomplished by an isotope exchange method routinely employed in the laboratory.

Scheme 2:

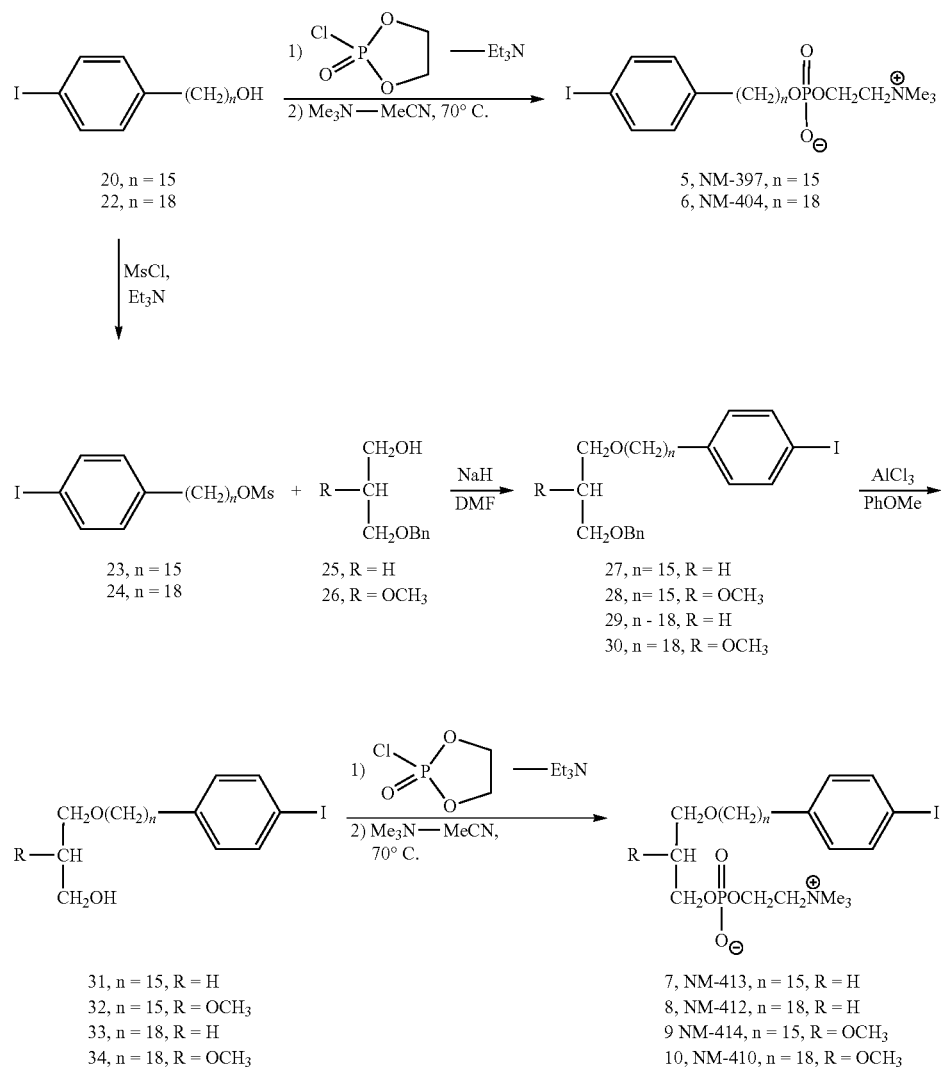

Biology. The avidity of PLE analogs to localize in tumors was evaluated in several animal models. The PC-3 model represents a human tumor cell line that was used to determine the target (tumor) to non-target ratio of NM404 and NM412 in head to head comparison in order to select a candidate for an initial human pharmacokinetic trial in prostate cancer patients. The MatLyLu (Dunning R3327 rat) model, a rat prostate tumor line, was used specifically to screen 9 specific analogs prior to entering them into control for dosimetry and tumor-bearing animals for determining tumor/background ratios. Finally, the Walker-256 carcinosarcoma model was used for quantitative tissue distribution purposes.

In order to expedite the screening process and minimize the number of tumor bearing animals utilized in multiple time point tissue distribution studies, new radioiodinated homologs were imaged by gamma camera scintigraphy in the rat Dunning R3337 (MAT LyLu strain) prostate cancer model. Thus, male Copenhagen rats received subcutaneous injection of MAT LyLu cells ($1 \times 10^6$ cells) in the thigh 10-14 days prior to injection of the radioiodinated PLE analogs (30-40 µCi) in 2% Tween-20 solution. Gamma camera images were obtained at multiple time points including 24 and 48 hours post injection. Homologs (NM-410, NM-413, and NM-414) displaying high hepatic uptake, significant abdominal accumulation and retention or poor tumor uptake and retention were not submitted to subsequent biodistribution analysis. Tissue distribution of radioactivity in rats bearing Walker-256 carcinosarcoma was assessed at various time intervals following intravenous administration of the radio-iodinated chain length homologs. The first group of compounds that was tested included three alkylphosphocholines: a shorter chain analog with seven carbons 3 (NM-396) and two analogs with a longer chain length, 5 (NM-397, C15 alkyl chain length) and 6 (NM-404, C18 alkyl chain length).

Initial biodistribution experiments performed with 3 (NM-396, C7 analog) indicated rapid tissue clearance accompanied by significant in vivo deiodination. By 24 hours, the amount of radioactivity in the thyroid was 213% ID/g, whereas levels of radioactivity in all of the organs surveyed was <0.10% ID/g. As follows from these studies, reducing the number of methylene groups to seven apparently afforded a much more hydrophilic molecule which was rapidly excreted by the kidneys. In contrast to compound 4 (NM-346, the C12 analog), the C7 analog 3 cleared rapidly from the rat and did not localize in tumor tissue at any of the time points examined.

This observation directed the future efforts to assessing the effect of increasing the length of the aliphatic chain upon tumor uptake and retention. The tissue distribution of the C15 homolog 5 (NM-397) was assessed utilizing the same Walker 256 rat tumor model. Radioactivity in the tumor increased with time and peaked at 48 hours after administration (1.65±0.23% of ID/g) as opposed to most normal tissues which exhibited their highest levels of radioactivity 6 hours after administration. With the exception of thyroid, the tumor had higher radioactivity concentrations at 24, 48, and 120 hours than any of the other tissues surveyed. A more rapid washout of radioactivity occurred in the normal tissues as compared to the tumor presumably due to metabolism and elimination by normal tissues. The accumulation of radioactivity in the thyroid increased throughout the course of the study suggesting the presence of a low level of in vivo deiodination. Levels of radioactivity in the duodenum were similar to those of tumor with maximum levels being observed at 48 hours after administration (1.38±0.24% ID/g).

Although limited results were obtained with the C12 analog 4 (NM-346) in this model, results suggest that the tissue distribution profile of the C15 analog 5 (NM-397) was similar to that observed with the C12 analog 4 with the exception of a 2-fold increase in tumor uptake at 24 h. Remaining uptake and clearance in other organs and tissues was similar between the two compounds.

The effect of further extending the aliphatic chain to the C18 analog 6 (NM-404) depicted a dynamic profile of this compound that was similar to the C15 analog 5 (NM-397) as levels of radioactivity peaked in the tumor 48 hours after administration (1.14±0.01 % of ID/g), albeit at slightly lower levels. Quantities of radioactivity detected in liver, kidney and duodenum were significantly lower following administration of the C18 compound 6 as compared to the same organs in the C15 analog 5 studies. In addition, the C18 analog 6 was retained in the circulation to a much greater extent than the other chain length homologs surveyed. For example, at 120 hours, blood levels for 6 were 0.6±0.1% of ID/g as compared to levels of 0.07±0.00% of ID/g for the C15 (5) analog. Total radioactivity levels in the thyroid were relatively low in both 5 and 6 when the extremely small mass of the gland is considered.

In order to examine the transport properties of PLE analogs, plasma was isolated from Walker-256 tumor-bearing rats 7 days after administration of iodine-125 labeled 6. The distribution of radioactivity in the plasma compartment of a rat receiving 6 (NM-404) was studied. PAGE analysis revealed that most of the circulating radioactivity (88%) was associated with the albumin fraction following administration of the C18 analog 6. This finding is similar to results reported by Eibl who studied binding of phospholipid ether prototype, ET-18-OCH$_3$, with serum proteins and found that the majority of the ether lipid (71%) was bound to albumin and about 6% to HDL.

Comparative Imaging Studies. Gamma camera scintigraphy images shown in FIG. 19 directly compare the tumor uptake and body clearance of second generation analog $^{125}$I-NM-404 (6) versus its shorter chain, first generation predecessor, $^{125}$I-NM-324 (2) at 1, 2, and 4 days post administration in immune-compromised SCID mice bearing human PC-3 prostate tumor xenografts. Qualitative scintigraphic comparison of these two PLE analogs demonstrated a striking difference in tumor uptake and overall body clearance. The longer chain agent, NM-404, displays rapid tumor uptake and prolonged retention accompanied by rapid whole body elimination of radioactivity, whereas tumor uptake and body clearance are substantially delayed with NM-324, even at 4 days following administration. Significant tumor uptake and retention of C18 analog NM-404 accompanied by rapid whole body elimination clearly defined the superior imaging properties of NM-404 in this model.

Extensive quantitative tissue distribution results obtained at 1, 3, 5, and 8 days following administration of radioiodinated NM-404 in this model indicated rapid elimination of radioactivity from all normal tissues over the 8 day evaluation period. Tumor uptake, however, continued to increase up until day 5 when it reached 18% injected dose per gram of tumor. Tumor to background tissue ratios steadily increased over the course of the experiment due to prolonged retention in tumors coupled with a steady elimination from normal tissues. Tumor to background tissue ratios exceeded 4, 6.8, 23, and 9 in blood, liver, muscle, and prostate, respectively, 3 days after injection and continued to improve at 5 and 8 days. Again, although thyroid levels ranged from 26 to 54% injected dose per gram of tissue, these levels are actually quite low and represent an extremely small percentage of the injected dose when the exceedingly small mass of the organ is considered and the data are presented on a percent administered dose per organ basis.

Kötting et al have investigated the effects of alkyl chain length on the biodistribution of three alkyl phosphocholine (APC) analogs. The Kötting study differed from the experiments in that 1) compounds were orally administered at concentrations thought to be cytotoxic to tumor, and 2) the C22 compound contained a double bond in the alkyl chain. Therefore direct comparisons with the work described herein cannot be made due to large dose differences and the unknown bioavailability of the oral agents. In the Kötting study, C16, C18 and C22 analogs were administered orally to rats bearing a methyinitrosourea-induced mammary carcinoma in daily doses of 50-120 ∝mol/kg. As alkyl chain length increased, the observed levels of compound in kidney, liver, and lung decreased. In contrast to the tracer results obtained with the radioiodinated PLE analogs, Kötting and coworkers found that levels of APC in blood decreased with increasing chain length, while tumor levels increased with increasing chain length.[19] It would be expected that oral administration would result in a substantial amount of degradation of the ether lipids in the GI tract prior to absorption.

Tumors were readily visualized with the C12 (4), C15 (5) and C18 (6) alkyl phosphocholine homologs via gamma camera scintigraphy at both 24 and 48 hours after injection. Rat imaging results obtained with C15 (7, NM-413) and C18 (8, NM-412) propanediol analogs, on the other hand, displayed tumor uptake accompanied by high liver and abdominal radioactivity levels. Imaging results obtained with C15 (9, NM-414) and C18 (10, NM-410) 2-O-Me glycerol analogs in the MAT LyLu prostate model indicated high radioactivity levels in the liver and abdomen with little to no uptake of the agent into tumors. The differences in the clearance and quantity of radioactivity from non-target tissues including the liver and intestinal tract will have significant impact upon the application of radioiodinated phospholipid ether analogs as imaging agents in humans. Non-target tissue uptake can decrease the efficacy of radiodiagnostic imaging by creating high background activity or by causing excessive exposure of radiosensitive tissues to the injected radioactivity. A preliminary clinical trial with 2 (NM-324, the meta-iodo isomer of NM-346) in cancer patients, while affording excellent tumor uptake, was limited by the radiation dosimetry associated with accumulation in non-target tissues including liver, kidneys, and bladder.

The strategy was to examine the alkyl portion of phospholipid ether analog structure and determine its role in tumor localization and retention. Qualitative rat whole body screening scans acquired in MAT-LyLu tumor bearing rats with radioiodinated PLE analogs with longer chain lengths revealed sufficient tumor uptake to permit detection. However, follow-up tissue distribution studies have shown that sequential increases in the chain length from C12 to C15 to C18, resulted in a rapid decline in the amount of radioactivity detected in the non-target organs. This substantial decrease in non-target tissue activity was accompanied by a relatively small reduction in the levels of radioactivity present in the tumor. In addition, the C18 analog 6 (NM-404) displayed a propensity to remain in the circulation much longer than the C12 (4) and C15 (5) analogs. A longer plasma half-life may be expected to result in additional opportunities for uptake of the C18 compound 6 by the tumor as it continually circulated through the vasculature. This extended plasma half-life may be a result of strong binding of the probe to albumin. Uptake and transport of radiolabeled PLE by plasma components may also be an important factor related to the tumor retention of these compounds. Certainly, increase of the chain length from C7 to C18, results in an increase in the lipophilicity of the PLE analogs. Greater lipophilicity may increase the affinity of these compounds for the cell membrane, and may alter their binding to plasma components. Uptake and transport in the circulation by endogenous lipoproteins such as LDL and HDL may also impact the biological distribution into the tumor.

Figure 25:
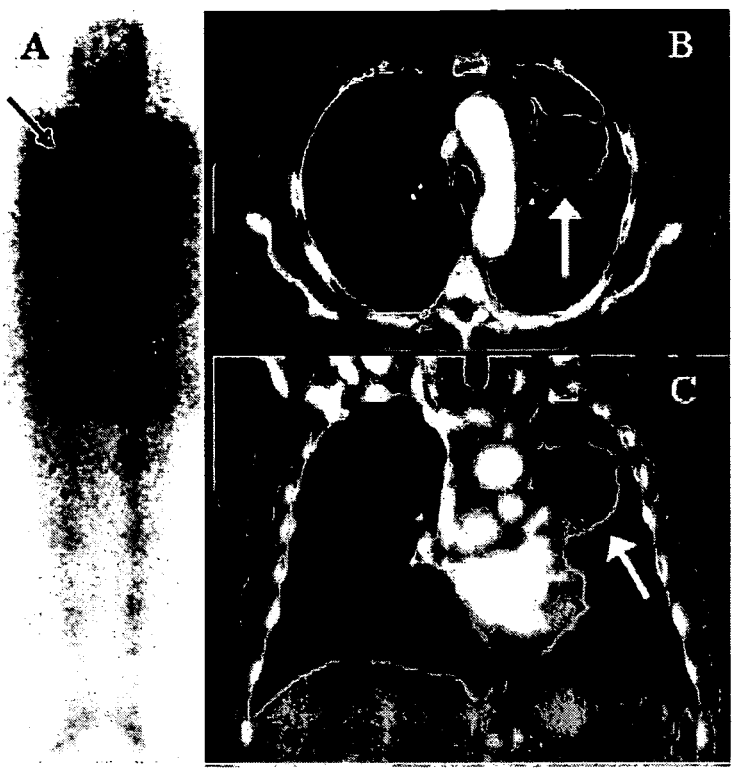
FIG. 25. Posterior whole body planar nuclear medicine image (A) 4 days after iv administration of $^{131}$I-NM-404 (0.8 mCi) to a patient with non small cell lung cancer (6 cm dia., arrow). Lung tumor is easily detected in corresponding axial (B) and coronal (C) computed tomography (CT) scans.

In preparation for human clinical trials, unlabeled NM404 was subjected to independent (University of Buffalo Toxicology Research Center) acute toxicity evaluation at 1200 times the anticipated imaging mass dose in rats and rabbits. The agent was well tolerated and no acute toxicities were found at this dose level. Due to its selective tumor uptake and retention properties in a variety of rodent tumor models and subsequent excellent safety profile in rats and rabbits, NM-404 was selected to undergo initial human pharmacokinetic evaluation in non-small cell lung cancer (NSCLC) patients. Patients underwent planar gamma-camera scintigraphy after receiving an injection of $^{131}$I-NM-404 (<1 mCi). Preliminary human results (n=3) demonstrated tumor uptake and prolonged retention in the primary lung tumors (FIG. 25). Relative to the high liver uptake values observed with its predecessor, NM-324, however, liver and abdominal radioactivity levels were much lower with NM-404, suggesting the feasibility of evaluating this agent in other abdominal tumors including those associated with the colon, prostate, and pancreas.

Conclusions.

In summary, the rationale behind the design of new iodinated PLE analogs described in this paper was exploited in an effort to evaluate the effect of chain length and other structural modifications in the hydrophobic part of the phospholipid molecule on tumor uptake and retention. Decreasing the chain length from C12 to C7 resulted in little or no tumor accumulation and rapid clearance of the compound in tumor-bearing rats by 24 hours after administration. Increasing the chain length had the opposite effect, with the C15 and C18 analogs displaying delayed plasma clearance and enhanced tumor uptake and retention in tumor-bearing rats. Tumor uptake displayed by propanediol analogs 7 and 8 was accompanied by fairly high levels of liver and abdominal radioactivity 24 hours post injection to tumor bearing rats. Addition of a 2-O-methyl moiety in 9 and 10 retarded tumor uptake significantly. A direct comparison between NM-404 and its predecessor, NM-324, in human PC-3 bearing immune-compromised mice, revealed a dramatic enhancement in both tumor uptake and total body elimination of NM-404 relative to NM-324. NM-404 afforded superior imaging properties to the other analogs examined in several animal models, thus warranting further evaluation of this second generation PLE analog in human lung cancer patients. Preliminary clinical results in humans indicated desired tumor uptake and retention properties similar to those seen previously in animal models. In contrast to its shorter chain predecessor NM-324, however, NM-404 displayed significantly lower liver, kidney and abdominal background radioactivity levels, which in addition to providing promise for lung tumor imaging, suggests further evaluation of this agent in human colorectal, pancreatic and prostate cancer patients is warranted. Moreover, a lack of urinary bladder radioactivity, suggests little renal clearance of the agent or its metabolites over the time points examined. This represents a significant advantage over 18F-fluorodeoxyglucose (FDG), a PET agent used routinely for tumor imaging today, which undergoes significant renal elimination, thus prohibiting imaging in the area of the prostate.

Because the tumor-targeting strategy of PLE analogs appears to involve selective tumor retention over time, relatively short-lived nuclides such as $^{18}$F or even $^{99m}$Tc are not practical for labeling NM-404 at the current time. Given the preliminary success of $^{131}$I-NM-404 in the current lung cancer imaging trial, it is now imperative to radiolabel NM-404 with iodine-124, a relatively new positron-emitting isotope with a 4.2-day half-life, and to evaluate its tumor detection efficacy by PET. It has been reported that PET imaging with $^{124}$I affords over 40 times the sensitivity of planar $^{131}$I-gamma imaging. PET, unlike traditional gamma-camera imaging, also offers significant resolution enhancement and 3-dimensional imaging capabilities, as well as superior quantitation properties relative to planar scintigraphic imaging. The long, 4-day physical half-life of this PET isotope is well suited to the tumor uptake and retention kinetics of NM-404 and the inventors are in the process of extending the imaging studies with NM-404 to include PET.

Non-small Cell Lung Cancer (NSCLC)

Phospholipid ether analogs (PLE) molecules have unique biochemical and pharmacological properties resulting in a high degree of tumor selectivity. Unlike FDG, which accumulates non-specifically in both malignant and non-malignant hypermetabolic tissues, the inventors have shown radioiodinated PLE analogs undergo selective retention in a wide variety of murine and human tumors in high levels, and do not accumulate in normal or inflammatory tissues. The family of phospholipids ethers (PLE) are characterized by the presence of an ether-linked long chain alkyl or alkenyl alcohol connected to a glycerophosphocholine molecule ordinarily found in mammalian cells as a minor component of the total phospholipid content. Among the PLE, there are many subtypes, one of the most extensively studied subtypes are structurally simplified alkyl phosphocholines (APC). I-125-NM404, is part of this APC family.

The present invention teaches methodologies for preliminary human PET imaging data regarding the use of the second-generation PLE analog, NM404, in imaging patients with NSCLC. In preclinical models, the inventors have shown that NM404 is (a) selectively retained in 27/27 tumor models, including lung and brain tumors as well as PC-3 prostate bone metastases, (b) is not retained in normal, premalignant, or hyperplastic tissues and, (c) is not retained in inflammatory tissues. In first-in-human pharmacokinetic studies with $^{131}$I-NM404 in patients with NSCLC, the inventors have found that $^{131}$I-NM404 is safe, and that from 24-48 hours is the optimal scintigraphic imaging time point for tumor detection. These studies also revealed significantly lower liver and background activity levels relative to earlier promising analogs and confirmed the agent doesn't cross the intact blood brain barrier.

Although sufficient for early human pharmacokinetic studies, the poor imaging characteristics and planar imaging nature associated with iodine-131 scintigraphy dictate that NM404 be further developed for PET imaging. The inventors have recently radioiodinated NM404 in excellent yield with commercial iodine-124, a relatively new, long-lived PET isotope, the half-life of which appears ideally matched to the pharmacokinetic profile of NM404. Initial microPET scans obtained with $^{124}$I-NM404 in xenograft and spontaneous mouse and rat tumor models confirmed universal tumor avidity and prolonged retention. Extending these results to PET scanning is now necessary in order to accurately characterize and quantitate the in vivo distribution properties of this agent. The primary objective of this proposal is to further develop NM404 for PET/CT imaging in NSCLC patients with this radioisotope.

The present invention studies (a) the efficacy of imaging primary NSCLC tumors with $^{124}$I-NM404 PET/CT in patients with NSCLC undergoing resection, by comparing pre-operative images with pathological findings, (b) the specific tumor accumulation and metabolic fate of NM404 in NSCLC patients undergoing resection, and correlate tumor retention with decreased phospholipase-D activity; (c) preliminary data regarding the sensitivity of imaging locoregional, and metastatic tumors with $^{124}$I-NM404 PET/CT in patients with NSCLC, by comparing these results with FDG PET/CT scanning; and (d) preliminary data regarding the specificity of imaging with $^{124}$I-NM404 PET/CT, by imaging patients who present with solitary pulmonary nodules, or have a diagnosis of pulmonary sarcoidosis or granulomatous infections such as fungal or mycobacterial infections, or bacterial pneumonias.

Due to its prolonged tumor retention properties, $^{125}$I-labeled NM404 has recently afforded significant tumor regression (vide infra) in SCID mice bearing A549 human lung tumor xenografts. Exhibiting both diagnostic and therapeutic utility, NM404 is being developed as a true, potentially universal, diagnostic and therapeutic agent.

Figure 3:
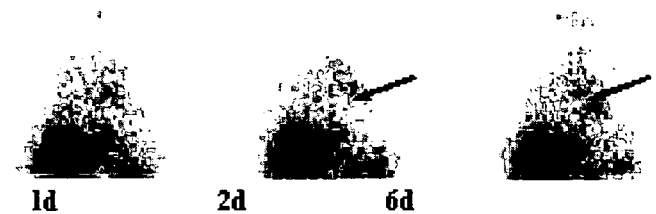
FIG. 3. Scintigraphy of the anterior chest of Patient 03 acquired at 1, 2, and 6 days after iv administration of 1 mCi 131I-NM-324. Uptake is seen in the left lingular lung cancer (T) with increasing tumor-to-background ratios over time.
Figure 14:
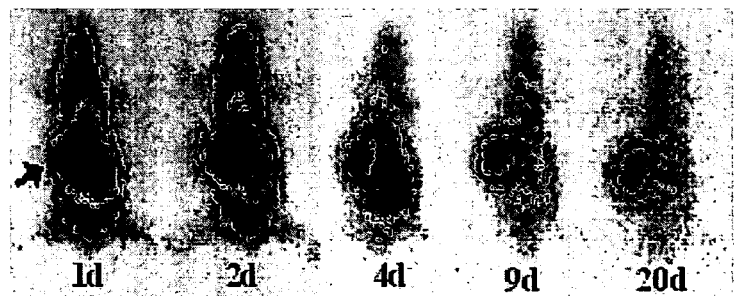
FIG. 14. Time course of $^{125}$I-NM404 in human RL-251 adrenal cancer xenograft in a SCID mouse. Prolonged tumor (1.5×0.5 cm, arrow) retention is evident even after 20 days.

NM404 has now been evaluated in 27 animal tumor models, including several lung, and it is clear that once the agent enters tumor cells, it reaches a metabolic dead end and becomes trapped. Prolonged tumor retention of this agent is demonstrated in a human adrenal tumor xenograft implanted into SCID mice (FIG. 14). NM404 is also retained in spontaneous murine lung tumors (FIG. 1 3). Using $^{125}$I-labeled NM404, the inventors have been able to image mammary and prostate tumors in mice in excess of 60 days. Prolonged tumor retention characteristics may significantly enhance the radiotherapeutic efficacy of the agent. Imaging and tissue distribution studies performed in mouse models aimed at determining the uptake characteristics in a wide variety of tumor models are summarized in Table 2.

Rationale for Isotope Selection for Clinical Studies.

Although the inventors have studied NM404 labeled with iodine-131 in the preliminary human pharmacokinetic studies, this is less than optimal for imaging since iodine-131 scintigraphy produces images with limited resolution and little anatomic detail. The new long-lived isotope iodine-124, however, will produce tomographic PET images which will be displayed with corresponding CT images, thereby providing significantly greater anatomic and functional detail.

Because the tumor-targeting strategy of PLE analogs appears to involve selective tumor retention over time, relatively short-lived nuclides such as $^{18}$F or even $^{99m}$Tc are not practical for labeling NM404 at the current time. Although the use of other isotopes, including iodine-123, may ultimately prove suitable for use with NM404 in certain tumors, the current focus will develop the PET imaging capability of this agent due to the recent success of oncologic imaging using hybrid PET-CT scanners. The unsurpassed diagnostic accuracy afforded by a biochemical or functional tumor imaging PET agent combined with the precise anatomic accuracy provided by CT is now the gold standard for tumor imaging. However, it is highly advantageous to label PLE analogs with iodine-124, a relatively new PET isotope, wherein the physical half-life (4 days) matches well with PLE tumor uptake and retention kinetics. Labeling NM404 with iodine-124 represents a natural extension of the current studies with gamma-emitting nuclides due to its 4-day physical half-life. It has been shown that PET imaging with $^{124}$I affords over 40 times the sensitivity of planer 131I-gamma scintigraphy. PET, unlike traditional gamma camera imaging, not only offers significant resolution enhancement and 3-dimensional capabilities, but when used in conjunction with hybrid PET-CT also affords exquisite image quantitation due to built in attenuation correction benefits afforded by CT. Due to the preliminary success of $^{131}$I-NM404 in the current lung cancer imaging trial, it is now imperative to evaluate the tumor detection efficacy of NM404 labeled with iodine-124 by PET in order to overcome the limitations inherently associated with planer scintigraphy.

Successful Radiolabeling of NM404 with Iodine-124

The inventors have obtained high specific activity sodium-Iodide-124 in 0.1 N NaOH from Eastern Isotopes (Sterling, Va.). Radiolabeling of NM404 is achieved in greater than 60% isolated radiochemical yield by modification of an isotope exchange method. Briefly, a 2-ml glass vial is charged with 10 mg of ammonium sulfate dissolved in 50 μl of deionized water. Glass beads are added, a Teflon lined septum and screw cap are added and the vial gently swirled. A solution of 10 μg (in 10 μl of ethanol) of stock NM404 is added followed by aqueous sodium iodide-124 (1-5 mCi) in less than 30 μl aqueous 0.01 N sodium hydroxide. The reaction vile is swirled gently. A 5-ml disposable syringe containing glass wool in tandem with another 5-ml charcoal nugget filled syringe with needle outlet are attached. The glass wool syringe acts as a condensation chamber to catch evaporating solvents and the charcoal syringe traps free iodide/iodine. The reaction vessel is heated in a heating block apparatus for 45 minutes at 150° C. after which Four 20 ml volumes of air are injected into the reaction vial with a 25-ml disposable syringe and allowed to vent through the dual trap attachment. The temperature is raised to 160° C. and the reaction vial is heated another 30 minutes. After cooling to room temperature, ethanol (200 μl) is added and the vial swirled. The ethanolic solution is passed through a pre-equilibrated Amberlite IRA 400-OH resin column to remove unreacted iodide. The eluent volume is reduced to 50 μl via a nitrogen stream (use charcoal syringe trap) and the remaining volume injected onto a silica gel column (Perkin Elmer, 3 μm ×3cm disposable cartridge column eluted at 1 ml/min with hexane/isopropanol/water (52:40:8)) for purification. Final purity is determined by TLC (plastic backed silica gel-60 eluted with chloroform-methanol-water (65:35:4, Rf =0.1). The HPLC solvents are removed by rotary evaporation and the resulting radioiodinated NM404 is solubilized in aqueous 2% Polysorbate-20 and passed through a 0.22 μm filter into a sterile vial. Radiochemical purity is typically greater than 99%.

In-vivo PET Imaging of Murine Tumors with $^{124}$I-NM404.

Figure 15:
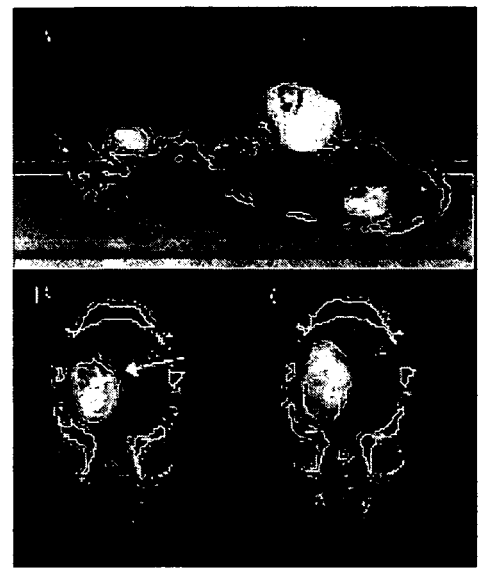
FIG. 15. Fused 3D surface-rendered MRI image (blue) and 3D microPET image (A) obtained 24h after iv injection of $^{124}$I-NM404 (80 µCi) into a rat with a CNS-1 glioma brain tumor. Images were fused using Amira (v3.1). Lower panels show (B) contrast-enhanced coronal MRI slice through the tumor (arrow) and (C) fused coronal MRI and $^{124}$I-NM404 microPET images corroborating presence and location of the tumor.

Brain Tumors. The inventors evaluated the imaging characteristics of NM404 in C6 glioma (3-5 mm in diameter) tumor-bearing and sham-operated rats. Tissue distribution analysis was performed with $^{125}$I-NM404 at 24 and 48 hours after injection, and a separate group of animals subjected to microPET scanning at various times following injection of $^{124}$I-NM404. Biodistribution analysis indicated minimal NM404 radioactivity in normal brain tissue, however, tumor/brain ratios (% injected dose/g) were 10.6, and 12.0 at 24, 48 hours, respectively. (FIG. 15) NM404 tumor uptake was corroborated by histology. These preliminary results obtained in a rat glioma model suggest that NM404 holds considerable promise for the detection of malignant primary and metastatic brain tumors.

Lung, Prostate, and Pancreatic Tumor Models

Figure 16:
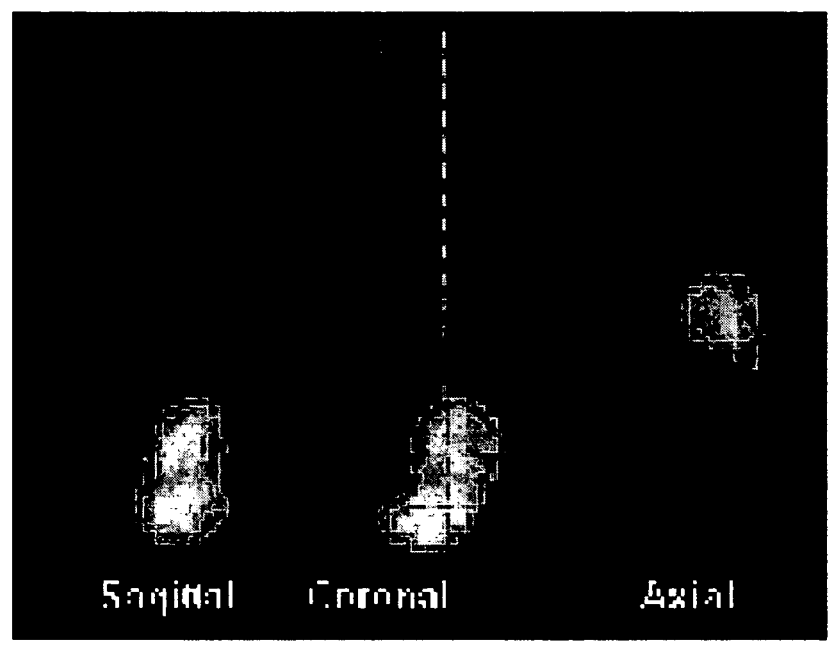
FIG. 16. $^{124}$I-MicroPET images a human A549 lung tumor xenograft in a SCID mouse 48h post injection of $^{124}$I-NM404 (80 µCi). Corresponding imaging planes are indicated by dashed green line in coronal view.
Figure 17:
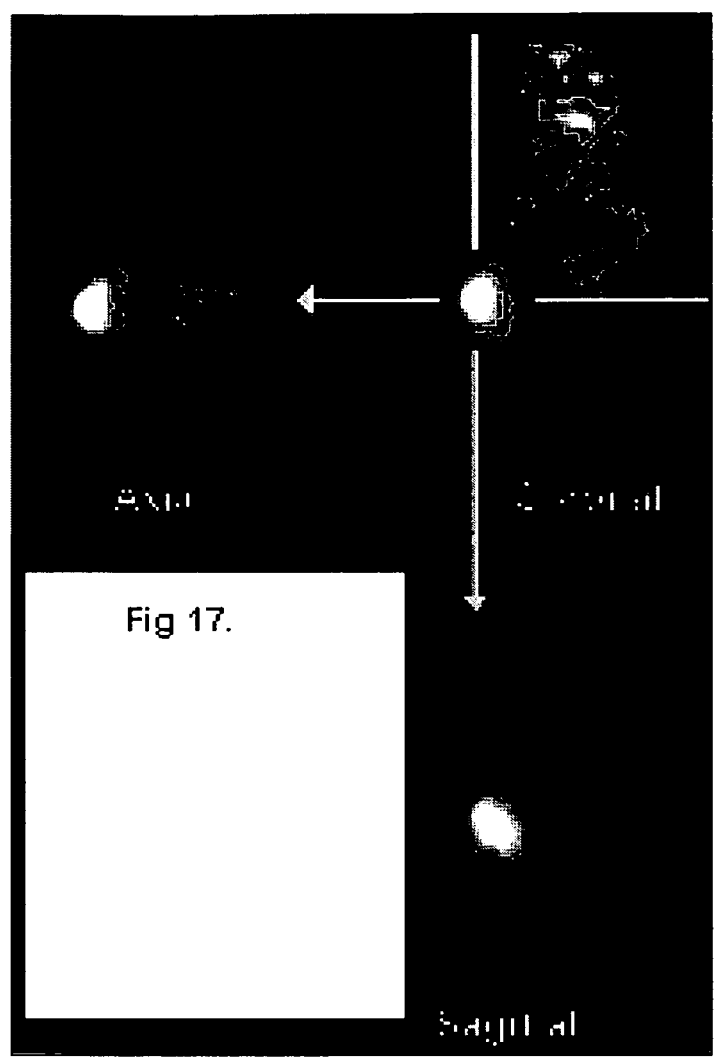
FIG. 17. $^{124}$I-MicroPET images (coronal, sagittal, and axial) 96 h after iv injection of $^{124}$I-NM404 into a PC-3 (flank) tumor-bearing mouse. No bladder activity was evident at any time point FIG. 18. $^{124}$I-MicroPET images of a transgenic mouse with a spontaneous c-myc pancreatic adenocarcinoma (5 mm) 18 h post injection of $^{124}$I-NM404 (80 µCi).
Figure 18:
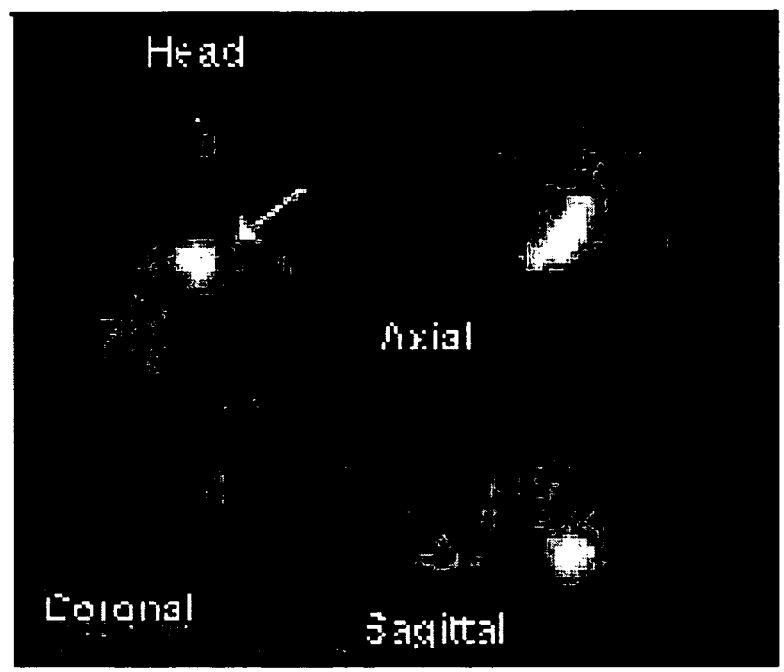

Preliminary microPET imaging results with $^{124}$I-NM404 in lung, prostate and pancreatic mouse models are presented in FIGS. 16-18. A common feature in all microPET images obtained in animal models is the lack of bladder activity at any time point. Human pharmacokinetic studies have confirmed this finding as only 4% of the agent is cleared renally within 4 days of iv injection (majority is excreted via GI route). In all cases, NM404 displayed significant tumor avidity regardless of location in the body. Tumor uptake was typically scene within 6 hours of injection, albeit tumor to background generally improved significantly over time, especially in abdominal tumors.

Stimulated by these and other observations, the inventors recently conducted a small $^{125}$I-NM404 pilot therapy study in SCID mice with human A549 lung tumor xenografts. $^{125}$I-NM404 was administered as either a single dose or alternatively in 3 doses (once a week for 3 weeks) to groups of 6 mice and a separate cohort received an equivalent mass dose of unlabeled NM404 for comparison. Single doses were 50 or 500 μCi and the repeat dose group received a total of 3 weekly 50 μCi doses. Tumor growth was monitored for 10 weeks following final injection. Preliminary results indicate a significant regression in tumor growth at the higher dose and perhaps a similar response in the 3-dose group, although these arms of the study are still ongoing. New arms are now being initiated to cover the dose levels between the current ones in order to more accurately evalutate the therapeutic potential of this agent. Even at the 500 μCi dose none of the mice showed any signs of toxicity.

Clinical Trials:

NM404 has been administered in a tracer dose for imaging (0.3 μg/kg body mass) in the Phase 1 NSCLC trial at the University of Wisconsin. A 70 kg subject would thus receive approximately 21 μg of NM404, although recent improvements in the exchange labeling procedure have resulted in much smaller mass doses being injected. Given the recent improvements in labeling and specific activity, the inventors were able to already reach a mass dose in the range of 142.9 ng/kg BW which corresponds to 0.22 nmol/kg BW or a total mass dose of 0.010 mg per 70 kg patient. Further improvements are anticipated based on a new labeling methodology as described below, which will likely result in a greater than 50-fold reduction in the mass of compound required. Taken those future improvements into account, inventors believe that the intended clinical mass dose of I-125-NM404 to be given in the clinical trials performed would be roughly 3-5 ng/kg BW or about 250 ng per 70 kg patient.

The subset of phospholipid ethers known as alkyl phosphocholines possesses a wide range of pharmacologic activities, having been studied extensively as anticancer and anti-leshmanial agents at micromolar concentrations in animal models and in humans. Neither the mode of uptake nor the precise mechanism(s) of action have been clearly defined, although disruption of membrane lipid metabolism is observed in tumor cell membranes. Miltefosine, hexadecyl phosphocholine, has a reported LD50 of 606 nmol/kg in rats with a maximum tolerated dose of 39 nmol/kg over a 4-week period. In human clinical trials, a daily oral dose of 150 mg (3×50 mg) was well tolerated with minimal side effects (nausea and emesis) (Planting AS, Stoter G, Verweij J. *European Journal of Cancer* 1993; 29A: 518-519).

Toxicology Studies Performed for NM404

This section will summarize four formal GLP toxicology studies performed using NM404. These studies are:

| Report/Study No. | Administration | Animals | Observation Period | GLP |
| --- | --- | --- | --- | --- |
| Study 27 | Single Dose | Male Rats | 14 Days | Yes |
| Study 28 | Single Dose | Male Rabbits | 14 Days | Yes |
| Study 31 | Single Dose | Female Rats | 14 Days | Yes |

| Report/Study No. | Administration | Animals | Observation Period | GLP |
|---|---|---|---|---|
| Study 32 | Single Dose | Female Rabbits | 14 Days | Yes |

Formal toxicology studies of NM404 in male rats and rabbits were performed at the Toxicology Research Center of the State University of New York at Buffalo under the direction of Dr. Paul Kostyniak. Drug vehicle and drug product were provided to Dr. Kostyniak by Dr. Raymond Counsell of the University of Michigan for testing as described in the appended synopses of Study 27 and Study 28. Since no significant toxic effects were noted at a dose of 4 mg/kg, which is a dose approximately 200 times the anticipated imaging dose at that time, and the inventors estimate to be approximately 2860 times the anticipated therapy dose for clinical trials under this invention. Human safety studies of unlabeled NM404 were initiated in normal male humans at a mass of 10 times the anticipated imaging dose and about 21 times the anticipated therapy dose. The results again showed no toxicity attributable to the drug substance. This toxicology study was performed under GLP conditions.

Subsequently, the researchers at the University of Wisconsin initiated a toxicology study of unlabeled NM404 in female rats and rabbits (Study 31 and Study 32) at the Toxicology Research Center at SUNY-Buffalo in order to expand the patient population to be studied in the NSCLC Phase 1 clinical trial. Since no significant toxic effects were noted at a dose of 0.04 mg/kg, which is a dose approximately 200 times the revised imaging mass dose at that time, and what the inventors estimate to be approximately 286 times the anticipated therapy dose for clinical trials. Human safety studies of unlabeled NM404 were initiated in normal female humans at a mass of 10 times the initially anticipated imaging dose and about 21 times the anticipated therapy dose. Again, no significant toxic effects were noted in either female rats or rabbits. This toxicology study was performed under GLP conditions.

The toxicology studies were planned at that time to go up to 200 times the anticipated mass dose in human trials. Since then, improvements to the exchange labeling methodology (see Method 2 in the CMC section) will likely result in a greater than 50-fold reduction in the mass of compound required for the reaction. Thus, recalculation of the toxicology dose indicated that no toxicity was evident at a dose of at least 10,000× the anticipated clinical dose. During the Phase 1 safety, pharmacokinetic and dosimetry trials in normal volunteers and NSCLC patients, no toxicity has been observed in either the normal male (U MI) or female (UW) volunteers or in any of the NSCLC patients participating in the study (UW).

Control and Test Articles:

The test article was a solution of C-NM404 (active ingredient) containing inactive ingredients (vehicle). The control solution for this study was the vehicle without the active ingredient.

The test article was formulated as follows:
(1) Active Ingredient: 2 mg/mL C-NM404
(2) Inactive Ingredient: 2% Polysorbate20 in sterile water (injection grade)

The control was formulated as follows:
(1) Inactive Ingredient: 2% Polysorbate20 in sterile water (injection grade)

The control and test articles were received from Raymond E. Counsell, Ph.D., Professor of Pharmacology & Medicinal Chemistry, Department of Pharmacology, The University of Michigan Medical School, Ann Arbor, Mich. on Oct. 29, 1998. At the Toxicology Research Center at the University of Buffalo, the study test site, the four (4) vials of test articles labeled "NM-404 (2 mg/ml) in 2% Polysorbate 20/Sterile Water, MAL-V1-82" and four (4) vials of control articles labeled "Control Vehicle-2% Polysorbate 20 in Sterile Water, MAL-V1-83" were inventoried and stored at room temperature.

Administration: The test article (C-NM-404) was administered at greater than 200 times the anticipated clinical dose. The control and test rats were injected intravenously in the lateral tail vein. The rats were injected with the test or control article intravenously at 2 ml/kg of body weight using a 25 gauge needle and a 1-ml syringe. The injections were given by alternating rats from the control group with rats from the test group. The injections were given cautiously over a 30 second to one minute time interval. The injection to control rat #27-01 was given at 9:03 am and last injection to test rat #27-16 was given at 11:01 am. The following rats moved during the injection and received multiple injections: control #6 (2 sites), test #9 (2 sites), test #15 (3 sites).

In human applications, ET-18-OCH3, a true PLE and thus more dissimiliar to NM404 than miltefosine, (edelfosine, mouse LD50 (oral) 200 mg/kg) is administered intravenously at a dose of 15-20 mg/kg/d at 5 mg/ml in 5% HSA. The maximum tolerated dose is 50 mg/kg. Adverse effects reported for this agent include pulmonary edema impaired hepatic function and hemolysis for up to 4 hours post-injection. (Berdel WE, Fink U, Rastetter *J. Lipids* 1987; 22:967-969). Given that the total mass dose of NM404 would be less than one ten thousandth of the daily individual dose of Miltefosine, no toxic events would be anticipated.

Study Procedures: The rats were observed by LAF personnel for signs of acute toxicity from the time of injection until 3:30 pm. The rats were weighed five (5) times a week (Monday through Friday) and their body weights, recorded in kilograms. On Dec. 17, 1998 the rats were anesthetized with sodium pentobarbital (65 mg/ml, Lot#970789, Expiration Date: Feb. 1, 2000) administered intraperitoneally. A heart puncture was then performed using a 20 gauge needle and a 10 ml syringe to collect the blood samples for the hematological CBC and the clinical blood chemistries. The rats were exsanguinated to cause death. The thymus, heart, lungs, spleen, kidneys, liver, brain, and testes were collected, examined grossly, weighed and sectioned for pathology. The tissue samples (except thymus) were placed in jars of "Z-fix" fixative for histology.

Sixteen (16) Sprague-Dawley rats were received from Harlan-Sprague Dawley, Indianapolis, Ind. All rats were males born on the same date and appeared to be healthy. They were housed at the Laboratory Animal Facility and given food and water ad lib. Each rat was given a two-part number starting with 27 (the study number) and followed by a 'unique' number of '01' to '16' (numerical). Each rat was ear punched in the right ear with the unique number of '01' to '16'. The control rats were numbered from #27-01 to #27-08 and the test rats were numbered from #27-09 to #27-16. The unique numbers were also applied to each cage indicating which rats were housed within that cage. There were four cages of control rats and four cages of test rats. The rats were weighed and the mean weight of the control group was 0.234 kilograms and 0.238 kilograms for the test group. The two groups of eight (8) rats were established by random assignment. The rats were weighed daily until the termination of the study on Day 14. Test product, dose and mode of administration, batch number: C-NM-404 (MAL-V1-82) 2 mg/ml, given via tail vein injection over 30-60 seconds Duration of Treatment: Single dose Reference therapy, dose and mode of administration, batch number: 2% Polysorbate20in sterile water, 2 ml/kg of body weight, given via tail vein injection over 30-60 seconds.

Safety: On Day 14, the blood samples for both groups will be analyzed for hematology and clinical chemistry. Additionally, the following organs will be removed for pathology report and histology slides: brain, lung, liver, heart, kidney, spleen, and testes. A compilation chart of organ weights with organ/weight ratios for each rat may be compiled.

Statistical methods:

Differences in body weights and biochemical parameters will be compared between groups using t-test.

Safety results:

No unusual behavior was noted in any of the rats during this time or throughout this 14 day study. The tail vein injection sites were checked daily when the rats were weighed and no adverse tissue reactions were noted in any of the rats. The mean weights of the rats in control group and the test group were not significantly different, despite insignificant periodic day-to-day weight loss in both groups.

The gross examination of tissues was performed one week following sacrifice by a pathologist, at SUNY at Buffalo. No gross lesions were noted in the test or control group. The tissue sections were then analyzed by light microscopic examination. There were no changes in the histopathology of the organs examined that can be attributed to the administration of the test material. Rat #27-12 receiving the test material has a small, focal area of myocardial injury (infarct in an early stage). This change is not seen in the other section of hear that was also processed so is interpreted as being quite small. Since the lesion is not seen in other animals receiving the material, the pathologist felt it is attributable to some unexplained alteration. It is not due to infection arising from the lung since the lungs do not show histopathological change.

Results of clinical blood chemistries and hematology were checked for any obvious values that were above or below the reference range. These values resulted in a group comparison using t-test at a p-value of 0.05. T-tests were performed on: phosphorus, sodium, potassium, AST, ALT, alkaline phosphatase, globulin, A/G ratio, glucose, WBC, RBC and hemoglobin. There were no significant differences found.

CONCLUSION: No acute toxicologic effects attributable to the test article had been found. There were no significant differences between the test and control group.

Similar tests were performed on male and female rabbits and female rats and no adverse effects attributable to the test article were noted.

Preclinical Pharmacology:

Inventors approach to the development of safe and effective cancer therapies is to design small-molecule carrier molecules which are capable of being selectively retained in cancer tissue, but not or minimally in non-cancerous tissues. An extension of this approach to radiotherapy would exploit the selective delivery of the radiopharmaceutical to deposit therapeutic levels of radiation within the tumor mass while minimizing radiation-induced damage to normal tissues. This technology is based on the unique biochemical and pharmacological properties of phospholipid ethers (PLE's) and especially its sub-group alkyl phosphocholine analogues, such as NM404, which displays a high degree of tumor selectivity. Phospholipids are an essential component of cellular membranes where they impart structural integrity and are intimately associated with a variety of cell signaling processes. Phosphatidylcholine, commonly known as lecithin, is such an example. Phospholipid ethers, on the other hand, represent a minor subclass of phospholipids that also reside in membranes. As the name implies, these lipids contain an ether rather than an ester linkage at the C-1 position. Platelet-activating factor (PAF) represents one of the better known phospholipid ethers.

Based on his early findings that several animal and human tumors contained much higher concentrations of naturally occurring ether lipids in their cell membranes than normal tissue (Snyder, F. and Wood R. *Cancer Res.* 1968; 28:972-978, Snyder F. and Wood R. *Cancer Res.* 1969; 29:251-258), Snyder proposed that the accumulation of ether lipids in tumors arose as a result of a lower capacity of tumor cells to metabolize these lipids. The prevailing hypothesis is that phospholipid ethers become trapped in tumor membranes because of their inability to become metabolized and eliminated, likely by a phospholipase enzyme in the cell membrane. This hypothesis is supported by experiments showing that lipid extraction of tumors following administration of radioiodinated phospholipid ethers revealed only the intact agent, whereas analysis of urine and feces revealed only metabolites (Plotzke, KP, et al., *J Nucl Biol Med*, 1993; 37:264-272). Therefore, the reason tumors retain PLE is due to the differential clearance rates of PLE from normal cells versus tumor.

Extensive structure activity relationship studies resulted in the synthesis, radiolabeling, and evaluation of over 20 phospholipid ether analogs as potential tumor-selective imaging agents. The iodinated APC analogues were readily labeled with all iodine radioisotopes using an isotope exchange method. These PLE analogs are specifically designed to incorporate aromatic radioiodine in order to render the molecule stable towards in vivo deiodination. The low level of thyroid activity in all prior preclinical imaging and tissue distribution studies (on both a % injected dose/g and % injected dose/organ basis) has confirmed the in vivo stability of the radioiodinated PLE analogs.

From the library of phospholipid ether (PLE) compounds, NM-324 [12-(3-iodophenyl)-dodecylphosphocholine], initially showed the most promise in animal tumor localization studies. A variety of tumors including mammary, prostate, squamous cell carcinoma, ovarian, colorectal, and melanoma were successfully visualized by scintigraphy with NM324. During initial human pharmacokinetic studies with the prototype agent, NM324, an unacceptable accumulation in liver tissue was observed and additional experiments to identify PLE compounds with superior tumor localization and background clearance properties were performed. Based upon this work, NM404 [18-(4-iodophenyl)-octadecylphosphocholine] emerged due to its enhanced ability to localize in tumor, its increased metabolic clearance from the liver, and its longer plasma half-life. A key observation documented the ability of NM404 to localize in lymph node metastases, which were clearly delineated by scintigraphy in a metastatic prostate tumor model without retention in uninvolved lymph nodes.

The lead compound NM404 has now been evaluated in over 25 animal tumor models and in every tumor model and tumor type studied so far, NM404 has shown tumor-selective retention. Prolonged tumor retention of $^{125}$I-NM404 has been demonstrated in mice for periods of 20-60 days post-injection. Such very extensive and protracted tumor retention characteristics may significantly enhance the radiotherapeutic efficacy of the agent, especially for isotopes with a slow radioactive decay like e.g. iodine-125.

Extensive biodistribution data for the prototype agent $^{125}$I-NM324 in several tumor models revealed tumor-to-blood ratios exceeding 8:1 at later post-injection times. In one such example in a rat mammary tumor model, tumor-to-normal tissue ratios reached a maximum at 96 hours with a tumor-to-blood ratio of 8.6 and tumor-to-muscle ratio of 20:1. Moreover, the heterogeneity of biodistribution of PLE-associated radioactivity within tumor was demonstrated by microautoradiography studies showing that the PLE radioactivity resides exclusively in viable tumor cells located toward the outer regions rather than the central necrotic regions. Comparative biodistribution data for NM-324 and NM-404 have been obtained in SCID mouse prostate and A549 lung cancer tumor models. These studies revealed high tumor-to-normal tissue ratios and tumor uptake exceeding 25% of the injected dose of NM-404 within the tumor, thus supporting the desire to study the biodistribution of NM404 in humans.

Mechanism of Action

Metabolic Studies

Formal metabolism studies were conducted on several PLE analogs including NM324, the predecessor of NM404. In these studies, each agent was examined to determine their ability to serve as substrates for enzymes. associated with PLE metabolism. Three major enzymatic pathways are involved in the metabolism of PLE. O-Alkyl glycerol monooxygenase (AGMO) is responsible for cleavage of the alkyl ether linkage at C-1 to form either the long chain fatty alcohol or subsequently, the corresponding fatty acid. Phospholipases C (PLC) and D (PLD), on the other hand, give rise to the glycerol or phosphatidic acid products, respectively. Using a microsomal AGMO enzyme preparation, NM324 was not a substrate for this enzyme when compared to [3H]-lyso-PAF (platelet activating factor), which was extensively metabolized. In a similar fashion, NM324 was analyzed as a substrate for PLC isolated from Bacillus cereus and was not hydrolyzed relative to 1-palmitoyl-2-[3H]-palmitoyl-L-3-phosphatidylcholine (DPPC), which underwent significant hydrolysis.

Finally, several PLE analogs were subjected to a phospholipase D (PLD) assay. The PLD, which was isolated from cabbage, is similar to mammalian PLD in that the cabbage form affords phosphatidylethanol-type products in addition to phosphatidic acid when the enzymatic reaction is performed in the presence of ethanol. Several of the PLE analogs subjected to these assay conditions did give rise to the phosphatidylethanol adduct, indicating possible interaction with PLD. The inventors believes that NM404 is a metabolic substrate to human Phospholipase D, and that the relative absence of Phospholipase D in cancer cell membranes is the underlying mechanism for tumor-selective retention of NM404. Although known from the literature (reference???), it is still unclear why cancers lack PLD in their membranes.

Several NM404 precursors were also subjected to in vitro metabolism studies in various cell lines including Walker tumor cells, rat muscle (H9c2), and rat hepatocytes. In these studies, the extent of metabolism was determined on the basis of radiolabeled products formed after incubation for various time periods and the results normalized to cell number or the amount of cellular protein. Subsequent lipid extraction of the incubation medium and cell suspension demonstrated little generation of PLE metabolites in the Walker tumor cells whereas a significant production of metabolites was seen in both the muscle cells and hepatocytes over the 48 h time period studied. These results correlate nicely with in vivo biodistribution studies completed on all analogs. Although several studies have been completed, the role of metabolic trapping in the uptake and retention of radiolabeled PLE analogs in tumor cells is not well defined and currently remains an active area of examination. The inventors believes that NM404 can enter the cell membranes of all cells, but gets eliminated from non-cancerous cells through rapid metabolism, whereas in cancer cells it gets trapped due to lack of appropriate metabolic enzymes.

PLD Assays

Due to the apparent universality of tumor retention of NM404 in animal tumor models and initial corroborative results in a human lung cancer trial, the inventors have begun to investigate the mechanism of action of this agent. Although membrane metabolism of PLE analogs is regulated by a variety of phospholipases, the inventors have focused initial efforts on phospholipase D (PLD) activity, based on the hypothesis that cellular uptake and retention of NM404 is inversely related to the amount of PLD present in the tumor cell membrane relative to normal cells.

Because of these findings, preliminary evaluation of PLD protein activity and PLD mRNA quantification by RT-PCR assay were performed in several murine tumor cell lines, including the murine tumor cell line hepa-1 (hepatoma), CT26 (colorectal adenocarcinoma), and TS/A (breast adenocarcinoma) and compared to normal liver. These experiments revealed that both PLD protein activity and mRNA levels were significantly lower in tumor than in normal liver tissue ($p<0.05$, T-test) (Table 1)

TABLE 1

PLD protein activity and PLD mRNA quantification for three cancer cell lines and normal liver tissue

| Cell/tissue | PLD protein activity (mU/fluorescence/μg protein/ml) | PLD mRNA (μg × $10^{-5}$/0.01 μg of total cDNA) |
|---|---|---|
| Hepa-1 | 3.3 | 6.2 |
| CT26 | 7.8 | 2.4 |
| TS/A | 2.8 | 4.0 |
| Normal liver | 14.1 | 12.2 |

As conclusion, the mechanism of selective retention of NM404 may be due to a decrease in the membrane levels of PLD, thus precluding metabolism and clearance of NM404 from the cell. Recall that earlier enzyme substrate assays conducted with PLD derived from cabbage indicated that NM404 was indeed a good substrate for this enzyme. This supports the finding of the in vitro cell culture uptake and retention study wherein it was shown that PLE analogs were sequestered by and subsequently metabolized by normal cells (which contained normal levels of PLD). If malignant tumor cells would possess a normal complement of PLD, that the agent would have been metabolized and eliminated from the tumor cells as well. Conversely it could be deduced that the lack of metabolism and clearance of the agent from malignant cells would support the hypothesis that these neoplastic cells lack PLD relative to surrounding normal host cells.

Other studies

Mechanistic Studies with PLE Analogs: NM324 and NM404 are similar in structure to miltefosine (hexadecylphosphocholine), an antitumor ether lipid studied most extensively in Europe. The antitumor properties of miltefosine and several other antitumor phospholipid ether analogs have been demonstrated in a wide range of tumor cell lines including prostate-, bladder-, and terato-carcinomas, murine and human leukemias, as well as lung, colon, ovarian, brain and breast cancers (Lohmeyer M, Bittman R. *Drugs of the Future* 1994; 19: 1021-1037). In contrast to many anticancer drugs, these phospholipid ether analogs do not bind directly to DNA and are not mutagenic. Although the precise antiproliferative mechanism of action has not been determined, they apparently act at several tumor cell sites. These compounds have been associated with a variety of cellular effects including transport, promotion of cytokine formation, apoptosis induction, and interference with a variety of key lipid metabolism and cell signaling enzymes most of which are located in the cellular membrane. Although uncertainty remains regarding the mode of PLE uptake into cells, most evidence now supports the idea that these ether lipids are directly absorbed into cell membranes where they accumulate. A widespread belief is that these agents act by perturbing membrane phospholipid metabolism; however, cellular distribution studies with these agents have been limited by spontaneous cellular compartmental redistribution during homogenization and subcellular fractionation procedures. In contrast to the tracer imaging doses (several μg) employed in the imaging and biodistribution studies cited by The inventors, antitumor effects are seen only at doses generally exceeding 150 mg per day (Planting A S, Stoter G, Verweij J. *European Journal of Cancer,* 1993; 29A:518-9; Verweij J, Planting A, van der Burg M, Stoter G. *Journal of Cancer Research & Clinical Oncology,* 1992; 118:606-8; Muschiol C, et al. *Lipids* 1987; 22:930-934).

Mechansim of Action

The prevailing mechanism for action is that phospholipid ethers such as NM404 become trapped in malignant tumor cell membranes because of their inability to become metabolized and eliminated. Extraction of tumors following administration of radioiodinated phospholipid ethers showed the presence of only the intact agent, whereas analysis of the urine and feces revealed only metabolites. Thus, it is the differential clearance rates of phospholipid ethers from normal cells versus tumor cells that form the basis of this concept. Preliminary results obtained in over 27 xenograft and spontaneous tumor models have universally shown NM404 to undergo selective and prolonged retention in tumors.

Isotope Selection for Therapy

The inventors believe that iodine-125 is the most appropriate radioisotope for combination with the NM404 targeting backbone, since:

The long isotope half-life of iodine-125 matches perfectly with the long and stable tumor retention of NM404, delivering therapeutic radiation doses for an extended period of time.

The effect of iodine-125 is caused by both, low-energy gamma/X-ray irradiation and by Auger electrons, all of which are of very limited treatment distance. Since NM404 is taken up into the tumor, iodine-125 can effectively deliver a tumor dose but it is sparing surrounding healthy tissue.

Figure 2:
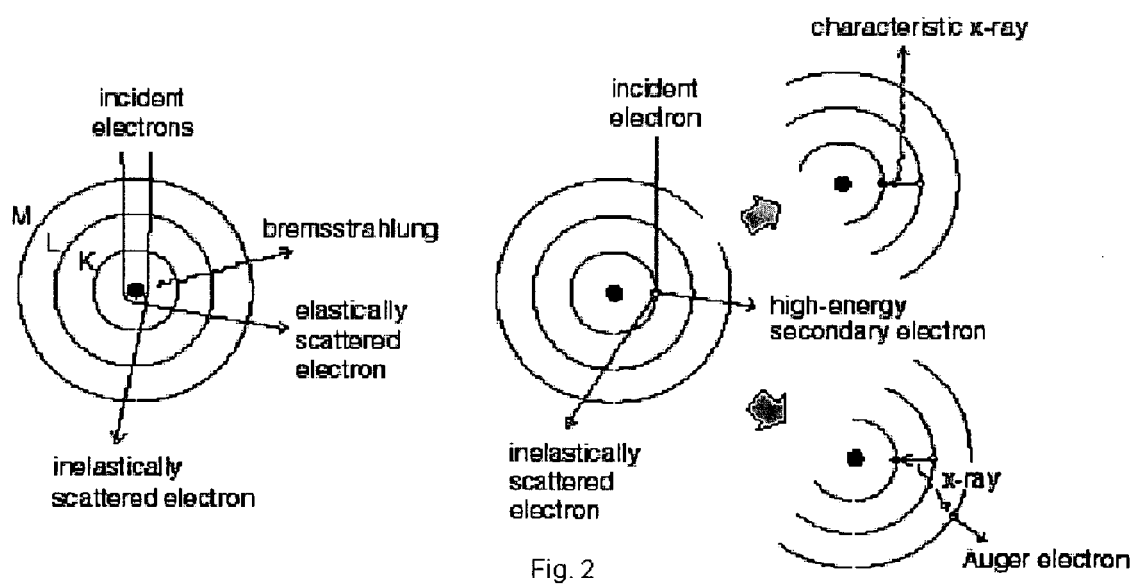
FIG. 2. Classical models showing the production of bremsstrahlung, characteristic X-rays, and Auger electrons. (left) Electrons are scattered elastically and inelastically by the positively charged nucleus. The inelastically scattered electron loses energy, which appears as bremsstrahlung. Elastically scattered electrons (which include backscattered electrons) are generally scattered through larger angles than are inelastically scattered electrons. (right) An incident electron ionizes the sample atom by ejecting an electron from an inner-shell (the K shell, in this case). De-excitation, in turn, produces characteristic X-radiation (above) or an Auger electron (below). Secondary electrons are ejected with low energy from outer loosely bound electron shells, a process not shown.

Iodine-125 has Auger electrons as one of its radio-decay by-products (FIG. 2). Auger electrons cause a pronounced biological effect, but have a very short treatment distance. Since NM404 is taken up directly into all cell membranes of cancer cells (including the nuclear membrane), the treatment distance to the DNA is very low. It may effectively allow Auger electrons to be a major contributor to I-125-NM404 treatment effects.

The iodine-125 isotope is used for formulation in this application because it exhibits favorable characteristics for cancer radiotherapy, with properties listed below:

| Gamma Irradiation | |
|---|---|
| (1) Radioisotopic half-life: | 59.43 days |
| (2) Gamma energy: | 35.5 keV |
| (3) X-Ray energy: | 27.5-31.7 keV |
| (4) Radiation half-distance: | 0.02 mm lead; 2 cm in tissue |
| Auger Electrons | |
| (1) Energy of radiation: | 1 keV |
| (2) Number of Auger electrons: | Up to 21 per gamma decay |
| (3) Radiation half-distance: | 1-10 nm |

It should be noted that although iodine-125 has great utility for in-vivo biodistribution studies and dosimetry extrapolation for diagnostic imaging, it is poorly suited for either whole-body planar imaging or in vivo scintigraphic quantification of tissue concentrations of NM404. However, iodine-124 offers superior characteristics for quantitative determination of in vivo tissue concentrations. Thus, 124-I-NM404 will find utility for in vivo pharmacokinetics and biodistribution studies but has no radiotherapeutic effect. Iodine-131 emits both beta and gamma radiation that produces a therapeutic effect. Although I-131-NM404 could potentially be used for radiotherapy, the inventors believe I-125 to be the more optimal isotope because its lower energy radiation has a shorter radiation half distance than I-131 and thus hypothesize that it will produce less damage to healthy tissue. Therefore, it was decided that I-125-NM404 would be used for all clinical radiotherapy studies performed in order to reduce the potential for collateral damage to healthy tissues.

Due to its 60-day physical half-life and low energy 35 keV photon emission, -iodine-125 is suitable for imaging experiments in mice and rats. Iodine-125 also provides therapeutic efficacy when used in permanent prostate brachytherapy implants ("brachytherapy seeds"). The major advantage of 125I is that all the photons are of low energy, insuring very limited exposure of normal tissues surrounding the tumor. The major difference between brachytherapy seeds containing iodine-125 and I-125-NM404 are the effect of Auger electrons. Since brachytherapy seeds have a metal capsule around the iodine-125, only the low-energy gamma and X-ray are of therapeutic value, and Auger electrons are eliminated by the metal capsule. In difference, I-125-NM404 is taken up into the cancer cell membranes (including into the nuclear membrane), so that Auger electrons can have a major contribution to the therapeutic effect.

Although iodine-131 has been used with great efficacy in the treatment of thyroid cancer, a significant disadvantage of iodine-131 is that there is a higher energy gamma emission which could actually expose adjacent surrounding tissues to more radiation than would occur with iodine-25.

Dosimetry

Dosimetry estimation regarding I-125-NM404 for an adult female patients were calculated based on SPECT imaging data using female non-tumor bearing rats following administration of I-131-NM404. The results are listed below:

MIRD extrapolation of 125I-NM404 rat tissue distribution data initially afforded a 5 Rad limiting dose to the adrenals and bladder wall of 2 mCi of $^{113}$I-NM404. Accordingly the inventors have conducted the preliminary pharmacokinetic studies in human lung cancer patients at 1 mCi. Similar extrapolative calculation of the dosimetry for $^{124}$I-NM404 afforded a similar 2 mCi dose level again based on projected dosimetry to the adrenals and bladder wall. Preliminary human data (5 patients), however, indicate very little uptake and retention of the agent into any abdominal organ (including the bladder and adrenals) with the exception of the liver which returns to background levels within 11 days. Although these results are not yet complete, it is likely that the actual acceptable $^{124}$I-NM404 dose will exceed 4 mCi.

MIRDOSE (IBM PC VERSION 3.1 - AUGUST 1995)

Radiation Dose Estimates for the ADULT FEMALE
for 125-I-NM404
Assumptions: Predicted Residence Time from I-131-NM404
female rat biodistribution data

| TARGET ORGAN | TOTAL DOSE | | PRIMARY | | SECONDARY | |
| --- | --- | --- | --- | --- | --- | --- |
| | mGy/MBq | rad/mCi | CONTRIBUTOR | % | CONTRIBUTOR | % |
| 1) Adrenals | 7.34E−02 | 2.72E−01 | Adrenals | 100.0% | | 0.0% |
| 2) Brain | 5.96E−03 | 2.20E−02 | Rem. Body | 100.0% | | 0.0% |
| 3) Breasts | 5.96E−03 | 2.20E−02 | Rem. Body | 100.0% | | 0.0% |
| 4) Gallbladder Wall | 5.96E−03 | 2.20E−02 | Rem. Body | 100.0% | | 0.0% |
| 5) LLI Wall | 5.96E−03 | 2.20E−02 | Rem. Body | 100.0% | | 0.0% |
| 6) Small Intestine | 7.42E−02 | 2.75E−01 | Small Int. | 96.0% | Rem. Body | 4.0% |
| 7) Stomach | 5.96E−03 | 2.20E−02 | Rem. Body | 100.0% | | 0.0% |
| 8) ULI Wall | 5.96E−03 | 2.20E−02 | Rem. Body | 100.0% | | 0.0% |
| 9) Heart Wall | 3.12E−02 | 1.15E−01 | Heart Wall | 100.0% | | 0.0% |
| 10) Kidneys | 5.09E−02 | 1.88E−01 | Kidneys | 100.0% | | 0.0% |
| 11) Liver | 4.66E−02 | 1.72E−01 | Liver | 100.0% | | 0.0% |
| 12) Lungs | 6.43E−02 | 2.38E−01 | Lungs | 100.0% | | 0.0% |
| 13) Muscle | 2.54E−02 | 9.40E−02 | Muscle | 100.0% | Uterus | 0.0% |
| 14) Ovaries | 4.10E−02 | 1.52E−01 | Ovaries | 100.0% | | 0.0% |
| 15) Pancreas | 5.96E−03 | 2.20E−02 | Rem. Body | 100.0% | | 0.0% |
| 16) Red Marrow | 2.75E−02 | 1.02E−01 | Red Marrow | 95.2% | Rem. Body | 4.8% |
| 17) Bone Surfaces | 1.84E−02 | 6.80E−02 | Red Marrow | 82.1% | Rem. Body | 17.9% |
| 18) Skin | 5.96E−03 | 2.20E−02 | Rem. Body | 100.0% | | 0.0% |
| 19) Spleen | 4.79E−02 | 1.77E−01 | Spleen | 100.0% | | 0.0% |
| 21) Thymus | 5.96E−03 | 2.20E−02 | Rem. Body | 100.0% | | 0.0% |
| 22) Thyroid | 2.98E−01 | 1.10E+00 | Thyroid | 100.0% | | 0.0% |
| 23) Urin Bladder Wall | 1.13E−02 | 4.18E−02 | Urinary Bl | 73.7% | Rem. Body | 26.3% |
| 24) Uterus | 4.78E−02 | 1.77E−01 | Uterus | 100.0% | | 0.0% |
| 27) Total Body | 1.55E−02 | 5.75E−02 | Muscle | 48.8% | Rem. Body | 23.7% |
| 28) EFF DOSE EQUIV | 4.93E−02 | 1.82E−01 | Remainder | 35.8% | Gonads | 20.8% |
| 29) EFF DOSE | 4.32E−02 | 1.60E−01 | Thyroid | 34.5% | Gonads | 19.0% |

Units of EDE and ED are mSv/MBq or rem/mCi.

RESIDENCE TIMES:

| | | | |
| --- | --- | --- | --- |
| Adrenals | 8.99E−02 | Ovaries | 3.95E−02 hr |
| Small Intestine | 4.68E+00 | Red Marrow | 3.83E+00 hr |
| Heart Wall | 6.54E−01 | Spleen | 6.29E−01 hr |
| Kidneys | 1.22E+00 | Thyroid | 4.44E−01 hr |
| Liver | 5.71E+00 | Urinary Bl Cont | 2.33E−01 hr |
| Lungs | 4.50E+00 | Uterus | 3.34E−01 hr |
| Muscle | 3.78E+01 | Remainder | 1.83E+01 hr |

For 5 rads to Adrenals: 18 mCi
For 3 rads to Ovaries: 20 mCi
For 5 rads to Thyroids: 4.5 mCi As a result of these dosimetry estimation, the following point have to be considered:

These results were based on a worst-case scenario of no excretion of NM404 from the body. The dosimetry data were calculated from SPECT imaging in rats using I-131-NM404 and then converted to I-125-NM404. The adrenal gland seems to be the dose-limiting or critical organ for radiation exposure. In the SPECT imaging experiments the thyroids of rats were unblocked. Thus, the thyroid calculations should be evaluated with caution.

Pharmacology Summary

Comprehensive summary of the synthesis and the biological properties of NM404 is discussed in U.S. patent application Ser. No. 60/593,190 filed on Dec. 20, 2004 U.S. application Ser. No.10/906,687 filed on Mar. 2, 2005 and U.S. Provisional Application No. 60/521,166, filed on Mar. 2, 2004, all of which are incorporated herein by reference for all purposes.

The inventors' approach is to design small-molecule carrier molecules which are capable of selectively delivering a diagnostic or therapeutic probe to the desired target tissue capitalizes on unique biochemical or pharmacological properties of molecules displaying a high degree of tissue or tumor selectivity.

It was initially observed that a variety of animal and human tumors contained much higher concentrations of naturally occurring ether lipids in the cell membranes than normal tissue. It was hypothesized that phospholipid ether analogs could accumulate in tumor cells due to their lower capacity to metabolize these lipids. The inventors have pursued radioiodinated phospholipid ether (PLE) analogs as potential tumor-selective imaging agents. Several PLE analogs have exhibited a striking universal ability to selectively localize in a wide variety of transplanted rat, mouse, and human tumor models.

The prevailing hypothesis is that phospholipid ethers become trapped in tumor membranes because of their inability to be metabolized and cleared. Indeed, tumor analysis following administration of radioiodinated phospholipid ethers showed the presence of only the intact agent, whereas analysis of the normal tissues (liver and muscle), urine, and feces revealed only metabolites. Thus, it is the differential clearance rates of phospholipid ether analogs from normal cells versus tumor cells that form the basis of this targeting concept.

Preclinical Studies with First Generation PLE Analogs: Phospholipid ethers can easily be labeled with iodine radioisotopes using radiolabeling methods developed in the labs. The iodophenyl phospholipid ether analogs are specifically designed so that the radioiodine affixed to each molecule is stable to facile in vivo deiodination. It was found that any chemical modification of the phosphocholine moiety or shortening the chain length of the iodophenylalkyl moiety to less than 8 methylenes resulted in little or no tumor uptake. The inventors have now synthesized over 20 radiolabeled PLE compounds and tested in vitro and in vivo. Two of these, namely NM-294 and NM-324 [12-(3-iodophenyl)-dodecylphosphocholine], initially showed the most promise in animal tumor localization studies. These prototype compounds, labeled with iodine-125, selectively localized in tumors over time in the following animal tumor models; 1) Sprague-Dawley rat-bearing Walker 256 carcinosarcoma; 2) Lewis rat-bearing mammary tumor; 3) Copenhagen rat-bearing Dunning R3327 prostate tumors; 4) Rabbits-bearing V×2 tumors; and 5) athymic mice-bearing human breast (HT39), small cell lung (NCl-69), colorectal (LS174T), ovarian (HTB771P3), and melanoma tumors. Optimal tumor localization of these agents takes from one to several days due to the more rapid clearance of the radioactivity from normal tissues relative to tumor.

Certain PLE cmpounds discussed in the following paragraphs are shown in FIG. 1.

Clinical Evaluation of NM324: Although first generation compounds NM-324 and NM-294 displayed similar animal tumor localization characteristics, NM-324 was easier to chemically synthesize and was thus selected as the lead compound for initial clinical studies. Although images obtained in several human lung cancer patients detected tumors, images were complicated by high liver radioactivity (FIG. 3).

Figure 4:
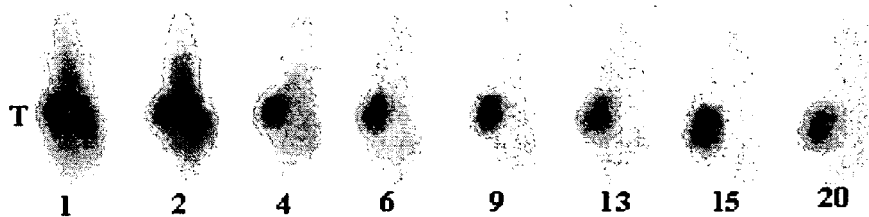
FIG. 4. Time course (days) of NM404 in a SCID mouse with a human RL-251 adrenal tumor (T) xenograft.

Second Generation PLE Analogs: In order to decrease liver uptake and prolong the plasma phase, the inventors examined 9 structural analogs of NM-324 to identify agents that would display improved tumor-to-background tissue ratios with decreased liver uptake. The new PLE analogs were synthesized and radiolabeled with $^{125}$I for initial image analysis in Copenhagen rats bearing Dunning R3327 prostate tumors. Based upon this initial screen, NM-404 not only exhibited much lower liver activity than its predecessor NM324 but also maintained prolonged tumor retention (FIG. 4. NM404 was therefore selected to undergo further imaging and biodistribution analysis in a variety of animal-tumor models.

Accordingly, NM404 has now been evaluated in over 20 xenograft and spontaneous animal tumor models as shown in Table 2. In all tumor models the agent displayed significant tumor uptake and retention regardless of location. Although tumor retention can be explained by a lack of metabolic phospholipase enzymes in the tumor cell membranes, the exact mechanism of tumor cell uptake is unknown. Furthermore, the inventors know the agent does not localize in benign intestinal adenomas (polyps) so it was desirable to further evaluate the propensity of the agent to localize in an intermediate stage of tumorigenesis, namely hyperplasia. The inventors are currently evaluating the selectivity of NM404 in a unique mouse tumor model developed at Wisconsin, wherein both preneoplastic hyperplasias and malignant adenocarcinomas form spontaneously in the mammary gland. Preliminary results in this model indicate that the agent is not taken up and retained in preneoplastic lesions, and thus, appears to be exclusively retained by malignant tumor cells. If this initial observation is validated, then via genomic and or proteomic analysis the inventors may be able to identify a key genetic difference between malignant tumors and their non malignant predecessor cells. This could identify a completely new molecular therapeutic target that may be universal for all types of cancer.

The table below summarizes the wide variety of cancer types and tumor lines that have been evaluated regarding accumulation by NM404.

TABLE 2

Tumor models examined with NM404

| Tumor Model | Species | Type | NM 404 Tumor Localization* |
|---|---|---|---|
| Human Tumor Xenografts | | | |
| Prostate PC-3 | SCID Mouse | Adenocarcinoma | Yes |
| Lung A-549 (NSCC) | SCID Mouse | Adenocarcinoma | Yes |
| Lung NCl H-69 (Oat Cell) | Nude Mouse | Adenocarcinoma | Yes |
| Adrenal H-295 | SCID Mouse | Adenocarcinoma | Yes |
| Adrenal RL-251 | SCID Mouse | Adenocarcinoma | Yes |
| Melanoma A-375 | Nude Mouse | Adenocarcinoma | Yes |
| Colon LS-180 | Nude Mouse | Adenocarcinoma | Yes |
| Ovarian HTB-77 | Nude Mouse | Adenocarcinoma | Yes |
| Animal Tumor Xenografts | | | |
| Mammary MCF-7 | Rat | Adenocarcinoma | Yes |
| Prostate MatLyLu | Rat | Adenocarcinoma | Yes |
| Walker-256 | Rat | Carcinosarcoma | Yes |
| Recent Rodent Tumor Models | | | |
| TRAMP prostate | Transgenic mouse | Adenocarcinoma | Yes |
| LuCaP prostate | Mouse xenograft | Adenocarcinoma | Yes |
| Liver CT-26 | Mouse xenograft | Colorectal adenocarcinoma | Yes |
| TGFα Hepatoma | Transgenic mouse | Hepatoma | Yes |
| Min Mouse Intestinal | Transgenic mouse | Adenocarcinoma | Yes |
| Melanoma B16 | Mouse xenograft | Adenocarcinoma | Yes |
| SCC1 and 6 | Nude mouse xenograft | Squamous cell carcinoma | Yes |
| Mammary Adenocarcinoma | Apc/$^{min+}$ mouse | Adenocarcinoma | Yes |

TABLE 2-continued

Tumor models examined with NM404

| Tumor Model | Species | Type | NM 404 Tumor Localization* |
|---|---|---|---|
| Mammary SCC | Apc/$^{min+}$ mouse | Squamous cell carcinoma | Yes |
| Glioma L9 and CNS-1 | Rat xenograft | Glioma | Yes |
| Pancreas c-myc/k-ras | Transgenic mouse | Ductal/acinar | Yes |
| Retinoblastoma | Transgenic mouse | Blastoma | Yes |
| Cervical | Transgenic mouse | Adenocarcinoma | Yes |
| Mammary alveolar hyperplasia | Apc/$^{min+}$ mouse | Hyperplasia | No |
| Intestinal adenoma | Apc/$^{min+}$ mouse | Hyperplasia | No |

*Localization defined as >5% injected dose per gram tumor basis based on tissue distribution data. No decay corrected tumor clearance was observed from 14 to 80 days in these models using $^{125}$I-NM404.

Tissue Distribution and Kinetics

Consistently, NM404 has been found to be retained in tumor tissue for long and extended periods of time. Tumor concentrations are almost stable for many weeks following administration of NM404, showing slow elimination from cancerous tissue over time. In contrast, NM404 is eliminated from normal tissue within a few days reaching very low levels.

Figure 5:
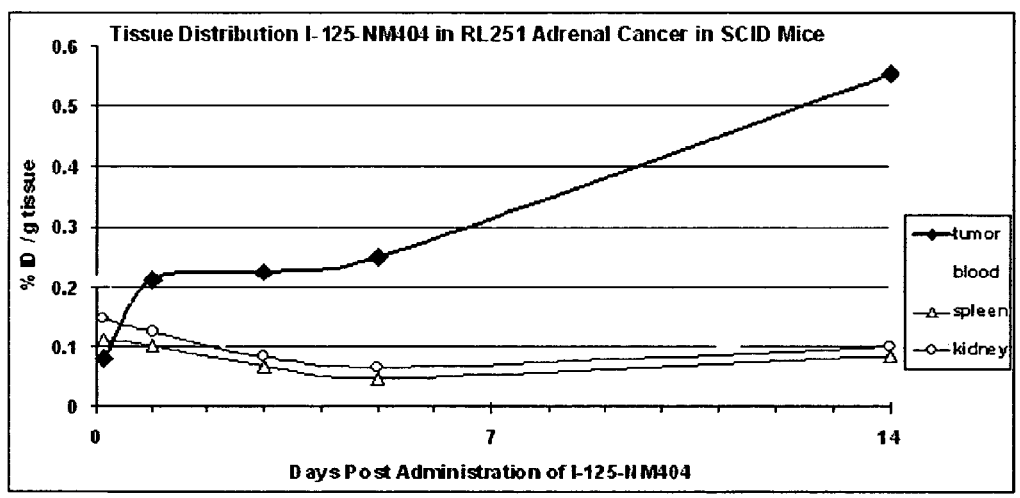
FIG. 5. Tissue distribution 1-1125-NM404 in RL 251 Adrenal Cancer in SCID mice depicting that while accumulation in the tumor increased, distribution in blood, spleen and kidney reduced by days 1 through 14.

Additionally, NM404 was designed to have a long blood half life. This ensures prolonged exposure of NM404 to the tumor tissue and ensures uptake of up to 10-25% of the injected dose into the tumor tissue. The inventors believe that it is very important for a radiotherapy compound to have a large portion of the injected dose accumulating in the tissue of interest. As a consequence of the long blood half life, NM404 will continuously accumulate in tumor tissue over time. An example of this pattern is provided in FIG. 5. This may lead to a delayed onset of the therapeutic effect until the accumulation of NM404 into the tumor tissue has been continuing for several days or weeks.

Blood Plasma Kinetics

The first-generation prototype compound NM324 was found to have a elimination half life time in plasma of 2.43 hours in rats. By comparison, the lead compound NM404, has a elimination half life time of roughly 209 hours in rats (distribution phase half life is 4.86 hours).

Radiotherapeutic Study of I-125-NM404

Figure 6:
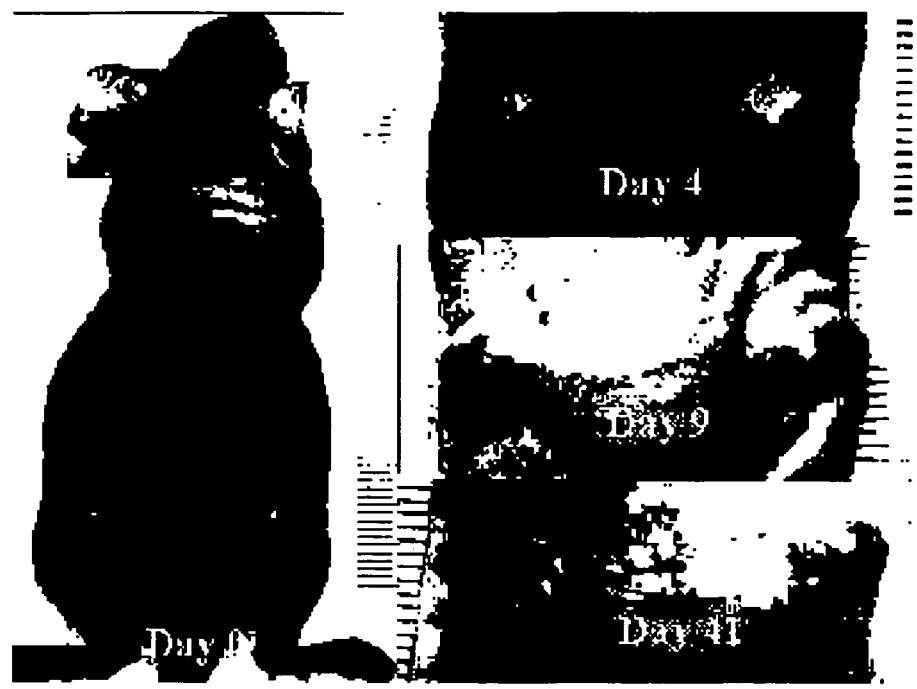
FIG. 6. Apparent SCC1 and SCC6 tumor regression after injection of 1251-NM404. By day 41, the tumor is significantly reduced.

During the course of mouse tumor uptake and retention studies with "imaging" doses (15-20 μCi/20 g mouse) of $^{125}$I-labeled NM404, several apparent therapeutic responses have been observed (unpublished results). In an Apc$^{Min}$/+ mouse mammary tumor model it has generally been noted that tumor growth remains static following a single intravenous injection of NM404. Some of these animals also lost all hair above larger mammary tumors at around 8 days after injection. Moreover, these mice also get intestinal tumors and usually suffer from intestinal bleeding resulting in severe anemia, which renders their feet white. Dr. Moser noted that the feet of these mice had reverted to a pink color around 5 days after a single injection of NM404. Upon eventual dissection of these animals, it was noted that only a very few, if any, of the expected 20 or so intestinal tumors usually found at this age actually remained. The "white to pink feet" phenomenon was also observed in a separate, but more aggressive, mouse intestinal adenocarcinoma model, wherein dissection at 12 days following NM404 administration, again revealed that most, if not all, of the expected intestinal tumors were gone. After 21 days In both intestinal models, animals that received NM404 easily outlived their untreated litter mates. Another compelling example of tumor regression is illustrated in FIG. 6. Two litter mates each received SCC1 and SCC6 xenografts in their left and right flanks, respectively. One mouse received a single injection of $^{125}$I-NM404 (20 μCi). The mouse that didn't receive NM404 died 21 days later, whereas the tumors in the treated mouse regressed significantly and the animal was quite healthy 80 days after injection. These coincidental findings were reconfirmed in two separate age-matched groups each involving more than 6 mice. Although these observations with $^{125}$I-NM404 are anecdotal at this point, they do seem to strongly indicate potential for radiotherapy applications particularly if labeled with iodine-131. Ongoing quantitative tumor uptake and retention studies in several animal tumor models will also provide sufficient data to initiate a comprehensive dosimetry analysis for this agent in order to estimate its true radiotherapeutic potential.

Due to its 60-day physical half-life and low energy 35 KeV photon emission, iodine-125 is suitable for imaging experiments in mice and rats. Iodine-125 also affords therapeutic characteristics. In one imaging experiment (FIG. 6), 2 nude mice were each inoculated with subcutaneous squamous cell lines SCC1 and SCC6 tumor cell implants on opposing flanks. SCC1 and SSC6 cells were used because one is radiosensitive relative to the other. After 14 days when the average tumor size was approaching 0.5 cm in diameter, one of the mice received 20 μCi of I-125-NM-404 and the other one receive unlabeled NM404 in an equal mass dose. The mouse receiving the unlabeled cold compound had to be euthanized 20 days after injection due to both tumors reaching the termination size limit as defined in the animal use protocol. Both tumors in the $^{125}$I-NM404 mouse regressed dramatically and unexpectedly over the course of several weeks (FIG. 6) after a single injection of an imaging dose of NM404. This mouse never did reach terminal tumor size and the mouse was actually euthanized after 90 days in order to collect histology sections.

Preliminary Report of Ongoing Tumor Therapy Studies

Preclinical study-preliminary results:

Efficacy of single injection of I-125 labeled SF404A in an A549 SCID mouse model Purpose and rationale: To determine an effective dose for radiotherapy using single injection of I-125 labeled SF404A in a xenograft tumor model Tumor model: A549 (human non-small cell lung cancer, NSCLC, from ATCC) are maintained in Ham's F-12K media supplemented with 10% fetal bovine serum. Tumor cell suspension ($1\times10^6$ cells in phosphate-buffered saline) is injected s.c. into the right flank of female SCID mice (6-8 weeks, C.B-17/IcrHsd-Prkcd$^{scid}$, Harlan). Animals are given free access to food and water, tumor growth and animal weight are monitored. Upon reaching 4-5mm in diameter, mice will be divided into groups of 6 for therapy study.

Dosing:

Single injection of SF404A at Day 0

Groups:

(1) 5 study groups: 4 treatment+1 control
(2) N=6 per group
(3) 4 acute dose levels: 50, 150, 250 and 500 μCi per mouse
(4) Control group dosed with equivalent mass amount of NM404:
(5) Control: 0 μCi per mouse ("cold" NM404)

Efficacy Assessments:

(1) Tumor size (caliper) measured once a week.
(2) Survival
(3) General appearance (activity, alertness, mobility)
(4) Until 10 weeks post-injection or until no animal in the control group is alive, whatever comes first
(5) Histopathology assessment of tumor or residual tumor site.

Photograph of tumor at Day 0, 30, and 60 for each animal.

The purpose of the study was to determine an effective dose for radiotherapy using single injection of I-125-NM404 (formulation SF404A) in a xenograft tumor model.

The tumor model used for this study was A549, a human non-small cell lung cancer, (NSCLC) obtained from ATCC (Manassas, Va.). The tumor cells are maintained in Ham's F-12K media supplemented with 10% fetal bovine serum. Tumor cell suspension ($1\times10^6$ cells in phosphate-buffered saline) is injected s.c. into the right flank of female SCID mice (6-8 weeks, C.B-17/IcrHsd-Prkcd$^{scid}$, Harlan). Animals are given free access to food and water. Upon reaching 5-10 mm in tumor diameter, mice will be enrolled in the study.

A single intravenous injection of SF404A was performed at Day 0. For the control group, cold compound (C-NM404) has been injected. For treatment groups I-125-NM404 has been injected.

The study contained 5 groups; 4 treatment groups (n=6/group) and 1 control group (n=9). The iodine doses for the treatment groups were 50, 150, 250 and 500 μCi per mouse. The control group was dosed with an equivalent mass amount of C-NM404 (0 μCi).

For assessment of efficacy of treatments, the following assessments were performed:

(1) Tumor size (caliper) measured once a week
(2) Survival
(3) General appearance (activity, alertness, mobility)
(4) Digital pictures of tumor-bearing mouse Assessments were made until 10 weeks post-injection or until no animal in the control group is alive, whatever comes first. Histopathology assessment of tumor or residual tumor site was performed at the end of the study.

(1) 50 μCi group: 6 animals were enrolled;
(2) 150 μCi group: 5 animals were enrolled;
(3) 250 μCi group: 6 animals were enrolled;
(4) 500 μCi group: 6 animals were enrolled.

As part of this preliminary report, the inventors include the following animals in the analysis:

(1) Control: n=7
(2) 50 μCi group: n=4
(3) 150 μCi group: n=5
(4) 250 μCi group: n=6
(5) 500 μCi group: n=5

The baseline tumor volumes (in mm$^3$) for each group were:

|  | Average tumor volume | SD |
|---|---|---|
| Control | 1152 | 1314 |
| 50 μCi group: | 198 | 138 |
| 150 μCi group: | 1699 | 1251 |
| 250 μCi group: | 360 | 156 |
| 500 μCi group: | 1041 | 673 |

Since the tumor volumes of the control group and the 150 μCi group was substantially larger than the other groups and from what was previously planned, a complete re-enrollment of both groups with smaller tumor sizes has been initiated. As far as the tumor volumes for the 500 μCi group, the inventors believe that the study may be biased against this group. Because of necrosis and inefficient blood supply, larger tumors may not respond as well to I-125-NM404 treatment.

The following average tumor volume for each group was recorded over the 10-week assessment period:

| Week | Control (n = 7) | 50 μCi (n = 4) | 150 μCi (n = 5) | 250 μCi (n = 6) | 500 μCi (n = 5) |
|---|---|---|---|---|---|
| 0 | 1152 | 198 | 1699 | 360 | 1041 |
| 1 | 1289 | 599 | 1847 |  | 964 |
| 2 | 1667 | 691 | 2430 | 756 | 1281 |
| 3 | 2418 | 987 | 2758 | 821 | 1110 |
| 4 | 3169 | 2283 | 4144 |  | 1300 |
| 5 | 3763 | 3977 | 4478 |  | 1626 |
| 6 | 4971 | 4951 | 4668 |  | 1735 |
| 7 | 6207 | 6999 | 4817 |  | 1697 |
| 8 | 6253 | 8188 | 6049 |  |  |
| 9 | 7175 | 9978 | 7780 |  |  |
| 10 | 7068 | 8342 | 6894 |  |  |

This is also reflected in the FIG. 10

In summary, control animals show rapidly growing tumors over the 10-week assessment period. This confirms that the compound itself C-NM404 has no substantial effect on tumors growth. The 50 μCi dose group did not show any difference to control animals, hence this seems to be an ineffective dose in this animal model. The 150 μCi dose group shows no treatment effect as well, however (as was pointed out before) this dose group started with unusually large tumors at Day 0, however this may show different results with this dose group of 150 μCi with smaller tumors.

Figure 7:
FIG. 7. The image shows one of the tumor-bearing animals treated with 250 μCi of I-125-NM404 at 4 weeks following injection. The hair above the tumor has fallen off, presumably due to the strong accumulation of radioactivity in the tumor. Additionally, the surface of the tumors appears "caved in" and shows darker areas, presumably from hemorrhage and necrosis. The figure shows the effect of I-125-NM404 on the tumor. Although tumor size (outer dimensions) may not shrink, I-125-NM404 causes central necrosis. The measurement method measuring outer tumor dimensions may have underestimated tumor volume response following I-125-NM404.

Preliminary data indicates that both the 250 and 500 μCi show a substantial and prolonged treatment effect. Tumor volumes are stable and same tumors appear "collapsed" (the tumor surface has caved in, as shown in FIG. 7). Additionally, hair above the tumors fells off confirming substantial accumulation of radioactivity in these tumors.

Other Ongoing Preclinical Tumor Therapy Studies

Efficacy of Fractionated Dose vs Single Injection of I-125 Labeled SF404A in an A549 SCID Mouse Model This preclinical study assesses fractionating the 150 μCi dose by injecting 3 weekly 50 μCi doses instead of one single 150 μCi dose as given in the previous study.

Purpose and rationale: To determine the radiotherapeutic efficacy of a fractionated dose of I-125 labeled SF404A vs a single injection of an equivalent total dose in a xenograft tumor model This study is an adjunct to CLTR-Pre-05-001, which contains the 150 μCi single dose used for comparison.

Tumor Model:

A549 (human non-small cell lung cancer, NSCLC, from ATCC) are maintained in Ham's F-12K media supplemented with 10% fetal bovine serum. Tumor cell suspension ($1\times10^6$ cells in phosphate-buffered saline) is injected s.c. into the right flank of female SCID mice (6-8 weeks, C.B-17/IcrHsd-Prkcd$^{scid}$, Harlan). Animals are given free access to food and water, tumor growth and animal weight are monitored. Upon reaching 4-5mm in diameter, mice will be divided into groups of 6 for therapy study.

Dosing:

Single injection of I-125-SF404A at Day 0 vs a fractionated dose of I-125-S404A

Groups:

2 study groups: 1 Fractionated dose, 1 Single injection (1) N=6 per group
(2) 150 µCi (3×50 µCi) per mouse by by fractionated injection, at 1 week intervals from day 0
(3) 150 µCi per mouse by single injection Efficacy Assessments:

(1) Tumor size (caliper) measured once a week.
(2) Survival until 10 weeks post-injection or until no animal in either group is alive, whatever comes first
(3) General appearance (activity, alertness, mobility)
(4) Histopathology assessment of tumor or residual tumor site.
(5) Photograph of tumor at Day 0, 30, and 60 for each animal.

Efficacy of single injection of I-125 labeled SF404A in a PC-3 (Prostate cancer) SCID mouse model Purpose and rationale: To determine an effective dose for radiotherapy using single injection of I-125 labeled SF404A in a prostate cancer xenograft tumor model Tumor model:

PC-3 (human prostate cancer, from ATCC) are maintained in Ham's F-12K media supplemented with 10% fetal bovine serum. Tumor cell suspension (1×10$^6$ cells in phosphate-buffered saline) is injected s.c. into the right flank of male SCID mice (6-8 weeks, C.B-17/IcrHsd-Prkcd$^{scid}$, Harlan). Animals are given free access to food and water, tumor growth and animal weight are monitored. Upon reaching 4-5mm in diameter, mice will be divided into groups of 6 for therapy study.

Dosing:

Single injection of SF404A at Day 0

Groups:

(1) 5 study groups: 4 treatment+1 control
(2) N=6 per group
(3) 4 acute dose levels: 50, 150, 250 and 500 µCi per mouse
(4) Control group dosed with equivalent mass amount of NM404: 0 µCi per mouse ("cold" NM404)

Efficacy Assessments:

Tumor size (caliper) measured once a week.

Survival: until 10 weeks post-injection or until no animal in the control group is alive, whatever comes first (1) General appearance (activity, alertness, mobility)
(2) Histopathology assessment of tumor or residual tumor site.
(3) Photograph of tumor at Day 0, 30, and 60 for each animal.

This preclinical study duplicates the previous study single injection study but with a different tumors model.

Clinical Evaluation for Imaging of Prostate and NSCLC using a Phospholipid Ether Analog, NM-404.

Safety assessment in normal male subjects healthy normal female subjects were carried out and it was determined that a dose level of 3 µg/kg of C-NM-404 is safe to administer to male subjects. This dose is 10 fold the 0.3 µg/kg dose of $^{113}$I-NM404 anticipated to be used for imaging in patients with metastatic prostate cancer. A dose level of 3 µg/kg of C-NM-404 is safe to administer to female subjects. This dose is 10 fold the 0.3 µg/kg dose of $^{131}$I-NM404 anticipated to be used for imaging in patients with metastatic lung cancer.

Imaging Characteristics of NM-404 in Patients with NSCLC

Metastatic Non-Small Cell Lung Cancer Subjects:

Written informed consent will be obtained. $^{131}$I-NM404 at a dose of 0.3µg/kg will be infused over 10 minutes. The aqueous solution containing $^{131}$I-NM404 will be prepared using sterile technique in Dr. Jamey Weichert's laboratory at the University of Wisconsin. The preparation dispensed by the Nuclear Pharmacy will be certified as sterile and pyrogen-free. The subject will be monitored for adverse reactions during and after the infusion. Vital signs will be checked immediately after the infusion, and at 60 minute intervals up to four hours post-injection. They will be observed for adverse events throughout this time. The subjects will return 24, 48, 72, 96, 120, 144 hours and 30 days after the infusion. NM404 Pet scans will be obtained at 4, 8, 24, 48 and 96 hours post injection. Vital signs will be monitored at these times. Any adverse reactions experienced by the subjects will be recorded. All subjects will receive SSKI oral solution beginning one day prior to the 131 I-NM404 infusion and continue for 7 days to reduce thyroid exposure to free radioiodine. Serum pharmacokinetics will be drawn pre-infusion, 5, 10, 30, 60, 120, 240, 360 minutes post-injection and at 24, 48, 72 and 96 hours post injection. Sequential 24 hour urine collections for 0-24, 24-48, 48-72 and 72-96 hours post injection will be obtained.

Plasma pharmacokinetics confirmed an average 113.1 hours (SEM=7.9 h) elimination half life time for NM404.

An average of 3.4% (range from 0.9% to 9.8%) of injected dose was eliminated via the kidneys with 96 hours of intravenous administration of NM404. A dose level of 0.3 µg/kg of 131I-NM404 was safe to administer to subjects with advanced non-small cell lung cancer. The elimination plasma half life time of NM404 was found to be 113.1 hours and the urinary elimination was found to be roughly 3.4% within 96 hours post-injection.

Prostate Cancer

The present invention provides preliminary data regarding the use of the second-generation PLE analog, NM404, in imaging patients with prostate cancer. This agent, currently under investigation at the University of Wisconsin, is selectively retained in tumors in high levels, and has high sensitivity and specificity in preclinical models. It has passed acute toxicology testing in both rats and rabbits at >1000 times the anticipated human imaging dose, and the unlabeled agent was administered at 10 times the anticipated imaging mass dose to 10 normal volunteers at the University of Michigan and University of Wisconsin to document safety. The inventors hypothesize that imaging with NM404 will ultimately prove as sensitive as imaging with FDG, will also be more specific, may afford therapeutically utility and due to its relatively long half-life be available in virtually every PET facility regardless of location.

The biodistribution, kinetics, optimal imaging times, and dosimetry of $^{131}$I-NM404 are currently being evaluated in a pilot study in patients with lung cancer (NSCLC) at UWCCC. This agent has also been evaluated preclinically in a metastatic prostate tumor model in which lymph node metastases were clearly delineated by scintigraphy following intravenous administration of NM404 but, pertinently, the tracer was not retained by uninvolved lymph nodes. Selectivity of NM404 for malignant cells is particularly relevant in prostate cancer as conventional tumor markers such as PSA may also be elevated in a variety of benign disease states including prostatitis and benign prostatic hypertrophy. Furthermore, selective uptake and prolonged retention by tumor cells supports a role for NM404 as a tumor-selective diagnostic and therapeutic agent.

The preliminary results will provide the preliminary data for a subsequent study designed to more accurately estimate the predictive power of NM404 for staging and/or following response to therapy in prostate cancer. In addition since NM404 has high tumor uptake, this agent also has the potential to be developed as a therapeutic agent when coupled with higher doses of 131I, 125I, another halogen astatine. Iodine-125 would be especially desirable in prostate cancer patients due to its short Auger electron path length in tissue, which would theoretically minimize radiation effects in neighboring normal tissues like the rectum. In a therapeutic sense, the 60 day half-life of iodine-125 matches exceedingly well with the prolonged tumor retention properties of NM404.

Targeting Tumor Cells

One approach to the development of sensitive, more available imaging exams is to design carrier molecules which are capable of selectively delivering a radiopharmaceutical probe to the desired target tissue. The approach has been to capitalize on the unique biochemical and pharmacological properties of phospholipid ether analogues such as NM404, which displays a high degree of tumor selectivity. Phospholipids are an essential component of cellular membranes where they impart structural integrity and are heavily associated with a variety of cell signaling processes. Phosphatidylcholine, commonly known as lecithin, is such an example. Phospholipid ethers, on the other hand, represent a minor subclass of phospholipids that also reside in membranes. As the name implies, these lipids contain an ether rather than an ester linkage at the C-1 position. Platelet-activating factor (PAF) represents one of the better known phospholipid ethers. As described above, tumors retain PLE is due to the differential clearance rates of PLE from normal cells versus tumor.

While initiating human pharmacokinetic studies with the prototype agent, NM324, ongoing experiments to identify PLE compounds with superior tumor localization and background clearance properties were performed. Based upon this work, NM404 [12-(4-iodophenyl)-octadecylphosphocholine] was selected due to its enhanced ability to localize in tumor, its increased metabolic clearance from the liver, and its longer plasma half-life. In a key experiment documenting the ability of NM404 to localize in metastases, lymph node metastases were clearly delineated by scintigraphy in a metastatic prostate tumor model following intravenous administration of NM404, but the tracer was not retained by uninvolved lymph nodes.

Figure 19:
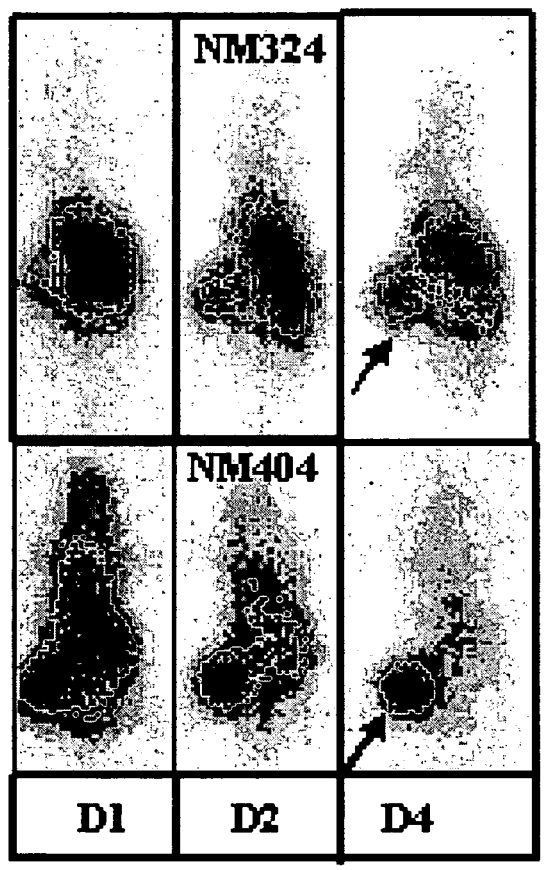
FIG. 19. Scintigraphic comparison of NM404 (bottom panel) and NM324 (top panel) at 1, 2, and 4 days in a SCID mouse with human prostate PC-3 tumor (arrow) implanted in the flank. Liver and background radioactivity are much improved with NM404.
Figure 20:
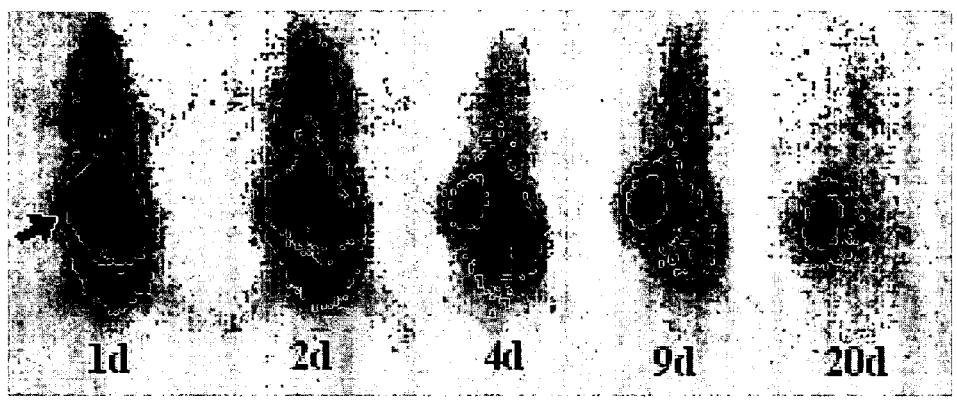
FIG. 20. Time course of $^{125}$I-NM404 in human RL-251 adrenal cancer xenograft in a SCID mouse. Prolonged tumor (1.5×0.5 cm, arrow) retention is evident even after 20 days.

Comparative scintigraphic imaging results for NM324 and NM404 in PC-3 prostate tumor-bearing SCID mice revealed high tumor-to-normal tissue ratios and significant decreases in background abdominal and liver radioactivity with NM404 (FIG. 19). This agent has now been evaluated in 27 animal tumor models and it is clear that once the agent enters tumor cells, it reaches a metabolic dead end and becomes trapped. Prolonged tumor retention of this agent is demonstrated in a human adrenal tumor xenograft implanted into SCID mice (FIG. 20). Using $^{125}$I-labeled NM404, the inventors have been able to image mammary and prostate tumors in mice in excess of 60 days. Prolonged tumor retention characteristics significantly enhance the radiotherapeutic efficacy of the agent.

Recent imaging and biodistribution studies performed in rodent models aimed at determining the uptake characteristics in a wide variety of xenograft and spontaneous (endogenous or transgenic) tumor types are summarized above. These agents have displayed selective localization and prolonged retention in every malignant tumor regardless of anatomic location (including lymph nodes) studied to date.

Figure 21:
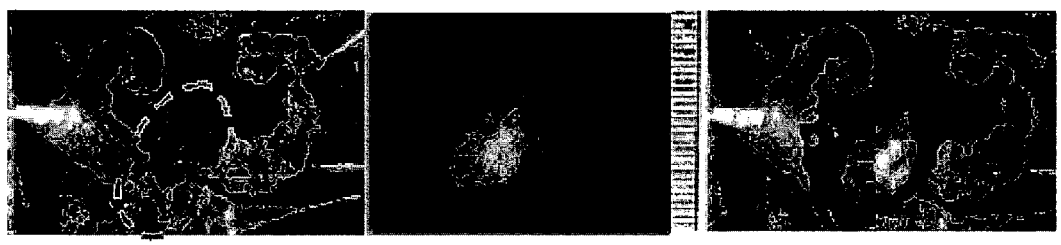
FIG. 21. Photo of excised prostate/vesicular gland complex (A). Bioscan image obtained 4 days post NM404 injection (B). Positionally matched fused photo/Bioscan image of excised prostate/vesicular gland (C) showing intense uptake of radioactivity in the prostate tumor.
Figure 22:
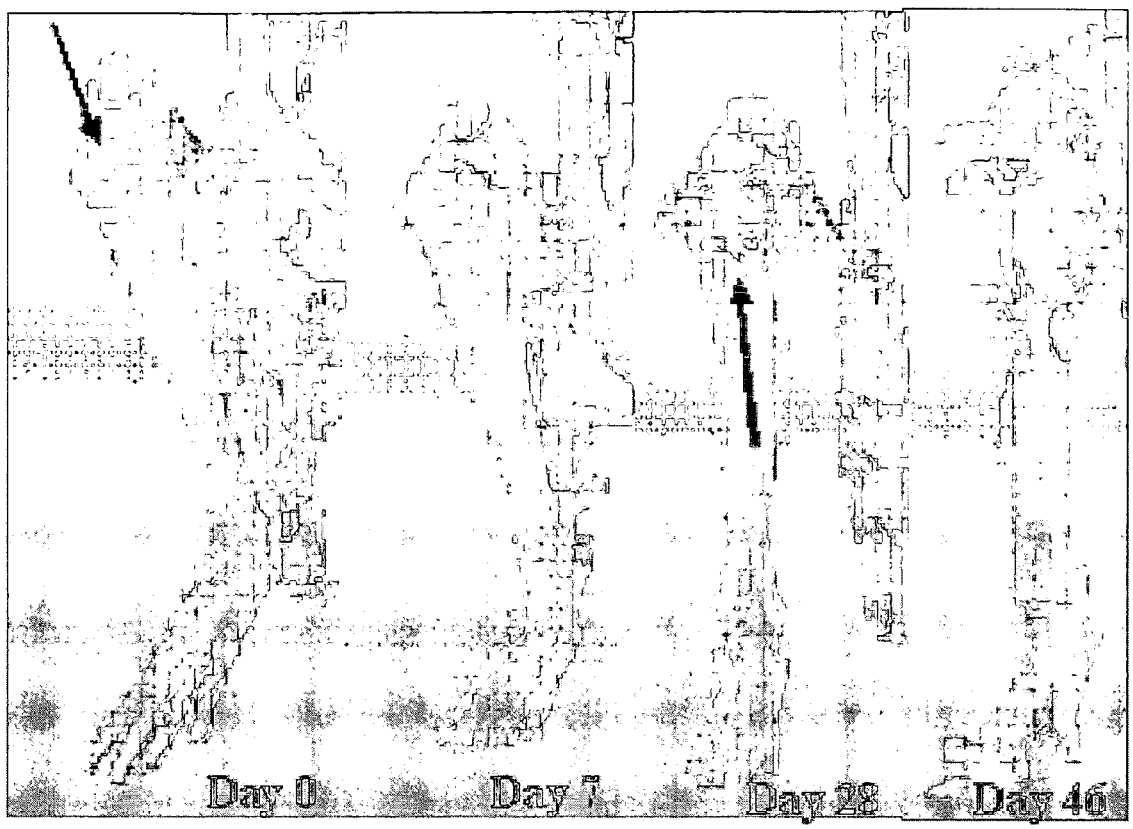
FIG. 22. High density 3D surface-rendered microCT images of a Nude mouse leg at various times following intratibial injection (arrow in first panel depicts injection site and direction) of $2 \times 10^5$ human PC3 prostate tumor cells. Tumor begins protruding through the bone by 28 days (arrow) and by 46 days the tumor has literally destroyed the tibia leaving only the fibula intact.
Figure 23:
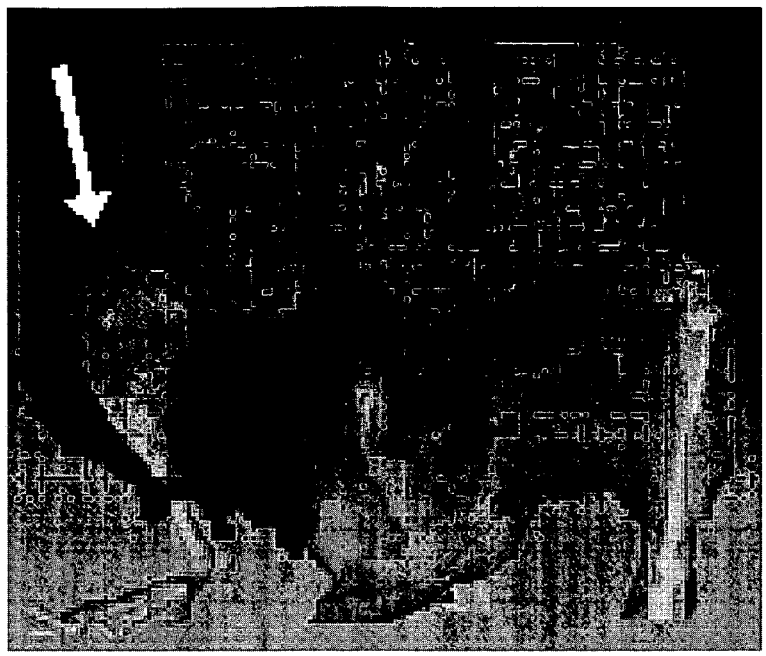
FIG. 23. Co-registered surface-rendered and coronal slice microCT image fused with positionally-matched Bioscan radionuclide scan (color) 4 days following injection of $^{125}$I-labeled NM404. Focal NM404 activity correlates well with tibial PC3 tumor (arrow).

Preliminary Scintigraphic Imaging Results with NM404 in Prostate Tumor-Bearing Mice: In a preliminary experiment to show that NM404 localizes in mouse prostate tumors, TRAMP mice were scanned on a Bioscan AR-2000 radioTLC scanner (modified in the lab for mouse imaging) from 1-8 days after tail vein injection of $^{125}$I-NM404 (15 µCi). Following in vivo imaging of anesthetized mice, the prostate tumors were removed immediately, and imaged ex vivo on the same scanner (equipped with high resolution 1 mm collimator and 2-D acquisition and analysis software) in order to avoid tissue attenuation associated with the low energy of iodine-125 (FIG. 21). Although the number of prostate tumor-bearing animals was small (n=4), preliminary images and tumor-to-background data indicated uptake of NM404 into prostate tumor but not benign hyperplasia found in this model. In an attempt to simulate bone metastases another experiment was performed wherein human PC-3 tumor cells were implanted into the tibia of immune compromised NUDE mice (n=6) according to a recent reports. Following tumor cell inoculation, mice were scanned serially by high-resolution microCT in order to monitor bone tumor development (FIG. 22). Once bone deterioration was detected, iodine-125 labeled NM404 was administered intravenously via tail vein. Mice were scanned for radioactivity and by microCT 4 days post NM404 administration. Radioactivity scans were fused with microCT scans (FIG. 23) to corroborate NM404 radioactivity and tumor location. Biodistribution Data Extensive biodistribution data for the prototype agent $^{125}$I-NM324 in several tumor models has previously been reported. Tumor-to-blood ratios exceeding 8:1 were seen at delayed times post-injection. For example, in a rat mammary tumor model, tumor-to-normal tissue ratios reached a maximum at 96 hours with a tumor-to-blood ratio of 8.6 and tumor-to-muscle ratio of 20:1. Moreover, the biodistribution of PLE-associated radioactivity is heterogeneous in tumor, as demonstrated by microautoradiogram studies showing that the PLE radioactivity resides exclusively in viable tumor cells located toward the outer regions rather than the central necrotic regions. Comparative biodistribution data for NM324 and NM404 in SCID mice have been obtained in prostate and A549 lung cancer tumor models. These studies revealed high tumor-to-normal tissue ratios and tumor uptake exceeding 25% of the injected dose with NM404, thus supporting the desire to examine the biodistribution of PLE analogs in humans.

Isotope Selection Because the tumor-targeting strategy of PLE analogs appears to involve selective tumor retention over time, relatively short-lived nuclides such as $^{18}$F or even $^{99m}$Tc are not practical for labeling NM404 at the current time. With a 13 h half-life and optimal imaging characteristics, iodine-123 may also prove suitable for this agent when scanned in a 3-dimensional SPECT mode. Imaging with iodine-123 will require further investigation. While tumor localization of PLE analogs appears to occur within several hours of injection (NM324 images obtained 6 h post injection in a lung cancer patient showed intense lung tumor uptake in a prior study), planar 2-dimensional imaging, like that currently being performed with iodine-131 in humans, requires a delay period to allow background activity to clear from neighboring normal tissues and blood. It is likely that earlier imaging may be possible when scanning with PET and 3D SPECT where neighboring radioactivity is less interfering due to the 3-dimensional nature of these modalities. In organs where background radioactivity remains inherently low (brain for example), it may be possible to use gamma emitting isotopes like iodine-123 which in addition to providing beautiful images, would permit image acquisition later on the same day of injection. Although the use of other isotopes may ultimately prove suitable for use with NM404, the current focus will develop the PET imaging capability of this agent due to the recent success of oncologic imaging using hybrid PET-CT scanners. The unsurpassed diagnostic accuracy afforded by a biochemical or functional tumor imaging PET agent combined with the precise anatomic accuracy provided by CT is now the gold standard for tumor imaging. However, it is highly advantageous to label PLE analogs with iodine-124, a relatively new PET isotope, wherein the physical half-life (4 days) matches well with PLE tumor uptake and retention kinetics. Labeling NM404 with iodine-124 represents a natural extension of prior studies with gamma-emitting nuclides. It has been shown that PET imaging with $^{124}$I affords over 40 times the sensitivity of planar 131I-gamma scintigraphy. PET, unlike traditional gamma camera imaging, also offers significant resolution enhancement, image quantification, and 3-dimensional capabilities. Due to the preliminary success of $^{131}$I-NM404 in the current lung cancer imaging trial, it is now imperative to label NM404 with iodine-124 and evaluate its tumor detection efficacy by PET in order to overcome the limitations inherently associated with planar scintigraphy The utility of tumor tracers like $^{67}$Ga-citrate and $^{18}$F-FDG is limited by their lack of specificity to distinguish neoplasm from inflammation. This lack of specificity is a significant clinical issue in patients with cancer. However, preliminary studies with PLE analogs offers promise in overcoming this limitation. Prior experiments conducted in rats revealed no uptake and retention of NM324 into carrageenan-induced granulomas. Gallium citrate, however, utilized as a control in this study, did indeed concentrate significantly in the granulomatous lesions. Thus, this preliminary finding that PLE analogs don't apparently localize in inflammatory lesions further justifies the need for evaluation of this agent in human cancer patients. Although FDG-PET has paved the way for hybrid imaging, its lack of tumor cell specificity will always limit its diagnostic efficacy. New molecularly targeted agents, like NM404, which display universal tumor uptake and selective retention regardless of location, as well as selectivity for malignant tumor cells and not inflammatory or hyperplastic lesions, will represent a significant improvement in the detection and characterization of cancer.

While planar nuclear medicine imaging techniques have historically afforded acceptable 2D images, this modality offers no tomographic capability and poor image quantitation. Although $^{125}$I-NM404 was suitable for preliminary scintigraphic imaging and tissue distribution studies in rodent tumor models and $^{131}$I was suitable for Phase 1 safety and pharmacokinetic evaluation in human lung cancer patients, neither are optimal for quantitative in vivo human imaging. PET imaging with iodine-124, a relatively new and commercially available positron isotope with a 4-day half-life, would alleviate many of the problems associated with planar imaging. Transitioning the unique tumor imaging capabilities of NM404 into PET scanning has now become a major goal of our lab since the iodine-124 became commercially available late last year. If the tumor specificity of NM404 for malignant tumors seen in mouse models is confirmed in humans, then we would have an agent with more tumor selectivity than FDG, albeit without its inflammatory site localization properties. Moreover, the agent could be manufactured in one facility and shipped to virtually any location in the world due to its 4-day half life.

Figure 24:
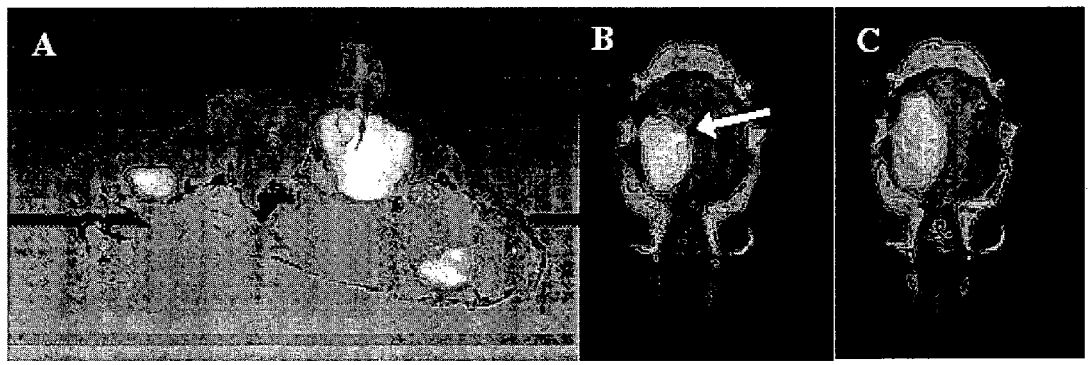
FIG. 24. Fused 3D surface-rendered MRI image (blue) and 3D microPET image (A) obtained 24 h after iv injection of $^{124}$I-NM404 (100 µCi) into a rat with a CNS-1 glioma brain tumor. Images were fused using Amira (v3.1). Right panels show (B) contrast-enhanced coronal MRI slice through the tumor (arrow) and (C) fused coronal MRI and $^{124}$I-NM404 microPET images corroborating presence and location of the tumor.

The inventors recently successfully radiolabeled NM404 twice with iodine-124 from a commercial vendor (Eastern Isotopes). The radiochemical yield (>60% mean isolated yield, >99% purity) was very similar to what we usually obtain with commercial sources of iodine-125 or 131 sodium iodide. The PET imaging characteristics of $^{124}$I-NM404 in a rat CNS-1 brain tumor model (FIG. 24) was investigated. Imaging times in this preliminary study were limited to 24 h and 4 days post injection due to microPET scanner availability. MicroPET images acquired 24 h after iv injection of $^{124}$I-NM404 were corroborated with contrast-enhanced MRI images and showed intense uptake of the tracer in the brain tumor accompanied by little or no uptake in surrounding intact brain tissue. This study represents the first PET image obtained with NM404 and demonstrates the ability to efficiently radiolabel, purify, and formulate NM404 for PET imaging. These compounds may then be used for extending NM404 PET utility into human cancer patients.

Determine Tumor Uptake and Retention Characteristics of $^{124}$I NM404 by PET-CT in Patients with Radiographically Evident Metastatic Prostate Cancer.

Objectives and Rationale

Assessment of whether selective detection of known metastatic lesions by radioiodinated NM404 is possible and comparable to conventional radiologic modalities is discussed in the following paragraphs. Inclusion criteria for this study will consist of fifteen patients with metastatic prostate cancer, with at least 5 patients having soft-tissue prostate cancer metastases and at least 5 of the patients with bony metastases identifiable by conventional radiologic studies which include CT scan and bone scan. Following patient enrollment, uptake of radiolabeled NM404 will be measured by I-124 isotope PET-CT scan and correlated with the radiographically evident lesions detected by the patient's other conventional staging studies.

Methods

Synthesis, Radiolabeling, and Formulation: Radioiodination of stable NM404 with $^{124}$I -sodium iodide is routinely achieved by modification of an ammonium sulfate-mediated isotope exchange reaction reported by Mangner and recently optimized for NM404 in our lab. Exchange reaction methodology has been used effectively for initial human trials with NM324, the predecessor of NM404 and is currently being used for preclinical studies and the human lung cancer trial. Briefly, a 2-ml glass vial is charged with 10 mg of ammonium sulfate dissolved in 50 µl of deionized water. Fourteen 2 mm chemical resistant glass beads are added, a Teflon lined septum and screw cap are added and the vial gently swirled. A solution of 20 µg (in 20 µl of ethanol) of stock NM404 is added followed by aqueous sodium iodide (124, 1-5 mCi) in less than 30 µl aqueous 0.01 N sodium hydroxide. The isotope syringe is rinsed with three 20-µl portions of ethanol. The reaction vile is swirled gently. A 5-ml disposable syringe containing glass wool in tandem with another 5-ml charcoal nugget filled syringe with needle outlet are attached. The glass wool syringe acts as a condensation chamber to catch evaporating solvents and the charcoal syringe traps free iodide/iodine. The reaction vessel is heated in a heating block apparatus for 45 minutes at 150° C. Four 20 ml volumes of air are injected into the reaction vial with a 25-ml disposable syringe and allowed to vent through the dual trap attachment. The temperature is raised to 160° C and the reaction vial is heated another 30 minutes. After cooling to room temperature, ethanol (200 µl) is added and the vial swirled. The ethanolic solution is passed through a pre-equilibrated Amberlite IRA 400-OH resin column to remove unreacted iodide. The eluent volume is reduced to 50 µl via a nitrogen stream (use charcoal syringe trap) and the remaining volume injected onto an HPLC silica gel column (Perkin Elmer, 3 μm×3cm disposable cartridge column eluted at 1 ml/min with hexane/isopropanol/water (52:40:8)) for purification. Final purity is determined by TLC (plastic backed silica gel-60 eluted with chloroform-methanol-water (65:35:4, Rf=0.1). The HPLC solvents are removed by rotary evaporation and the resulting radioiodinated NM404 is solubilized in aqueous 2% pharmaceutical grade Polysorbate-20 (0.1 μl/mg of compound). The ethanol is removed under vacuum and the residue dissolved in sterile water to give a final solution containing no more than 2-3% Polysorbate-20. Sterilization will be achieved by filtration through a sterile 0.2 μm filter unit. Each of the solutions will be tested for pyrogens using the Limulus Amebocyte Lysate test kit. This is the same procedure currently employed for the preparation, purification and sterile formulation of I-131-labeled NM404 for lung cancer patient studies. The drug Master Formulation Card and Product Preparation Checklist are included in the supplemental section of this proposal. We have performed this radioiodination hundreds of times with either iodine-131 or 125 and typically achieve radiochemical yields ranging from 60-90% (isolated pure product) with specific activities of exceeding 130 mCi/pmol of NM404. This method has afforded sufficient pure injectable $^{131}$I-NM404 for our ongoing preclinical and human trials. We have not had a labeling failure to date. Moreover, and relevant to the current proposal, we have recently successfully radiolabeled NM404 with iodine-124 sodium iodide (5 mCi) from Eastern Isotopes in >60% isolated radiochemical yield. Although acceptance criteria require >95% radiochemical purity, results typically exceed 99% since the entire reaction mixture is subjected to preparative HPLC purification.

I-124 Dose for Human Administration: The toxicity profile, biodistribution, kinetics, optimal imaging times, and dosimetry of $^{131}$I NM404 are currently being evaluated in an ongoing study in patients with lung cancer (NSCLC) at UWCCC, as discussed above. Dosing of radioiodinated $^{124}$I NM404 will be based on MIRD extrapolation of the iodine-131 dosimetry data derived from this ongoing study. The $^{131}$I-NM404 dose is currently calculated as follows: Animal biodistribution data is used to determine the percentage of injected dose/organ at varying time points. These animal data are extrapolated to man by means of MIRD formalism (MIRDOSE PC v3.1) using standard conversion factors for differences in organ mass and anatomy between rat and standard man, providing predicted human organ doses; Based on these predicted doses, the permissible mCi dose to be injected into humans is determined using the maximal doses legally permitted by RDRC regulations for specific human tissue as defined in the Federal Register (21CFR Part 361.1) e.g. whole body, blood, blood forming tissues, eye lens, gonads—3 rem/dose; any other tissue—5 rem/dose. This approach was previously used to bring both NM324 and NM404 to clinical use, resulting in a calculated dose of 1 mCi. New animal data acquired with NM404 (5 rad testes dose=2.1 mCi and 5 rad dose to adrenals=2.2 mCi) indicate the starting maximum dose of $^{131}$I -NM404 will be around 1.9 mCi or twice that of NM324.

Study Procedures: Before infusion, an intravenous line will be established in the arm. The tracer dose <0.3 μg/kg body weight $^{124}$I-NM404 (1 mCi, actual dose pending current study dosimetry results) will be infused over 5 minutes. The preparation will be sterile, pyrogen-free, and contain <5% free iodine by thin layer chromatography (usual result is <1%). The patient will be clinically monitored for adverse reactions during the infusion.

Since the animal toxicity studies (using over 1,000 times the maximum planned quantity of $^{124}$I-NM404 in this study) and the preliminary clinical safety studies with the unlabeled compound (at doses 10 times greater) were without side effects, we do not anticipate toxicity at the imaging dose. However, we are cognizant of the possibility of untoward allergic or other reactions. The patients' vital signs (pulse, BP, temperature and respiratory rate) will be re-checked immediately after the infusion and at 30 and 60 minutes post injection. The vital signs will then be checked each hour for two hours.

Baseline PET-CT images (whole body and selected regional conjugate views) for the first five patients will be obtained at 48 and 96 hours post injection. PET images will be obtained using a GE Clinical GE Discovery LS PET-CT scanner utilizing appropriate attenuation correction and optimized to iodine-124. The 48 and 96 hour time points are based on preliminary data regarding optimal imaging times for $^{131}$I-NM404 in lung cancer, however, the optimum tumor-targeting time for $^{124}$I-NM404 in human prostate cancer is yet to be determined.

$^{124}$I-NM404 tracer accumulation and washout will be recorded on the GE Discovery LS PET/CT scanner or on GE Advance PET scanner available at our clinic. A CT scan will be performed first for patient localization and attenuation correction on the Discovery LS PET/CT scanner; a transmission scan will be performed on the Advance PET scanner. Each PET scan will be corrected for random, dead time, attenuation, and scatter. First scanning will be performed immediately at 48 and 96 h after the $^{124}$I-NM404 injection. Whole body scans will be performed with increased scanning time over the tumor site (up to 30 min). Images will be reconstructed using an iterative OSEM reconstruction method with attenuation correction, and smoothed with a Gaussian filter.

Data evaluation will be based on a region-of-interest (ROI) analysis of coregistered PET images. CTs from each PET/CT scan will be co-registered to enable accurate positioning of the PET data. ROIs will be outlined to represent various organs in the field of view (typically heart, lung, muscle, liver, stomach, spleen, intestine, kidney, and bladder). For each ROI and for each time frame, the average radioactivity concentration will be calculated and standardized uptake values (SUVs) calculated. Detailed pharmacokinetic analysis will not be performed in this study, but will have been completed in the ongoing lung cancer trial and not duplicated here, because this will be performed in the lung cancer trial, wherein 2 patients will undergo PET scanning immediately after, and subsequently at 6, 24, and 48 h post NM404 infusion. SUVs will be plotted as time-activity curves. The time course of radioactivity in each ROI will be fitted using various kinetic models including a two-rate constant in a two compartment model and a four-rate and three-rate constant, in a three compartment model in conjunction with the non-linear regression fitting. The nonlinear least-square fitting will be done using a modified gradient-expansion algorithm. The best fits will be determined by minimizing a $\chi^2$ function with respect to variations in the model parameters. For the 3k model the data will be fit with $k_4$ set equal to 0 in order to test the assumption of the phospholipid irreversible trapping in the tumor membrane. In addition, Patlak plots will be used to standardize the kinetics of tissue radioactivity to the kinetics of plasma radioactivity.

Statistical Considerations: This is a feasibility study to determine the tumor uptake and retention characteristics of radioiodinated $^{124}$I NM404 by PET-CT in patients with clinically evident metastatic prostate canter. Fifteen patients with metastatic prostate cancer will be accrued for Part 1 of this study. Image scans will be scored using a typical 0-3 scale: 0=no perceptible uptake, 1+=uptake barely perceptible above background, 2+=uptake clearly distinguishable above background, 3+=intense uptake, much greater than surrounding normal structures (2+and 3+are considered abnormal or positive for lesion identification; 0 and 1+are considered normal or negative for lesion identification). An uptake rate classified as positive for lesion identification of at most 50% would be considered as clinically irrelevant. Therefore, we will test the null hypothesis that the uptake rate classified as positive for lesion identification will be at most 50% versus the alternative hypothesis that the rate is greater than 50%. We anticipate the uptake rate classified as positive for lesion identification will be at least 80%. Assuming a total sample size of 15 patients, the one-sample binomial test with the null hypothesis that the uptake rate classified as positive is at most 50% has 85% power to detect a rate of 80% at the (one-sided) 10% significance level. A rate of 90% will be detected with 95% power. With a sample size of 15 patients, the proportion of tumors classified as positive for lesion identification will have a standard error of at most 13% and the 90% confidence interval for the proportion will be no wider than 39%.

Determine the Specific Tumor Accumulation and Metabolic Fate of $^{124}$I NM404 in Patients with Clinically Organ-confined Prostate Cancer who are Candidates for a Radical Prostatectomy with Bilateral Pelvic Lymph Node Dissection.

Objectives and Rationale

As a secondary exploratory analysis, malignant and benign prostatic and nodal tissue obtained by radical prostatectomy and bilateral lymph node dissection will be evaluated for radioiodinated NM404 accumulation and metabolites of NM404 and data from this tissue analysis will be compared with the results of final pathology analysis. Ten patients with organ-confined prostate cancer who are scheduled to undergo a radical prostatectomy with bilateral pelvic lymph node dissection will be enrolled. All patients will undergo conventional preoperative staging studies which include CT scan and bone scan. All patients will also have an NM404 PET-CT scan the week before the scheduled prostatectomy. Final pathologic analysis of the resected prostate and lymph nodes will be correlated with results of the NM404 accumulation and metabolite tissue assay to determine relationship of signal to tumor volume in the primary specimen and lymph nodes in patients with locoregional metastatic disease. Nodal metastases detected by the NM404 accumulation despite a negative preoperative CT scan and bone scan would have great clinical significance in terms of improved staging of these patients prior to treatment.

Study Procedures: Imaging procedures in this study will be identical to the first study, except that patients will be imaged only once, based upon the optimal imaging time as identified in the first protocol (probably between 24-48 hours after the injection). Six prostate biopsy cores will be obtained in sextant distribution (right and left apex, mid-gland and base regions) from the prostate specimen in the OR immediately following surgical removal. These six biopsy cores will be evaluated by frozen section pathology to ensure a representative sampling of both malignant and benign prostate tissue. A second set of 6 biopsy cores obtained simultaneously from the same corresponding locations in the prostate will be analyzed for uptake of $^{124}$I-NM404. Accordingly, they will be photographed and undergo high-resolution scanning on a Bioscan AR2000 radioscanner and also weighed and radioactivity quantitated in a well counter. Radioactivity concentration will be determined on a % dose/g tissue sample basis for comparison. These results will be compared to histology results in order to confirm localization in tumor relative to surrounding uninvolved tissue. The core biopsies will be labeled with the patient's study identification number and location in the prostate from which it was obtained.

Final pathology of any lymph nodes harboring metastatic prostate tumor will also be correlated with $^{124}$I-NM404 uptake signal detected by the preoperative PET-CT scan. Vital signs will be obtained post $^{124}$I-NM404 infusion.

Statistical Considerations: Ten patients with high-risk clinically localized prostate cancer will be accrued for Part 2 of the study. The null hypothesis for Part 2 is that the log ratio of the accumulation of NM404 in tumor tissues to that in normal surrounding tissues in clinically localized prostate cancer patients is zero. The alternative hypothesis is that the log ratio of the accumulation of NM404 is greater than 0. A tumor-to-adjacent normal tissue (T/N) ratio of at least 5:1 would be considered as clinically relevant. Based on past experience with NM404, it is anticipated that the standard deviation of the log ratio of the accumulation of NM404 is between 1.5 and 2.0. With a sample size of 10, the one-sided t-test with a one-sided 10% significance level has 86%, 90% and 95% power to detect the effect size of 0.8, 0.90, and 1.00, respectively. For example, if the standard deviation of the log ratio is 2.0, the 5:1 ratio in the accumulation of NM404 in the tumor to normal tissues will be detected with 86% power. Analogously, if the standard deviation of the log ratio is 1.6, a ratio of 5:1 in the accumulation of NM404 in tumor to normal tissues will be detected with 95% power.

Determine Whether NM404 Can Detect Metastatic Recurrence Following Primary Treatment of Prostate Cancer in Ten Patients with a Rising PSA as Their Only Evidence of Disease (Stage D0).

Objectives and Rationale

By definition, patients with stage D0 prostate cancer have a rising PSA following definitive treatment of their disease, signifying biochemical recurrence, with conventional staging studies including CT scan and bone scan which are negative for radiographic evidence of disease. Patients more likely to have disease detectable by the NM404 PET-CT scan will be enrolled such that they must have a PSA rise of greater than 0.75 ng/ml/year.

Study procedures: Imaging procedures in this study will be identical to the first study, except that patients will be imaged only once, based upon the optimal imaging time as identified in the first protocol. Patients will receive an injection of $^{124}$I-NM404 (0.3 µg/kg body weight, 1 mCi or the limit established by dosimetry calculations in the first set of patients). Patients will also have a PET-CT scan 48 hours after infusion. Vital signs will be obtained post $^{124}$I-NM404 infusion.

Statistical Considerations: Ten patients with stage D0 prostate cancer will be accrued and followed-up for metastatic recurrence for at least 2 years. Since all patients accrued in this part of the study will have PSA values greater than 0.75 ng/ml/year, we expect that at least 60% will experience metastatic recurrence within 2 years. Assuming that 6 out of the 10 patients will eventually experience metastatic recurrence within 2 years, the sensitivity of NM404 to detect metastatic recurrence will be estimated with a standard error of less than 20% and the 90% confidence interval for the sensitivity will be no wider than 55%. Furthermore, the null hypothesis that the sensitivity of NM404 in this patient population is at most 30% will be tested against the alternative that the sensitivity is greater than 30%. The one-sample binomial test has 83% power to detect a sensitivity of 75% at the one-sided 10% significance level. A sensitivity of 80% will be detected with 90% power.

Approximately 230,110 new cases of prostate cancer will be diagnosed in the United States for the year 2004 alone. Despite technical refinements in definitive local treatment of clinically organ confined prostate cancer by radical prostatectomy, such that many men are cured with primary therapy alone, as many as 40% of patients will experience biochemical recurrence with long-term follow-up. One of the greatest challenges in treating patients with clinically organ confined prostate cancer or patients with biochemical recurrence following definitive treatment of presumed organ-confined disease remains to accurately distinguish localized versus metastatic disease. This diagnostic capability is important to identify patients who may benefit from effective local treatment modalities including surgery, external beam radiation, brachytherapy, and cryotherapy. Because we presently do not have an accurate means of staging, patients with occult metastatic disease may unnecessarily undergo local treatment with associated risks of therapy. Furthermore, patients with a rising PSA due to local recurrence, in whom systemic recurrence cannot be excluded with confidence, may unnecessarily undergo hormonal ablation, which is generally not considered curative and is associated with osteoporosis development, decreased libido, weight gain, menopausal symptoms, and overall malaise, as well as the evolution of hormonally independent prostate cancer.

While conventional imaging studies such as computed tomography (CT) and magnetic resonance imaging (MRI) are useful in assessing soft-tissue metastasis, the vast majority of prostate cancer metastasizes to the bone only. Thus, the utility of CT and MRI scanning in assessing the disease is suboptimal and more sensitive imaging modalities for either locally recurrent or metastatic prostate cancer are necessary. Radioimmunoscintigraphy with Indium-111 capromab pendetide (ProstaScint, Cytogen Corp, Princeton, N.J.) has been utilized in patients following prostatectomy with a rising PSA who have a high clinical suspicion of occult metastatic disease and no clear evidence for metastatic disease in other imaging studies. Use of the ProstaScint scan for patients at risk for occult metastases from prostate cancer remains controversial however. One approach to the development of a sensitive imaging exam is to develop a more appropriate carrier molecule, which is key to achieving delivery of a radiopharmaceutical probe to the desired target tissue. Our strategy has been to study radioiodinated phospholipid ether analogs (PLE) as potential diagnostic imaging agents, to capitalize on the unique biochemical or pharmacological properties of these molecules resulting in a high degree of tissue or tumor selectivity. In preclinical models, we have shown these molecules selectively accumulate in a wide variety of murine and human tumors in high levels.

Certain embodiments of the present invnetion provides preliminary data regarding the use of the second-generation PLE analog, NM404, in imaging patients with prostate cancer. It has been shown that NM404 is (a) selectively retained in a wide variety of tumor types in preclinical models, with a high degree of sensitivity, (b) is safe in humans, (c) can be radiolabeled with I-124, and (d) has appropriate dosimetry characteristics labeled with I-131.

References

Jemal A., R. C. Tiwari, T. Murray, et al. C A. *A Cancer J for Clinicians*. 2004; 54(1):8-29.

Han M, Partin A W, Zahurak M, Piantadosi S, Epstein J I, Walsh P C. J Urol. 2003;169(2):517-23.

Lange P H, Ercole C J, Lightner D J, Fraley E E, Vessella R. The value of serum prostate specific antigen determinations before and after radical prostatectomy. J Urol. 1989;141 (4): 873-9.

Amling C L, Bergstralh E J, Blute M L, Slezak J M, Zincke H. Defining prostate specific antigen progression after radical prostatectomy: what is the most appropriate cut point? J Urol. 2001;165(4):1146-51.

Freedland S J, Sutter M E, Dorey F, Aronson W J. Defining the ideal cutpoint for determining PSA recurrence after radical prostatectomy. Prostate-specific antigen. Urology. 2003; 61 (2):365-9.

Jhaveri F M, Klein E A. How to explore the patient with a rising PSA after radical prostatectomy: defining local versus systemic failure. Semin Urol Oncol. 1999;17(3):130-4.

Moul J W. Prostate specific antigen only progression of prostate cancer. J Urol. 2000;163(6):1632-42.

Neulander E Z, Soloway M S. Failure after radical prostatectomy. Urology. 2003;61 (1):30-6.

Partin A W, Pearson J D, Landis P K, Carter H B, Pound C R, Clemens J Q, Epstein J I, Walsh P C. Evaluation of serum prostate-specific antigen velocity after radical prostatectomy to distinguish local recurrence from distant metastases. Urology. 1994;43(5):649-59.

Patel A, Dorey F, Franklin J, deKernion J B. Recurrence patterns after radical retropubic prostatectomy: clinical usefulness of prostate specific antigen doubling times and log slope prostate specific antigen. J Urol. 1997; 158(4):1441-5.

Raj G V, Partin A W, Polascik T J. Cancer. 2002;94(4):987-96.

Elgamal A A, Troychak M J, Murphy G P. Prostate. 1998; 37(4):261-9.

Hricak H, Schoder H, Pucar D, Lis E, Eberhardt S C, Onyebuchi C N, Scher H I. Semin Oncol. 2003;30(5):616-34.

Smith-Jones P M, Vallabhajosula S, Navarro V, Bastidas D, Goldsmith S J, Bander N H. Radiolabeled monoclonal antibodies specific to the extracellular domain of prostate-specific membrane antigen: preclinical studies in nude mice bearing LNCaP human prostate tumor. J Nucl Med. 2003;44 (4):610-7.

Zanzi I, Stark R: Detection of a non-Hodgkin's lymphoma by capromab pendetide scintigraphy (ProstaScint) in a patient with prostate carcinoma. Urology 2002;60:514.

Zucker R J, Bradley Y C: Indium-111 capromab pendetide (ProstaScint) uptake in a meningioma. Clin Nucl Med. 2001 ;26:568-569.

Scott D L, Halkar R K, Fischer A, et al: False-positive 111 indium capromab pendetide scan due to benign myelolipoma. J Urol. 2001;165:910-911,.

Khan A, Caride V J: Indium-111 capromab pendetide (ProstaScint) uptake in neurofibromatosis. Urology 2000;56: 154.

Valliappan S, Joyce J M, Myers D T: Possible false-positive metastatic prostate cancer on an In-111 capromab pendetide scan as a result of a pelvic kidney. Clin Nucd Med. 1999;24: 984-985.

Michaels E K, Blend M, Quintana J C: 111 Indium-capromab pendetide unexpectedly localizes to renal cell carcinoma. J Urol. 1999;161i:597-598.

Yeung H, Schoder H, Larson S: Utility of PET-CT for assessing equivocal PET lesions in oncology-Initial experience. J Nucl Med. 2002;43:32P (abstr).

Nunez R, Macapinlac H A, Yeung H W, Akhurst T, Cai S, Osman I, Gonen M, Riedel E, Scher H I, Larson S M. Combined 18F-FDG and 11C-methionine PET scans in patients with newly progressive metastatic prostate cancer. J Nucl Med. 2002;43(1):46-55.

Morris M J, Akhurst T, Osman I, Nunez R, Macapinlac H, Siedlecki K, Verbel D, Schwartz L, Larson S M, Scher HI.

Fluorinated deoxyglucose positron emission tomography imaging in progressive metastatic prostate cancer. Urology 2002;59(6):91 3-8.

Seltzer M A, Barbaric Z, Belldegrun A, Naitoh J, Dorey F, Phelps M E, Gambhir S S, Hoh C K. Comparison of helical computerized tomography, positron emission tomography and monoclonal antibody scans for evaluation of lymph node metastases in patients with prostate specific antigen relapse after treatment for localized prostate cancer. J Urol. 1999;162(4):1322-8.

Counsell R E, Longino M, Pinchuk A., Skinner S, Weichert J P. Synthesis and evaluation of radioiodinated phospholipid ethers for imaging of prostate cancer. Quart J Nucl Med. 1997; 41, 14-16.

Snyder F, Wood R. Alkyl and alk-1-enyl ethers of glycerol in lipids from normal and neoplastic human tissues. Cancer Res 1969; 29:251-257.

Snyder F, Blank M L, Morris H P. Occurrence and nature of O-alkyl and O-alk-I-enyl moieties of glycerol in lipids of Morris transplanted hepatomas and normal rat liver. Biochim Biophys Acta 1969; 176:502-510.

Rampy M A, Pinchuk A N, Weichert J P, Skinner R W, Fisher S J, Wahl R L, Gross M D, Counsell R E. Synthesis and biological evaluation of radioiodinated phospholipid ether stereoisomers. J Med Chem 1995; 38:3156-3162.

Plotzke K P, Rampy M A, Meyer K, Ruyan M, Fisher S J, Wahl R L, Skinner R W, Gross M D, Counsell R E. Biodistribution, metabolism, and excretion of radioiodinated phospholipid ether analogs in tumor-bearing rats. J Nucl Biol Med 1993; 37:264-272.

Pinchuk A N, Rampy M A, Longino M A, Skinner R W S, Gross M D, Counsell R E, Weichert J P. Synthesis and structure activity relationship effects on the tumor avidity of radioiodinated phospholipid ether analogs. J. Med Chem (in Press 2006).

Weichert J P Vandort M E, Groziak M P, Counsell R. Radioiodination via isotope exchange in pivalic acid. Int J Appl Rad Isotopes 1986; 38:907-913.

Rampy M A, Brown R S, Pinchuk A N, Weichert J P, Skinner R W, Fisher S J, Wahl R L, Gross M D, Ethier S P, Counsell R E. Biological disposition and imaging of a radioiodinated alkylphosphocholine in two rodent models of breast cancer. J Nucl Med 1996; 37:1540-1545.

Plotzke K P, Haradahira T, Stancato L, Olken N M, Skinner S, Gross M D, Wahl R L, Counsell R E. Selective Localization of Radioiodinated Alkylphosphocholine Derivatives in Tumors. Nuclear Medicine and Biology 1992; 19:765-773.

Berlin 0, Samid D, Conthineni-Rao R, Akeson W, Amiel D Woods V L. Development of a novel spontaneous metastiasis model of human ostersarcoma transplanted orthotopically into bone or athymic mice. Cancer Res. 1993; 53:4890-95.

Corey E, Quinn J E, Bladou F, Brown L G, Roudier M P, Brown J M, Buhler K R, Vessella R L. Establishment and characterization of osseous prostate cancer models:lntratibial injection of human prostate cancer cells. The Prostate 2002; 52:20-33.

Plotzke K P, Fisher S J, Wahl R L, Olken N M, Skinner S, Gross M D, Counsell R E. Selective localization of a radioiodinated phospholipid ether analog in human tumor xenografts. J Nucl Med 1993; 34:787-792.

Pentlow K S, Graham M C, Lambrecht R M, Daghighian F, Bacharach S L, Bendriem B, Finn R D, Jordan K, Kalaigian H, Karp J S, Robeson W R, Larson S M. Quantitative imaging of iodine-124 with PET. Journal of Nuclear Medicine 1996; 37:1557-1562.

Blasberg R G, Roelcke U, Weinreich R, Beattie B, von Ammon K, Yonekawa Y, Landolt H, Guenther I, Crompton N E A, Vontobel P, Missimer J, Maguire R P, Koziorowski J, Knust E J, Finn R D, Leenders K L. Imaging brain tumor proliferative activity with [I-124]iododeoxyuridine. Cancer Research 2000; 60:624-635.

Counsell R E, Schwendner S W, Meyer K L, Haradahira T, Gross M D. Tumor visualization with a radioiodinated phospholipid ether. J Nucl Med 1990; 31:332-336.

Moser A R, Pitot H C, Dove W F. A Dominant Mutation that Predisposes to Multiple Intestinal Neoplasia in the Mouse. Science 1990; 247:322-324.

Moser, A R, Hegge, L F, and R D Cardiff. Genetic background affects susceptibility to mammary tumors and hyperplasias in $Apc^{min}$/+mice. Cancer Research 2001; 61:3480-3485.

Mangner T J, Wu J L, Wieland D M. Solid-phase exchange radioiodination of aryl iodides. Facilitation by ammonium sulfate. J Org Chem. 1982; 47(8):1484-1488.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A method for detecting and locating a cancer in vivo, the method comprising the steps of:
    administering $^{124}$I-labeled 18-(p-Iodophenyl)octadecyl phosphocholine to the human subject; and
    determining whether an organ suspected of having the cancer in the subject retains a higher level of $^{124}$I-labeled 18-(p-Iodophenyl)octadecyl phosphocholine than surrounding region(s), wherein a higher retention region indicates detection and location of the cancer, wherein the detection is carried out by PET scanning.

2. The method of claim 1, wherein the detection is carried out by a combination of PET scanning and CT or MRI scanning methods.

3. The method of claim 1, wherein the cancer is selected from the group consisting of lung cancer, squamous cell carcinoma, melanoma, colorectal cancer, ovarian cancer, prostate cancer, glioma, breast cancer, carcinosarcoma, and pancreatic cancer.

4. The method of claim 1, comprising administering between about 0.5 µCi and about 500 mCi of the $^{124}$I-labeled 18-(p-Iodophenyl)octadecyl phosphocholine to the human subject.

5. The method of claim 1, comprising administering less than 0.3 µg/kg of body weight of the $^{124}$I-labeled 18-(p-Iodophenyl)octadecyl phosphocholine to the human subject.

* * * * *